United States Patent
Gray et al.

(10) Patent No.: US 11,535,859 B1
(45) Date of Patent: Dec. 27, 2022

(54) CONTROLLING STOMATAL DENSITY IN PLANTS

(71) Applicant: The University of Sheffield, Sheffield (GB)

(72) Inventors: Julie Elizabeth Gray, Sheffield (GB); Lee Hunt, Sheffield (GB); William Paul Quick, Sheffield (GB)

(73) Assignee: The University of Sheffield, Sheffield (GB)

( * ) Notice: Subject to any disclaimer, the term of this patent is extended or adjusted under 35 U.S.C. 154(b) by 0 days.

(21) Appl. No.: 16/608,683

(22) PCT Filed: Apr. 26, 2018

(86) PCT No.: PCT/GB2018/051096
§ 371 (c)(1),
(2) Date: Oct. 25, 2019

(87) PCT Pub. No.: WO2018/197878
PCT Pub. Date: Nov. 1, 2018

(30) Foreign Application Priority Data

Apr. 27, 2017 (GB) .................................. 1706755

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8281* (2013.01); *C12N 15/8282* (2013.01)

(58) Field of Classification Search
None
See application file for complete search history.

(56) References Cited

U.S. PATENT DOCUMENTS

2013/0007920 A1* 1/2013 Nishimura ........... C07K 14/415 800/298

FOREIGN PATENT DOCUMENTS

| WO | 2007086402 A1 | 8/2007 |
| WO | 2018197878 A1 | 11/2018 |

OTHER PUBLICATIONS

Combined Search and Examination Report of GB1706755.4, dated Jan. 29, 2018, 7 Pages.

International Search Report and Written Opinion of PCT/GB2018/051096, dated Jul. 5, 2018, 12 Pages.
Franks et al., Increasing water-use efficiency directly through geneticmanipulation of stomatal density, 2015, New Phytologist, vol. 207, pp. 188-195.
Hara et al., The secretory peptide gene EPF1 enforces the stomatalone-cell-spacing rule, 2007, Genes & Development, vol. 21, pp. 1720-1725.
Hepworth et al., Manipulating stomatal density enhances drought tolerance without deleterious effect on nutrient uptake, 2015, New Phytologist, vol. 208, pp. 336-341.
Hughes et al., Reducing Stomatal Density in Barley Improves DroughtTolerance without Impacting on Yield1[CC-BY], 2017, Plant Physiology, vol. 174, pp. 776-787.
Lawson et al., The cloning and characterization of a poplar stomatal density gene, 2014, Genes Genomics, vol. 36, pp. 427-441.
Rychel et al., Plant twitter ligands under 140 amino acids enforcing stomatal patterning, 2010, J Plant Research, vol. 123(3), pp. 275-280.
Takata et al., Evolutionary Relationship and Structural Characterization of the EPF/EPFL Gene Family, 2013, PLoS One, vol. 8(6), 6 Pages.
Wang et al., PdEPF1 regulates water-use efficiency and drought-tolerance by modulating stomatal density in poplar, 2016, Plant Biotech. Journal, vol. 14, pp. 849-860.
Hepworth et al. "Stomatal development: focusing on the grasses." Current Opinion in Plant Biology 41: 1-7 (2018).
Huang et al. "BnEPFL6, an Epidermal Patterning Factor-Like (EPFL) secreted peptide gene, is required for filament elongation in *Brassica napus*." Plant Molecular Biology 85(4-5): 505-517 (2014).
Tameshige et al. "A secreted peptide and its receptors shape the auxin response pattern and leaf margin morphogenesis." Current Biology 26(18): 2478-2485 (2016).
Uchida et al. "Regulation of inflorescence architecture by intertissue layer ligand-receptor communication between endodermis and phloem." Proceedings of the National Academy of Sciences 109(16): 6337-6342 (2012).
Uchida et al. "Regulation of plant vascular stem cells by endodermis-derived EPFL-family peptide hormones and phloem-expressed ERECTA-family receptor kinases" Journal of Experimental Botany 64(17): 5335-5343 (2013).

\* cited by examiner

*Primary Examiner* — Elizabeth F Mcelwain
(74) *Attorney, Agent, or Firm* — Nixon Peabody LLP; Linda Huber; Nicole D. Kling

(57) ABSTRACT

The present invention relates to the modification of gene expression in plants in order to manipulate stomatal number, in particular to the modification of expression in plants of epidermal patterning factor (EPF). The invention also relates to genetically modified plants or plant parts with altered stomatal patterning compared to corresponding wild type plants or plant parts, where the plant stomatal development is altered by modification of the expression of EPF.

5 Claims, 17 Drawing Sheets
Specification includes a Sequence Listing.

A

B

A

B

CONTROLLING STOMATAL DENSITY IN PLANTS

CROSS-REFERENCE TO RELATED APPLICATIONS

This application is a 35 U.S.C. § 371 National Phase Entry Application of International Application No. PCT/GB2018/051096 filed Apr. 26, 2018, which designates the U.S. and claims benefit under 35 U.S.C. § 119(a) of G.B. Provisional Application No. 1706755.4 filed Apr. 27, 2017, the contents of which are incorporated herein by reference in their entireties.

SEQUENCE LISTING

The instant application contains a Sequence Listing which has been filed electronically in ASCII format and is hereby incorporated by reference in its entirety. Said ASCII copy, created on Jun. 17, 2020 is named 065493-000012US00_SL.txt and is 50,888 bytes in size.

FIELD OF THE INVENTION

The present invention relates to the modification of gene expression in plants in order to manipulate the growth and/or structure of a plant through modulation of stomatal number. More particularly, the invention relates to the modification of expression in plants of epidermal patterning factor (EPF). The invention also relates to genetically modified plants or plant parts with altered stomatal patterning compared to corresponding wild type plants or plant parts, wherein plant stomatal development is altered by modification of the expression of EPF. Said plants have improved drought resistance, and/or improved resistance to pathogen infection to suit growth in a variety of conditions.

BACKGROUND TO THE INVENTION

With the global population set to rise to over 9 billion by 2050 and the predicted instability in global climate patterns, fears over global food security continue to grow (Godfray et al., 2010, Science 327: 812-818) Prolonged periods of drought and expanded zones of desertification are expected to become increasingly prevalent as this century progresses (IPCC, 2014: Climate Change 2014: Synthesis Report. 151). The need to expand agriculture into areas of marginal land, where drought is a severe inhibitor of sustainable agriculture (Fita et al., 2015, Frontiers in Plant Science 6: 978), continues to increase. 70% of global freshwater is already utilised for irrigation and rain-fed agriculture is now the world's largest consumer of water (Foley et al. 2011, Nature 478: 337-342). A potential way to both future-proof against climate change, and to expand crop production onto water-limited marginal lands would be through improvements to crop drought tolerance and water use efficiency (WUE, the ratio of carbon gained to water lost).

The vast majority of water is lost from crops via transpiration and reducing this loss provides a potential route towards improving WUE and conserving soil water levels (Hepworth et al., 2015, New Phytologist 208: 336-341). To this end, much research into the use of anti-transpirants was carried out in 1960's and 70's (Davenport et al., 1972, Plant Physiology 49: 722-724). However, although effective in improving water status and increasing fruit size, these chemical solutions were never economically viable on an agricultural scale.

The majority of water loss from plants occurs via transpiration through epidermal pores known as stomata, making these cellular structures an attractive target in the battle to prevent water loss. Recently several laboratory studies have demonstrated that it is possible to improve drought tolerance and WUE by reducing the frequency of stomata on leaves; by using genetic manipulation or mutation to reduce stomatal density (SD) improved water use efficiency has been achieved across several model dicot species including *Arabidopsis* (Yoo et al., 2010, The Plant Cell Online 22: 4128-4141; Franks et al., 2015, New Phytologist 207: 188-195; Hepworth et al., 2015, New Phytologist 208: 336-341), poplar (Lawson et al., 2014, Genes & Genomics 36: 427-441) and tobacco (Yu et al., 2008, The Plant Cell 20: 1134-1151). In addition, the ectopic expression of a putative transcription factor in maize has led to reduced stomatal density and gas exchange in a monocot (Liu et al., 2015, Journal of Applied Genetics 56: 427-438).

The manipulation of SD has been facilitated by microscopic studies which characterised the cellular stages of the stomatal lineage, and molecular studies that revealed the developmental mechanisms controlling their progression (Zhao & Sack, 1999, Am J Bot 86: 929-939; Han & Torii, 2016, Development 143: 1259-1270). The majority of these studies have been carried out using the genetically tractable, model plant species *Arabidopsis*. During early *Arabidopsis* leaf development, a subset of epidermal cells known as meristemoid mother cells (MMCs) become primed to enter the stomatal lineage. Each MMC then undergoes an initial asymmetric entry division to produce a meristemoid in addition to a larger daughter cell known as a stomatal lineage ground cell (SLGC). SLGCs either differentiate directly into epidermal pavement cells or undergo further asymmetric divisions to produce secondary meristemoids. Some meristemoids can themselves undergo further asymmetric divisions, each of which reform a meristemoid and create an additional SLGC. Each meristemoid eventually differentiates into a guard mother cell, small and rounded in shape, prior to undergoing a symmetric division to form the guard cell pair of the mature stomatal complex. These cell fate transitions and divisions, which ultimately control the number and proportions of stomata and pavement cells in the mature leaf epidermis, are controlled by a sub-group of related basic helix-loop-helix (bHLH) transcription factors; SPCH, MUTE and FAMA (Ohashi-Ito & Bergmann, 2006, Plant Cell 18: 2493-2505; MacAlister et al., 2007, Nature 445: 537-540; Pillitteri & Torii, 2007, BioEssays 29: 861-870). SPCH primarily directs expression of genes controlling meristemoid formation including members of the cysteine-rich EPIDERMAL PATTERNING FACTOR (EPF) family of secreted signalling peptides, which in turn activate a pathway that regulates bHLH stability, thus forming a feedback loop that regulates the number of cells entering the stomatal lineage (Adrian et al. 2015, Dev Cell 33: 107-118; Simmons & Bergmann, 2016, Current Opinion in Plant Biology 29: 1-8). The best characterised negative regulators of stomatal density in this peptide family are EPF1 and EPF2, which are numbered in order of their discovery (Nara et al., 2007, Genes & Development 21: 1720-1725; Hara et al., 2009, Plant Cell Physiol 50: 1019-1031; Hunt & Gray, 2009, Curr Biol 19: 864-869). Both peptides act extracellularly within the aerial epidermal cell layer to suppress stomatal development through activation of an intracellular MAP kinase signalling pathway (Bergmann et al., 2004, Science 304:1494-1497; Wang et al., 2007 Plant Cell 19: 63-73; Lampard et al., 2008 Science 322:1113-1116). Although their functions somewhat overlap, EPF2 acts earliest in stomatal development to restrict entry of cells into the stomatal lineage, whilst EPF1 acts later to orient subsequent divisions of meristemoid cells and enforce stomatal spacing through the 'one-cell-spacing' rule (Nara et al., 2007, Genes & Development 21: 1720-1725). Manipulation of the expression levels of these peptides in *Arabidopsis* has led to significant improvements in drought tolerance and WUE in experiments conducted in controlled-environment plant growth rooms (Doheny-Adams et al., 2012, Philosophical Transactions of the Royal Society of London B: Biological Sciences 367: 547-555; Hepworth et al., 2015, New Phytologist 208: 336-341).

Grasses are an economically important plant group, with the cereal grasses being of critical importance for both food and energy production. Considering future predicted climate scenarios, the creation of drought tolerant cereal crops is a priority area for both crop improvement and scientific research. In contrast to the *Arabidopsis* model system, our knowledge of stomatal development in crops is relatively limited (Raissig et al., 2016, PNAS 113: 8326-8331). Although the grasses include many of our major global crops, our molecular understanding of their transpirational control mechanisms and more specifically regulation of stomatal development remains extremely limited.

Stomatal shape and patterning is markedly different between monocots and dicots such as *Arabidopsis*. It is known from microscopic observations that grass stomata are formed by a single asymmetric cell division that forms a stomatal precursor cell (a guard mother cell) and an epidermal pavement cell (Stebbins & Jain, 1960). There are no further asymmetric divisions of the stomatal lineage cells analogous to the repeated possible divisions that meristemoids undergo in *Arabidopsis* (Serna, 2011, Int J Dev Biol 55: 5-10). The mature grass stomatal complex is formed by division of two neighbouring cells that give rise to flanking subsidiary cells, and a symmetric division of the guard mother which produces two dumbbell-shaped guard cells—rather than the characteristically kidney-shaped guard cells of most dicots (Hetherington & Woodward, 2003, Nature 424: 901-908; Serna, 2011, Int J Dev Biol 55: 5-10). In contrast to dicots, all grass stomatal development initiates at the leaf base. The patterning of stomata within the leaf epidermis also differs in grasses, with stomata forming in straight files parallel to the leaf vein as opposed to the 'scattered' distribution seen in *Arabidopsis* (Stebbins & Khush, 1961, Variation in the organization of the stomatal complex in the leaf epidermis of monocotyledons and its bearing on their phylogeny. American Journal of Botany: 51-59; Geisler & Sack, 2002, New Phytologist 153: 469-476; Serna, 2011, Int J Dev Biol 55: 5-10).

The molecular network underpinning stomatal development in monocots is unclear. Furthermore, until now it was not known whether any EPFs function in controlling stomatal development in grasses. Recent work using genetic screens and targeted genome editing, has identified functional orthologs of genes encoding bHLH transcription factors involved in *Arabidopsis* stomatal development in grasses including; rice, maize (Liu et al., 2009, Development 136: 2265-2276) and *Brachypodium* (Raissig et al., 2016, PNAS 113: 8326-8331) and in the early diverging non-vascular mosses (Chater et al., 2016, Nature Plants 2: 16179). The identification of stomatal core bHLH transcription factors as master transcriptional regulators of stomatal initiation in the wheat relative *Brachypodium*, has led to these bHLH transcription factors being proposed as excellent breeding targets for enhancing performance in grasses.

Plant pathogens are also a major source of crop losses. Difficulties in monitoring and recording the precise causes of crop loss in some areas have contributed to a dearth of reliable global data on this, however, the available data indicate that direct losses due to disease, pests and weeds account for 20-40% of global agricultural productivity (Savary et al., 2012, Food Security DOI 10.1007/s12571-012-0200-5) in roughly equal proportions, with losses due to plant disease ranging from 10% of potential production in North America to 16% in Africa (Oerke et al., 1994, Crop production and crop protection: Estimated losses in major food and cash crops, ISBN: 978-0-444-82095-2). The largest losses in productivity are seen in monocot cereal crops, such as rice and wheat; key food global crops. Therefore, developing crops which are resistant to pathogens is also likely to be a key component of strategies aimed at improving the security of the global food supply.

SUMMARY OF THE INVENTION

The invention relates to the manipulation of EPF expression in order to modify the stomatal density of monocot plants. The invention is based on a discovery that EPF is involved in the suppression of stomatal development in plants, and particularly that EPF is involved in the suppression of stomatal development in monocot plants. The function of the gene, which is expressed at low levels during development of aerial tissues (IBSC 2012. International Barley Genome Sequencing Consortium: Nature Publishing Group. 711-716) remained unknown until now.

However, the inventors have surprisingly discovered that by manipulating the expression of EPF in monocot plants or plant material, they are able to modify the number of stomata per unit area (stomatal density). Despite the finely-balanced control of monocot leaf development, the inventors have shown that ectopic overexpression of EPF in transgenic monocot lines results in a reduced stomatal density. Advantageously, modified plants with increased levels of EPF exhibit improved WUE. This modification reduces water loss via transpiration from modified plants relative to carbon gain, which increases the efficiency of plant growth, and additionally results in a significant improvement in soil water level conservation.

Modified plants with increased levels of EPF also exhibit improved drought tolerance. Furthermore, the inventors have surprisingly discovered that ectopic overexpression of EPF in a monocot plant results in improved WUE and drought tolerance without deleterious effects on yield.

In a further surprising development, the inventors have discovered that overexpression of EPF in a monocot or dicot background results in plants (monocots and dicots) with an improved resistance to microbial pathogen infection.

By harnessing the control that EPF exerts over stomatal development, the present invention for the first time makes it feasible to readily modify the stomatal density of a monocot plant in order to improve the survival and growth of crops in challenging environments. Additionally, control over stomatal development allows plant architecture to be optimised for growth in specific environments, at specific developmental stages or in response to abiotic and/or biotic stresses. Extraordinarily, the inventors have found that manipulation of EPF allows resistance to these stress factors to be achieved without an associated yield detriment. The polypeptides, polynucleotides, expression vectors, methods, kits and compositions described herein find application as tools to modify stomatal density in a monocot plant background, and usefully in a cereal crop background, to achieve the aforementioned technical advantages.

Accordingly, in one aspect the invention provides a method of modifying stomatal density in a monocot plant, comprising modifying the presence, expression or activity in a monocot plant of Epidermal Patterning Factor (EPF) polypeptide.

The term "modifying the presence, expression or activity of EPF polypeptide" may refer to over-expression, suppression or temporal or spatial mis-expression of the levels of EPF polypeptide in a plant or plant material and/or elevation or reduction in the biological activity of the protein. This may be achieved by various standard techniques well known in the art.

Modification of the levels of EPF, in accordance with the present invention, may commonly mean an increase or decrease in the levels in the plant; preferably the levels localised in cells of the leaf tissue, more preferably in the cells of the leaf epidermal tissue of a plant, as compared to the levels in the same tissue in a native plant of the same species at the same stage if grown under identical conditions, and in which no deliberate alteration of expression levels has been made (i.e. an unmodified control plant). Preferably, the levels of EPF are increased. Accordingly, the levels of EPF may increase in the range 5% to 500% relative to genetically equivalent, but unmodified control plants; optionally in the range 10% to 250%, 20% to 200% or 25% to 100%.

In all embodiments of the invention where the expression, level or activity of EPF is increased (i.e. elevated or upregulated) relative to controls, the level or activity of EPF in modified plants or plant material may optionally be 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, optionally in the range 150% to 199%, 200% to 249%, 250%, to 299%, 300% to 349%, 350% to 399%, 400% to 449%, 450% to 499%, 500% to 599%, 600% to 699%, 700% to 799%, 800% to 899% or 900% to 1000% relative to that of one or more control values. Such a polypeptide or polynucleotide may be said to be over-expressed, which refers to the level of expression in a modified, transgenic, or transformed organism that exceeds levels of expression in normal or untransformed organisms. Ordinarily, a control value will be an equivalent value of a genetically equivalent, but unmodified control plant or equivalent material thereof. Such a control value may appropriately be calculated as a mean value of several control plants.

Alternatively, levels of EPF are decreased. The levels of EPF decrease may fall in the range 5% to 500% relative to genetically equivalent, but unmodified control plants; optionally the range 10% to 250%, 20% to 200% or 25% to 100%.

In all embodiments of the invention where the expression, level or activity of EPF is reduced (i.e. decreased or downregulated) relative to controls, the expression, level or activity of EPF in modified plants or plant material may optionally be 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% relative to that of one or more control values. Ordinarily, a control value will be an equivalent value of a genetically equivalent, but unmodified control plant or equivalent material thereof. Such a control value may appropriately be calculated as a mean value of several control plants.

Furthermore, the expression, level or activity of EPF may be assessed relative to one or more reference values. A reference value may be an 'internal' standard or range of internal standards, for example a known concentration of a protein, transcript, label or compound. Alternatively, the reference value may be an internal technical control for the calibration of expression values or to validate the quality of the sample or measurement techniques. This may involve a measurement of one or several proteins or transcripts within the sample which are known to be constitutively expressed or expressed at a known level. For example tubulin and GADPH may commonly be used as housekeeping reference genes. Accordingly, it would be routine for the skilled person to apply these known techniques alone or in combination in order to quantify the level of EPF in a sample relative to standards or other transcripts or proteins or in order to validate the quality of the biological sample, the assay or statistical analysis.

The invention is based on the use of an EPF polypeptide or functional fragment thereof, which may be defined both in terms of the following amino acid motifs, or in terms of the reference sequence SEQ ID NO: 6 and any percentage variant thereof, or alternatively in terms of the reference sequence SEQ ID NO: 8, and any percentage variant thereof, in combination with any of the amino acid motifs.

In preferred aspects of the invention, the EPF polypeptide comprises; the amino acid motif GSX$^1$X$^2$PDC [SEQ ID NO: 1], wherein X$^1$ is one of S or R and X$^2$ is one of L or I.

Optionally, the EPF polypeptide may comprise; the amino acid motif YRCMC [SEQ ID NO: 2].

Optionally, the EPF polypeptide may comprise; the amino acid motif HACGAC [SEQ ID NO: 3].

Optionally, the EPF polypeptide may comprise; the amino acid motif CPMVYRCMCKGKCYPVPS [SEQ ID NO: 4].

Optionally, the EPF polypeptide may comprise; the amino acid motif PCNRVMVSFKC [SEQ ID NO: 5]

Optionally, the EPF polypeptide may comprise; the amino acid sequence motif TGSSLPDCTHACGACK-PCNRVMVSFKCSIAEPCPMVYRCMCKGKCYPVPSS [SEQ ID NO: 6].

Optionally, the EPF polypeptide may comprise; the amino acid sequence motif EKKDGSGFLQEEVYGTGSSLPDCTHACGACK-PCNRVMVSFKCSIAEPCPMVYRC MCKGKCYPVPSS [SEQ ID NO: 7].

In addition to the aforementioned amino acid sequences, the invention may also be defined in terms of the reference sequence SEQ ID NO: 6 and a percentage variant thereof in terms of sequence identity, in combination with any of the aforementioned amino acid motifs. Alternatively, the invention may also be defined in terms of the reference sequence SEQ ID NO: 8 MKRHGLAARVHHVRPLLVLLAAVLL-LAATVDGIRPDPDDHARPGQAPGAPAVEEKK DGSGFLQEEVYGTGSSLPDCTHACGACK-PCNRVMVSFKCSIAEPCPMVYRCMCK GKCYPVPSS, and a percentage variant thereof in terms of sequence identity, in combination with any of the aforementioned amino acid motifs.

In preferred aspects, the polypeptide or a fragment thereof comprises an amino acid sequence of SEQ ID NO: 6 or a sequence of at least 62%; preferably at least 90%; more preferably at least 95%; even more preferably at least 98%.

Optionally, the EPF polypeptide may comprise; a sequence of SEQ ID NO: 8 or a sequence of at least 38% identity thereto. Optionally, the EPF polypeptide may comprise; the amino acid sequence of SEQ ID NO: 8 or a sequence of at least 60% identity thereto. Preferably, the EPF polypeptide comprises; a sequence of SEQ ID NO: 8 or a sequence of at least at least 90% identity thereto; more preferably at least 95%; even more preferably at least 98% identity thereto.

Optionally, the EPF polypeptide may comprise; the amino acid sequence of SEQ ID NO: 8 or a sequence of at least 60% identity thereto, preferably a sequence of at least 90% identity thereto, and comprises the amino acid sequence SEQ ID NO: 6 or a sequence of at least 62% identity thereto, preferably a sequence of at least 95% identity thereto.

Preferably, the EPF polypeptide comprises the amino acid sequence SEQ ID NO: 6 or a sequence of at least 95% identity thereto, and comprises the amino acid sequence SEQ ID NO: 8 or a sequence of at least 90% identity thereto.

In a preferred aspect of the invention, the EPF polypeptide comprises the amino acid sequence SEQ ID NO: 8 or a sequence of at least 90% identity thereto, and comprises any one of the amino acid motifs;

GSX$^1$X$^2$PDC [SEQ ID NO: 1], wherein X$^1$ is one of S or R and X$^2$ is one of L or I; or YRCMC [SEQ ID NO: 2]; or
HACGAC [SEQ ID NO: 3]; or
CPMVYRCMCKGKCYPVPS [SEQ ID NO: 4]; or
PCNRVMVSFKC [SEQ ID NO: 5]; or
TGSSLPDCTHACGACKPCNRVMVSFKCSIAE-PCPMVYRCMCKGKCYPVPSS [SEQ ID NO: 6]; or
EKKDGSGFLQEEVYGTGSSLPDCTHACGACK-PCNRVMVSFKCSIAEPCPMVYRC MCKGKCYPVPSS [SEQ ID NO: 7].

Preferably, the EPF polypeptide or fragment thereof comprises an amino acid sequence of SEQ ID NO: 8 or a sequence of at least 98% identity thereto.

Preferably, the EPF polypeptide may be encoded by a polynucleotide sequence comprising; a nucleotide sequence of SEQ ID NO: 14 or a sequence of at least 58% identity thereto. Preferably, the EPF polypeptide may be encoded by a polynucleotide sequence comprising; a nucleotide sequence of SEQ ID NO: 14 or a sequence of at least 58% identity thereto; more preferably at least 90% identity thereto; even more preferably 95% identity thereto; still more preferably at least 98% identity thereto.

Optionally, the EPF polypeptide may be encoded by a polynucleotide sequence comprising; SEQ ID NO: 9; or SEQ ID NO: 10; or SEQ ID NO: 11; or SEQ ID NO: 12; or SEQ ID NO: 13; or SEQ ID NO: 14; or SEQ ID NO: 15; or SEQ ID NO: 16.

The EPF polypeptide may be encoded by a polynucleotide sequence comprising; SEQ ID NO: 9; or a sequence of at least 67%; preferably at least 90%; more preferably at least 95%; even more preferably at least 98% identity thereto; or SEQ ID NO: 10; or a sequence of at least 67%; preferably at least 90%; more preferably at least 95%; even more preferably at least 98% identity thereto; or SEQ ID NO: 11; or a sequence of at least 59%; preferably at least 90%; more preferably at least 95%; even more preferably at least 98% identity thereto; or SEQ ID NO: 13; or a sequence of at least 66%; preferably at least 90%; more preferably at least 95%; even more preferably at least 98% identity thereto; or SEQ ID NO: 14; or a sequence of at least 58%; preferably at least 90%; more preferably at least 95%; even more preferably at least 98% identity thereto.

Polynucleotides encoding EPF, may be isolated nucleic acid molecules and may be RNA or DNA molecules. Throughout, the term "polynucleotide" as used herein refers to a deoxyribonucleotide or ribonucleotide polymer in single- or double-stranded form, or sense or anti-sense, and encompasses analogues of naturally occurring nucleotides that hybridize to nucleic acids in a manner similar to naturally occurring nucleotides. Such polynucleotides may be plant-, bacteria-, fungal- or virus derived, and preferably may be derived from the same species of plant as the plant being modulated to achieve optimal function of the sequences of interest in the recipient plant background and to reduce unwanted effects. In the case of polynucleotides encoding EPF, the polynucleotides may preferably be plant-derived, and especially from Barley, Wheat, Maize or Rice.

In all aspects of the invention, where there is a reference nucleic or amino acid sequence and sequences of at least a certain percentage identity are disclosed, e.g. 38%, then optionally the percentage identity may be different. For example: a percentage identity which is "at least" one of the following: 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or 100%. Such sequence identity with a EPF amino acid sequence, polypeptide sequence, polynucleotide sequence, gene, mRNA or cDNA from, e.g. *Hordeum vulgare*, is a function of the number of identical positions shared by the sequences in a selected comparison window, taking into account the number of gaps, and the length of each gap, which need to be introduced for optimal alignment of the two sequences.

The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet.

In all aspects of the invention, amino acid residues may be substituted conservatively or non-conservatively. Conservative amino acid substitutions refer to those where amino acid residues are substituted for other amino acid residues with similar chemical properties (e.g., charge or hydrophobicity) and therefore do not alter the functional properties of the resulting polypeptide. Similarly the person skilled in the art will appreciate that nucleic acid sequences may be substituted conservatively or non-conservatively without affecting the function of the polypeptide. Conservatively modified nucleic acids are those substituted for nucleic acids which encode identical or functionally identical variants of the amino acid sequences. Each codon in a nucleic acid (except AUG and UGG; typically the only codons for methionine or tryptophan, respectively) can be modified to yield a functionally identical molecule. Accordingly, each silent variation (i.e. synonymous codon) of a polynucleotide or polypeptide, which encodes a polypeptide of the present invention, is implicit in each described polypeptide sequence.

The invention provides a method of modifying stomatal density in a monocot plant, comprising modifying the presence, expression or activity in a monocot plant of Epidermal Patterning Factor (EPF) polypeptide, wherein the method comprises increasing the expression and/or level and/or activity of EPF polypeptide in cells of the plant or plant material compared to cells of an equivalent control plant or plant material. Advantageously, the resulting plant or plant material will have a reduced stomatal density compared to a genetically equivalent but unmodified plant or plant material. Preferably, the plant will have fewer stomata per unit area than an otherwise identical, control plant. For example the resulting plant may have fewer stomata per unit leaf area than an otherwise identical, control plant.

Throughout, a control plant will ordinarily be a genetically equivalent, but unmodified control plant or equivalent material thereof. In the case of control plants for polynucleotide transformation experiments, such a control plant may be transformed with an 'empty' vector or a vector sequence which lacks the polynucleotide of interest. Control values may appropriately be calculated as a mean value of several control plants.

Improved WUE and Drought Tolerance

The inventors have found that in addition to reduced stomatal density, modified plants of the invention which have increased expression, levels or activity of EPF compared with unmodified control plants, have improved WUE and tolerance of water limitation stress (drought) relative to those control plants. Although one might expect that increased WUE to be accompanied by a yield penalty, because of a reduced leaf gas exchange capacity and therefore a reduced capacity for carbon assimilation, the inventors have actually found that modified plants of the invention have higher or equal yields than unmodified plants when subjected to water stress. For the first time, this allows reduced stomatal density and increased plant WUE to be advantageously divorced from an associated reduction in yield. This overcomes a major limitation of previously available plants having improved WUE, where the restricted gaseous exchange capacity placed constraints on plant productivity. Advantageously, therefore the resulting plant or plant material may have increased water use efficiency (WUE) compared to an equivalent control plant or plant material.

Furthermore, methods of the invention improve drought tolerance in plants. The resulting plant or plant material has increased drought tolerance compared to an equivalent control plant or plant material. As with improved WUE, the inventors have discovered that increasing EPF expression allows reduced stomatal density and increased plant WUE to be decoupled from yield. Preferably, modification of any monocot plant in accordance with methods of the invention which results in increased expression, level and/or activity of EPF in the resultant plant or plant material results in a plant having increased yield compared with an unmodified control plant, when subjected to conditions of water stress. Conveniently, although drought tolerance in monocots is thought to be controlled by a number of genes, the present invention allows drought tolerance to be achieved by increasing the expression of a single gene. Drought, or water stress refers to a situation where less water is available than is demanded by the plant tissues. In this case, water stress refers to conditions that elicit a water stressed condition in a genetically equivalent but unmodified control plant. A plant may be considered water stressed if the growth, development, yield or fertility of an unmodified control plant is affected by a lack of water availability relative to demand. Water stress may be continuous or discontinuous. The magnitude or severity of the stress in a plant may vary over time or as between different species or individuals at a particular time point, for example in a field of crop plants.

Plant species vary substantially in their water requirements and therefore the soil water status at which they would be considered as being under drought stress. It will be understood that the amount of water available to the plant under "well-watered" conditions and "water-restricted" or "water limited" conditions will vary from species to species, and even within species depending on the water demands of the plant. For example in Barley, plant maintained under well-watered conditions refers to those maintained at a level of at least 60% maximum soil water content. However, monocot plants which typically occupy, are usually grown and/or are bred to be cultivated under higher levels of soil water content may be considered "water-restricted" or water-limited" under the same conditions. For instance, some wheat varieties may be considered water-stressed at a soil water status of below 70%. Furthermore, Rice, in particular paddy-grown Rice may be bred to be grown under conditions having a much higher soil water percentage value, e.g. 80% or 90%. Such stress or the severity of the stress may also be a function of the time period under which plants endure situation where water demand exceeds water availability as well as the degree of that deficit. A plant may be considered water stressed if the growth, development, yield or fertility of an unmodified control plant is affected by a lack of water availability relative to demand. This may be apparent for example as wilting of unmodified control plants or more dramatic effects such as for example, yellowing of leaves, stunted growth, reduced yield or seed set in unmodified control plants etc.

Yield may be measured in a number of ways and may refer to vegetative or reproductive parts of the plant, depending on the crop and whether biomass, leaf number, harvest index or seed number or seed size is desired. In preferred embodiments, the size and/or number of seeds or grain produced by a plant modified in accordance with a method of the invention is increased relative to unmodified control plants or plant material that has endured the water stressed condition. Most preferably, the size and number of seeds produced by plants modified in accordance with methods of the invention is increased relative to unmodified equivalent plants. Preferably the size and/or number of seeds or grain produced by a plant produced in accordance with the methods of the invention is increased relative to unmodified control plants or plant material that has endured the water stressed condition.

In accordance with all aspects of the present invention, the methods disclosed herein may be used to confer improved WUE and/or drought tolerance on any monocot plant species. The methods disclosed herein may preferably be used to modify those plants which are typically exploited for grain or biomass production, exhibit high growth rates and are easily grown and harvested. In particular, preferred plants include those which grow naturally or are cultivated in arid environments and/or those with high temperatures, low humidity, high vapour pressure deficits or receiving low quantities of water (rainfall and/or irrigation) relative to their water demand and water use efficiency (WUE). The methods disclosed herein may usefully prevent or alleviate water stress in plants whether severe, moderate, mild, continuous or intermittent. The methods disclosed herein may be used to produce monocot plants which are capable of experiencing and surviving severe water stress, which would have otherwise died if unmodified (i.e. which would result in the death of a genetically equivalent but unmodified control plant subjected to the same conditions).

Additionally, methods of the invention may be used to produce monocot plants which in addition to a reduction in SD, display greater tolerance of water-restricted regimes, for example when grown under conditions of 25% soil water content. Modified plants of the invention preferably show no reduction in grain yield when grown under water-restricted conditions compared with unmodified plants grown in well-watered conditions. Plant species vary substantially in their water requirements and therefore the soil water status at which they would be considered as being under drought stress. It will be understood that the amount of water available to the plant under "well-watered" conditions and "water-restricted" or "water limited" conditions will vary from species to species, and even within species depending on the water demands of the plant. For example in Barley, plant maintained under well-watered conditions refers to those maintained at a level of at least 60% maximum soil water content. However, monocot plants which typically occupy, are usually grown and/or are bred to be cultivated under higher levels of soil water content may be considered "water-restricted" or water-limited" under the same conditions. For instance, some wheat varieties may be considered water-stressed at a soil water status of below 70%. Furthermore, Rice, in particular paddy-grown Rice may be bred to be grown under conditions having a much higher soil water percentage value, e.g. 80% or 90%. Such stress or the severity of the stress may also be a function of the time period under which plants endure situation where water demand exceeds water availability as well as the degree of that deficit. A plant may be considered water stressed if the growth, development, yield or fertility of an unmodified control plant is affected by those conditions. Advantageously, modified plants of the invention preferably show no reduction in seed number, seed weight, average weight of seed, harvest index (the ratio of above ground biomass to seed weight), plant height, or above ground biomass under either well-watered or water-restricted conditions. In some embodiments, under water-restricted conditions, modified plants of the invention may have an increased seed number and yield compared with genetically equivalent, but unmodified control pants grown under well-watered conditions.

The improved drought tolerance of modified plants of the invention may be manifest in a reduced susceptibility to wilting compared with unmodified control plants. This may be obvious from simple observation of the plant phenotype after a period of water limitation. For example, after 6 days of water-withheld conditions, plants over-expressing EPF may be less susceptible to wilting and appear visibly more 'drought tolerant'.

Drought tolerance of modified plants of the invention may be manifest in a reduced soil water loss compared with unmodified control plants. A practical method of calculating soil water loss which is commonly used is measuring the weight of soil in which the plant is grown, for example by comparing the total weight of soil in pots of modified and unmodified control plants at least two time points. Modified plants of the invention may, for example, lose water more slowly than unmodified control plants. Further, modified plants of the invention may for example exhibit greater soil water conservation in their pots over a given period of time under water-withheld conditions, for example from day 2 until day 14 under water-withheld conditions.

Chlorophyll fluorescence measurements are routinely used to measure any reductions in photosystem II efficiency, an indicator of plant stress. In particular, the light adapted quantum yield of photosystem II ($\phi_{PSII}$) is measured daily for both well-watered and water-withheld plants throughout a terminal drought experiment. Modified plants of the invention may show no difference in photosystem II efficiency, as determined by light adapted quantum yield of photosystem II ($\phi_{PSII}$) as compared with unmodified control plants under well-watered conditions. Remarkably however, modified plants of the invention that have had water withheld, may display significantly enhanced rates of $\phi_{PSII}$ versus water-withheld unmodified control plants. Preferably, modified plants of the invention that have had water withheld, may maintain photosystem II efficiency for approximately 4 days longer than unmodified controls under severe drought conditions. Modified plants having up-regulated levels of expression or activity of EPF have an enhanced ability to retain water in their leaves under drought conditions. That is, higher levels of leaf relative water content (RWC) than unmodified controls under conditions of water limitation. More preferably, on day 6 of terminal drought, leaf relative water content (RWC) of leaf samples of plants having up-regulated levels of expression or activity of EPF, grown in water-withheld conditions, will display significantly higher levels of leaf RWC compared with unmodified controls grown in the same conditions.

Resistance to Pathogen Infection

Advantageously, the resulting plant or plant material may have increased resistance to infection by a microbial pathogen compared to an equivalent control plant or plant material. Preferably, the microbial pathogen is a bacterial or fungal pathogen. More preferably, the microbial pathogen is of the genus *Pseudomonas*, for example the microbial pathogen may be *Pseudomonas syringae*. Alternatively, the microbial pathogen may be a bacterial pathogen of the genus *Xanthomonas*, for example *Xanthomonas oryzae*. Alternatively, the microbial pathogen may be a fungal pathogen of the *Septoria* or *Puccinia* genus, for example *Zymoseptoria tritici* or *Puccinia hordei*.

Usefully, the resulting plant or plant material may have increased or equivalent yield compared to an equivalent control plant or plant material.

Plants with Increased Stomatal Density

The present invention also provides a method of modifying stomatal density in a monocot plant, comprising modifying the presence, expression or activity in a monocot plant of Epidermal Patterning Factor (EPF) polypeptide, wherein the method comprises reducing the expression and/or level and/or activity of EPF polypeptide in cells of the plant or plant material compared to cells of an equivalent control plant or plant material. Beneficially, the resulting plant or plant material has an increase in the stomatal density compared with a genetically equivalent but unmodified plant or plant material; that is to say a greater number of stomata per unit area than control plants or material, for example more stomata per unit leaf area compared to an equivalent control plant or plant material.

Advantageously, this increase in stomatal density in monocots, which has not been reported previously, can be achieved by reducing the expression, level or activity of a single protein; EPF.

Modified plants of the invention preferably show no reduction in grain yield compared with unmodified plants grown in identical conditions. Advantageously, modified plants of the invention preferably show no reduction in seed number, seed weight, average weight of seed, harvest index (the ratio of above ground biomass to seed weight), plant height, or above ground biomass compared with unmodified plants grown in identical conditions. In some embodiments, modified plants of the invention may have an increased seed number and yield compared with genetically equivalent, but unmodified control pants grown in identical conditions.

The invention also provides a method of modifying stomatal density in a monocot plant, comprising modifying the expression, level or activity in a monocot plant of Epidermal Patterning Factor (EPF) polypeptide, wherein the method comprises transforming a plant or plant material with a polynucleotide comprising a polynucleotide sequence of;

SEQ ID NO: 9; or a sequence of at least 67%; preferably at least 90%; more preferably at least 95%; even more preferably at least 98% identity thereto; or SEQ ID NO: 10; or a sequence of at least 67%; preferably at least 90%; more preferably at least 95%; even more preferably at least 98% identity thereto; or SEQ ID NO: 11; or a sequence of at least 59%; preferably at least 90%; more preferably at least 95%; even more preferably at least 98% identity thereto; or SEQ ID NO: 13; or a sequence of at least 66%; preferably at least 90%; more preferably at least 95%; even more preferably at least 98% identity thereto; or SEQ ID NO: 14; or a sequence of at least 58%; preferably at least 90%; more preferably at least 95%; even more preferably at least 98% identity thereto; or a functional fragment thereof; wherein expression of said polynucleotide in cells of the plant or plant material results in an increase in the expression and/or level and/or activity of EPF polypeptide in said cells compared to untransformed cells; and a reduction in the stomatal density of the plant or plant material compared to an equivalent untransformed plant or plant material.

Preferably, the expression or level of any of the above polynucleotides is increased in one or more cells of the recipient plant relative to an unmodified control plant. Suitably, any of the above polynucleotides may be placed under the control of one or more regulatory elements which result in a high level of EPF expression in the recipient plant, plant material or plant cell relative to EPF expression in an unmodified control plant, plant material or plant cell.

The practical utility of the invention lies in the ability to use EPF as a master switch for stomatal development. Therefore in most applications of the invention, it will be sufficient to vary the expression, level or activity of EPF alone, according to the desired application, for example by increasing the level of expression for improved WUE, drought tolerance and resistance to microbial pathogen infection or reducing EPF expression to increase stomatal density. Similarly, it will often be sufficient to vary the degree of EPF up-regulation or down-regulation alone in order to achieve the desired level of stomatal density to suit the plant growth conditions, or for example to tune this to changing environmental conditions by placing the EPF under the control of promoters, the expression of which is environmentally determined. One example of this might be placing EPF expression under the control of a drought-sensitive promoter or regulatory element, such that the drought-tolerance of the plant is matched to changing external water status.

However, whilst in preferred embodiments, EPF may be either up-regulated (over-expressed) or down-regulated (suppressed) in the cells of a plant, in order to operate as a simple 'off'/'on' switch governing stomatal development, and therefore stomatal density in the tissues of a recipient plant, it is envisaged that it may in certain circumstances be desirable to also down-regulate EPF in certain tissues, whilst up-regulating EPF in other tissues, in order to differentially control the number or density of stomata in different locations in the plant, or to up- or-down-regulate EPF at different developmental stages or in response to different environmental conditions. This may for example be appropriate if changes in WUE, drought tolerance or resistance to pathogen infection are required at different developmental stages or in response to different environmental conditions.

Stringent Conditions

In the polynucleotide sequences for use in accordance with the invention, the nucleotide sequence may be that which encodes the respective SEQ ID NOs: 8, 9, 10, 11, 12, 13, 14, 15, or 16 or in defining the range of variant sequences thereto, or in defining sequences which may be used to mediate an alteration in the expression of one of said polynucleotides, it may be defined instead as a sequence hybridizable to the reference nucleotide sequence, preferably under stringent conditions, more preferably very high stringency conditions. The term "stringent conditions" may be understood to describe a set of conditions for hybridization and washing and a variety of stringent hybridization conditions will be familiar to the skilled reader. Hybridization of a nucleic acid molecule occurs when two complementary nucleic acid molecules undergo an amount of hydrogen bonding to each other known as Watson-Crick base pairing. The stringency of hybridization can vary according to the environmental (i.e. chemical/physical/biological) conditions surrounding the nucleic acids, temperature, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, New York, 1993). The Tm is the temperature at which 50% of a given strand of a nucleic acid molecule is hybridized to its complementary strand.

In any of the references herein to hybridization conditions, the following are exemplary and not limiting:

Very High Stringency (allows sequences that share at least 90% identity to hybridize)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (allows sequences that share at least 80% identity to hybridize)

Hybridization: 5×-6×SSC at 65° C.-70° C. for 16-20 hours

Wash twice: 2×SSC at RT for 5-20 minutes each

Wash twice: 1×SSC at 55° C.-70° C. for 30 minutes each

Low Stringency (allows sequences that share at least 50% identity to hybridize)

Hybridization: 6×SSC at RT to 55° C. for 16-20 hours

Wash at least twice: 2×-3×SSC at RT to 55° C. for 20-30 minutes each.

In an alternative aspect, the present invention also provides a method of modifying stomatal density in a monocot plant, comprising modifying the presence, expression or activity in a monocot plant of Epidermal Patterning Factor (EPF) polypeptide, wherein cells of the plant or plant material are transformed with a polynucleotide comprising a polynucleotide sequence capable of hybridizing to a polynucleotide sequence of SEQ ID NO: 9, SEQ ID NO: 10, SEQ ID NO: 11, SEQ ID NO: 13, or SEQ ID NO: 14 under stringent conditions, such that there is reduction in, or elimination of, the expression and/or level of native EPF polypeptide and/or activity thereof in such cells compared to untransformed cells; and wherein the stomatal density of the plant or plant material is increased compared to an unmodified or untransformed plant or plant material.

In accordance with the present invention, such polynucleotides will be complementary, i.e. in an antisense orientation to a polynucleotide sequence of SEQ ID NO: 9, SEQ ID NO: 10, SEQ ID NO: 11, SEQ ID NO: 12, SEQ ID NO: 13 or SEQ ID NO: 14, and which are capable of specifically hybridizing under stringent conditions to the above polynucleotide sequences. Such sequences may be useful in down-regulating expression of EPF in order to obtain an increased stomatal density compared to a genetically equivalent but unmodified control plant.

A number of technologies may be used to down-regulate, reduce, or eliminate the expression and/or level of native EPF polypeptide and/or activity thereof in order to obtain an increased stomatal density compared to a genetically equivalent but unmodified control plant. Such technologies may include, but are not limited to; mutation (insertion, deletion, substitution) of the genomic DNA sequence, RNAi, microRNA (MiRNA), using a catalytically inactive Cas9 (dCas9) repressor fusion and genome editing systems such as Zinc Finger Nucleases, TALEN, Cas9 or Cpf1. For instance the CRISPR-Cas system allows target-specific cleavage of genomic DNA guided by Cas9 nuclease in complex with a guide RNA (gRNA) that complementarily binds to a 20 nt targeted sequence. Alteration of the sequence of the gRNA guide therefore allows the Cas9 endonuclease to be programmed to cut double-stranded DNA at sites complementary to the 20-base-pair guide RNA. The Cas9 system has been used to modify genomes in multiple cells and organisms.

Accordingly, where the genomic DNA encoding EPF (e.g. SEQ ID NO: 13; SEQ ID NO: 14) or mRNA transcript (SEQ ID NO: 9) is to be edited, for example using an endonuclease, a guide RNA comprising a sequence substantially complementary to a sequence comprised in a target nucleic acid strand may be provided to a plant cell where the sequence is to be edited, such that the sequence may be edited in a sequence specific manner. For example the polynucleotide sequence capable of hybridizing to a polynucleotide sequence of SEQ ID NO: 9; SEQ ID NO: 10, SEQ ID NO: 11, SEQ ID NO: 13, or SEQ ID NO: 14 may be a guide RNA.

Editing of the above sequences may be used in order to achieve an increase in stomatal density, by reducing the expression and/or level and/or activity of EPF in one or more recipient plant cells compared to unedited or untransformed cells. Suitably, the stomatal density of the plant or plant material is increased compared to an untransformed plant or plant material.

Accordingly, in any of the methods where plants or plant material are transformed with a polynucleotide disclosed herein, the plant or plant material may be stably transformed with said polynucleotide.

Accordingly, in any of the methods where plants or plant material are transformed with a polynucleotide disclosed herein, the plant or plant material may be transformed with a multiplicity of said polynucleotides.

In a further aspect, the present invention also provides a method of modifying a plant or plant material to impart at least partial resistance to, or improve resistance to infection by a microbial pathogen, wherein the method comprises increasing the expression and/or level and/or activity of EPF polypeptide in cells of the plant or plant material compared to cells of an equivalent control plant or plant material; wherein the EPF polypeptide comprises a sequence of SEQ ID NO: 8 or a sequence of at least 60% identity thereto. Preferably, the EPF polypeptide comprises a sequence of SEQ ID NO: 8 or a sequence of at least 90% identity thereto.

Plants with Improved Pathogen Resistance

The methods, polypeptides, polynucleotides and expression vectors of the invention may be used to impart at least partial or improved microbial resistance in plants. Modified plants, plant material or plant parts with improved resistance to infection by a microbial pathogen or partial resistance to infection by a microbial pathogen may be generated by increasing the expression and/or level and/or activity of EPF alone. Plants or plant material modified in this way will have reduced stomatal density compared with otherwise identical unmodified or untransformed plants or plant material.

Modified plants engineered to over-express EPF or to have increased activity of EPF, having improved microbial resistance may be generated for example by genetic modification, genetic transformation, gene editing or marker assisted breeding and refer to plants which are better able to resist infection by a microbial pathogen, particularly a bacterial pathogen, and more particularly a *Pseudomonas* pathogen, than otherwise identical equivalent control plants. In particular, where the host plant is Rice, and the microbial pathogen is a bacterial pathogen, the modified rice plant may have partial or improved resistance to infection by *Xanthomonas oryzae* compared with unmodified control rice plants. Such modified plants may survive or tolerate microbial infection where otherwise identical equivalent control plants would not. It will be understood that such a microbial infection may comprise more than one species of bacteria, including for example *Pseudomonas* or *Xanthomonas*. Similarly, where the microbial pathogen is a fungal pathogen, such a microbial infection may comprise more than one fungal species or isolate, including for example *Puccinia* or *Septoria*, e.g. a *Zymoseptoria tritici* infection in Wheat. In particular, where the host plant is Wheat, and the microbial pathogen is a fungal pathogen, the modified Wheat plant may have partial or improved resistance to infection by *Zymoseptoria tritici* compared with unmodified control Wheat plants. In particular, where the host plant is Barley, and the microbial pathogen is a fungal pathogen, the modified Barley plant may have partial or improved resistance to infection by *Puccinia hordei* compared with unmodified control Barley plants.

Improved microbial pathogen resistance may refer to a greater resistance to infection by a bacterium, or tolerance of a bacterial infection, relative to unmodified or untransformed plants, plant parts or plant material. This improvement in resistance may be manifested in fewer colony forming units (CFUs) of the bacterium, e.g. *Xanthomonas oryzae* or *Pseudomonas syringae* present on the modified or transformed plant, plant part or plant material (e.g. leaves) per unit area compared with an unmodified or untransformed plant, plant part or plant material. This may also be manifested in reduced necrosis of plant tissues (e.g. leaves or floral organs), greater life span, or increased yield compared with unmodified or untransformed plants, plant parts or plant material. Plants may also demonstrate increased yield compared with equivalent control plants under conditions of pathogen infection or under conditions which would otherwise cause pathogen infection in otherwise identical equivalent control plants, which may manifest itself, for example, as increases in biomass relative to equivalent control plants and/or increases in the number, size and/or quality of seed produced by the plants relative to equivalent control plants or plant material.

Plants, plant material or plant parts with improved resistance to infection by a microbial pathogen, whether generated by e.g. genetic modification, genetic transformation, gene editing or marker assisted breeding may refer to plants which are able to resist infection by, or survive infection by *Pseudomonas* isolates, where otherwise identical equivalent control plants would not. Plants, plant material or plant parts with improved resistance to infection by a microbial pathogen may refer to plants which are able to resist or survive infection by *Pseudomonas* isolates, for instance *Pseudomonas syringae* isolates, where otherwise identical equivalent control plants would not. Plants, plant material or plant parts with improved resistance to infection by a microbial pathogen, whether generated by e.g. genetic modification, genetic transformation, gene editing or marker assisted breeding may refer to plants which are able to resist infection by, or survive infection by *Xanthomonas* isolates, for example *Xanthomonas oryzae* isolates, where otherwise identical equivalent control plants would not. Plants, plant material or plant parts with improved resistance to infection by a microbial pathogen, whether generated by e.g. genetic modification, genetic transformation, gene editing or marker assisted breeding may refer to plants which are able to resist infection by, or survive infection by *Septoria* isolates, for example *Zymoseptoria tritici* isolates, where otherwise identical equivalent control plants would not. Plants, plant material or plant parts with improved resistance to infection by a microbial pathogen, whether generated by e.g. genetic modification, genetic transformation, gene editing or marker assisted breeding may refer to plants which are able to resist infection by, or survive infection by *Puccinia* isolates, for example *Puccinia hordei* isolates, where otherwise identical equivalent control plants would not.

Plants may also demonstrate increased yield compared with equivalent control plants under conditions of pathogen infection which may manifest itself, for example, as increases in biomass relative to equivalent control plants and/or increases in the number, size and/or quality of seed produced by the plants relative to equivalent control plants or plant material.

A transformed or transgenic plant of the invention includes plants, for example, a plant the cells of which express a polynucleotide of the invention or have an expression cassette of the invention, i.e., an expression cassette comprising a polynucleotide of the invention, which plant may also have increased yields, and/or quality compared with a corresponding wild-type plant, for example under conditions of bacterial infection or conditions which would normally bring about a bacterial infection, particularly a *Pseudomonas* or *Xanthomonas* infection in an equivalent, unmodified control plant.

In order to further enhance the resistance of plants of the invention to microbial infection a person skilled in the art would recognise that it may be advantageous to incorporate or "stack" or "pyramid" two or more different polynucleotides as defined herein into a recipient plant. The number of stacked polynucleotides genes may typically be two or more, up to any acceptable number tolerable by the recipient plant. Additionally, it will be understood that polynucleotides as defined herein may be stacked with other polynucleotides which are capable of conferring resistance to microbial pathogens, whether of *Pseudomonas syringae* or *Puccinia hordei*, or any other species.

Such a method of modifying a plant or plant material to impart at least partial resistance to, or improve resistance to infection by a microbial pathogen, requires an increase in the expression and/or level and/or activity of EPF in the host plant.

Accordingly, such a method of modifying a plant or plant material to impart at least partial resistance to, or improve resistance to infection by a microbial pathogen, may suitably comprise transforming the plant, plant part or a plant cell with a polynucleotide comprising a polynucleotide sequence of;

SEQ ID NO: 9; or a sequence of at least 67%; preferably at least 90%; more preferably at least 95%; even more preferably at least 98% identity thereto; or SEQ ID NO: 10; or a sequence of at least 67%; preferably at least 90%; more preferably at least 95%; even more preferably at least 98% identity thereto; or SEQ ID NO: 11; or a sequence of at least 59%; preferably at least 90%; more preferably at least 95%; even more preferably at least 98% identity thereto; or SEQ ID NO: 13; or a sequence of at least 66%; preferably at least 90%; more preferably at least 95%; even more preferably at least 98% identity thereto; or SEQ ID NO: 14; or a sequence of at least 58%; preferably at least 90%; more preferably at least 95%; even more preferably at least 98% identity thereto;

or a functional fragment thereof; wherein expression of said polynucleotide in cells of the plant or plant material results in an increase in the expression and/or level and/or activity of EPF polypeptide in said cells compared to untransformed control cells;

wherein the EPF polypeptide comprises a sequence of SEQ ID NO: 8 or a sequence of at least 60% identity thereto.

Preferably, the expression or level of any of the above polynucleotides is increased in one or more cells of the recipient plant relative to an unmodified control plant. Suitably, any of the above polynucleotides may be placed under the control of one or more regulatory elements which result in a high level of EPF expression in the recipient plant, plant material or plant cell relative to EPF expression in an unmodified control plant, plant material or plant cell.

In contrast to other aspects of the invention disclosed herein, which are restricted in their application to monocot plants, aspects of the invention which relate to methods of modifying a plant or plant material to impart at least partial resistance to, or improve resistance to infection by a microbial pathogen, wherein the method comprises increasing the expression and/or level and/or activity of EPF polypeptide in cells of the plant or plant material compared to cells of an equivalent control plant or plant material; are applicable to both monocot and dicot plants. Although in preferred aspects, the plant is a monocot plant, and preferably the plant is of, or the plant material is derived from a plant selected from the genera *Hordeum* L., *Triticum* L., *Oryza* L., or *Zea* L., increases in the expression level and/or activity of EPF improve resistance to microbial pathogens in both monocot and dicot host backgrounds compared to an equivalent unmodified or untransformed control plant or plant material. Therefore, methods of improving resistance to pathogen infection disclosed herein are applicable to any plant species, which may be used as a host system for mis-expression or over-expression of EPF. Accordingly, in addition to the monocot host species disclosed herein, suitable host plants may include, but are not limited to; for example, tobacco (*Nicotiana tabacum*), potato (*Solanum tuberosum*), tomato (*Solanum lycopersicum*) or *Arabidopsis*. Typically, the plant may be a *Hordeum vulgare* L. plant or the plant material may be derived from a *Hordeum vulgare* L. plant. Similarly, the plant may be a *Triticum aestivum* L. plant or the plant material may be derived from a *Triticum aestivum* L. plant. Equally, the plant may be an *Oryza sativa* L. plant or the plant material may be derived from an *Oryza sativa* L. plant. Alternatively, the plant may be a *Zea mays* L. plant or the plant material may be derived from a *Zea mays* L. plant. The plant may be an *Arabidopsis thaliana* L. plant or the plant material may be derived from an *Arabidopsis thaliana* L. plant.

In a further aspect, the present invention also provides a method of modifying a plant or plant material to improve drought tolerance, wherein the method comprises increasing the expression and/or level and/or activity of EPF polypeptide in cells of the plant or plant material compared to cells of an equivalent control plant or plant material; wherein the EPF polypeptide comprises a sequence of SEQ ID NO: 8 or a sequence of at least 60% identity thereto.

In a further aspect, the present invention also provides a method of modifying a monocot plant or plant material to improve drought tolerance, comprising transforming the plant, plant part or a plant cell with a polynucleotide comprising a polynucleotide sequence of;

SEQ ID NO: 9; or a sequence of at least 67%; preferably at least 90%; more preferably at least 95%; even more preferably at least 98% identity thereto; or SEQ ID NO: 10; or a sequence of at least 67%; preferably at least 90%; more preferably at least 95%; even more preferably at least 98% identity thereto; or SEQ ID NO: 11; or a sequence of at least 59%; preferably at least 90%; more preferably at least 95%; even more preferably at least 98% identity thereto; or SEQ ID NO: 13; or a sequence of at least 66%; preferably at least 90%; more preferably at least 95%; even more preferably at least 98% identity thereto; or SEQ ID NO: 14; or a sequence of at least 58%; preferably at least 90%; more preferably at least 95%; even more preferably at least 98% identity thereto;

or a functional fragment thereof; wherein expression of said polynucleotide in cells of the plant or plant material results in an increase in the expression and/or level and/or activity of EPF polypeptide in said cells compared to untransformed control cells; wherein the EPF polypeptide comprises a sequence of SEQ ID NO: 8 or a sequence of at least 60% identity thereto.

Preferably, the present invention also provides a method of modifying a plant or plant material to improve drought tolerance, comprising transforming the plant, plant part or a plant cell with a polynucleotide comprising a polynucleotide sequence of; SEQ ID NO: 9; SEQ ID NO: 10, SEQ ID NO: 11, SEQ ID NO: 12; SEQ ID NO: 13, SEQ ID NO: 14, SEQ ID NO: 15 or, SEQ ID NO: 16 or a sequence of at least 90% identity therewith; or a functional fragment thereof; wherein expression of said polynucleotide in cells of the plant or plant material results in an increase in the expression and/or level and/or activity of EPF polypeptide in said cells compared to untransformed control cells; wherein the EPF polypeptide comprises a sequence of SEQ ID NO: 8 or a sequence of at least 60% identity thereto.

It will be understood that in accordance with the invention it is possible to obtain modified plants with increased stomatal density by reducing the expression, level and/or activity of EPF in the cells of the plant relative to those of a control plant. Although this can be achieved in a number of ways, for example by reducing transcript accumulation by RNAi or miRNA, it will be appreciated that one of the ways in which this could be achieved would be to introduce mutations, insertions, deletions and/or substitutions of one or more nucleotides in the sequence coding for—, or regulating expression of—, EPF, such that the expression product of the native gene does not produce transcript, is rendered non-functional or less active in the modified plant compared with an unmodified plant. Accordingly, in another aspect, the present invention provides a modified monocot plant or monocot plant material comprising cells whose genomic DNA does not form a contiguous nucleotide sequence of SEQ ID NO: 13 or a sequence of at least 66% identity therewith, or SEQ ID NO: 14 or a sequence of at least 58% identity therewith, wherein the plant or plant material has an increased stomatal density compared to genetically equivalent but unmodified plant or plant material having contiguous said nucleotide sequences.

Non-contiguous nucleotide sequences of SEQ ID NO: 13 or a sequence of at least 66% identity therewith, or SEQ ID NO: 14 or a sequence of at least 58% identity therewith, may disrupt the biological activity, structure, characteristics of the expression product, the rate of expression or the manner of expression control. Such modifications may be achieved by a variety of standard techniques well known in the art, and may include, but are not limited to introducing mutations, insertions, deletions and substitutions of one or more nucleotides, for example by DNA editing or classical mutagenesis.

One of the methods by which this can be achieved in the modified plant is by the application of DNA editing techniques, which are well understood and routine in the art. Accordingly, the present invention provides a method of increasing stomatal density in a monocot plant or monocot plant material, comprising editing one or more nucleotide residues of SEQ ID NO: 13 or a sequence of at least 66% identity therewith, or SEQ ID NO: 14 or a sequence of at least 58% identity therewith and which is comprised in the genome of the plant, such that the edited cells of the resulting plant or plant material have a reduction in, or elimination of, the expression and/or level of native EPF polypeptide and/or activity thereof in said cells compared to genetically equivalent but unedited cells of a control plant or plant material; wherein the EPF polypeptide comprises a sequence of SEQ ID NO: 8 or a sequence of at least 60% identity thereto. Preferably, said one or more nucleotide residues is/are edited such that the resultant EPF polypeptide is non-functional.

The present invention provides a monocot plant or monocot plant material transformed with a polynucleotide comprising any of;

SEQ ID NO: 9; or a sequence of at least 67%; preferably at least 90%; more preferably at least 95%; even more preferably at least 98% identity thereto; or SEQ ID NO: 10; or a sequence of at least 67%; preferably at least 90%; more preferably at least 95%; even more preferably at least 98% identity thereto; or SEQ ID NO: 11; or a sequence of at least 59%; preferably at least 90%; more preferably at least 95%; even more preferably at least 98% identity thereto; or SEQ ID NO: 13; or a sequence of at least 66%; preferably at least 90%; more preferably at least 95%; even more preferably at least 98% identity thereto; or SEQ ID NO: 14; or a sequence of at least 58%; preferably at least 90%; more preferably at least 95%; even more preferably at least 98% identity thereto;

or a functional fragment thereof, wherein expression of said polynucleotide in cells of the plant or plant material results in an increase in the expression and/or level and/or activity of EPF polypeptide in said cells compared to untransformed cells; wherein the EPF polypeptide comprises a sequence of SEQ ID NO: 8 or a sequence of at least 60% identity thereto. Preferably, said plant or plant material has reduced stomatal density compared to an equivalent untransformed plant or plant material.

Beneficially, said monocot plant or plant material has improved WUE, improved drought tolerance and improved resistance to pathogen infection compared with an untransformed control plant.

Alternatively, the present invention provides a monocot plant or monocot plant material, wherein the plant or plant material is transformed with a polynucleotide capable of specifically hybridizing to a polynucleotide comprising any of SEQ ID NO: 9, SEQ ID NO: 10, SEQ ID NO: 11, SEQ ID NO: 13, and/or SEQ ID NO: 14, under stringent conditions; wherein expression of said polynucleotide in cells of the plant or plant material results in a reduction in, or elimination of, the expression and/or level of native EPF polypeptide and/or activity thereof in such cells compared to untransformed cells; wherein the EPF polypeptide comprises a sequence of SEQ ID NO: 8 or a sequence of at least 60% identity thereto. Preferably, said plant or plant material has increased stomatal density compared to an equivalent untransformed plant or plant material.

A modified monocot plant or monocot plant material as disclosed herein, may have a polynucleotide of SEQ ID NO: 10 or a sequence of at least 67% identity thereto, or a polynucleotide of SEQ ID NO: 11 or a sequence of at least 59% identity thereto, or a polynucleotide of SEQ ID NO: 14 or a sequence of at least 58% identity thereto stably incorporated into its genome. Alternatively, said polynucleotide may be transiently expressed in the plant background. Furthermore, modified monocot plant or monocot plant material as disclosed herein, may be transformed with a multiplicity of said polynucleotides, whether stably, transiently or a combination of both.

The invention also provides a monocot plant or monocot plant material wherein the plant or plant material has increased expression, level or activity of EPF compared with an unmodified control plant, and wherein said plant or plant material has improved water use efficiency compared to an equivalent untransformed plant or plant material.

The invention also provides a monocot plant or monocot plant material wherein the plant or plant material has increased expression, level or activity of EPF compared with an unmodified control plant, wherein said plant or plant material has improved drought tolerance compared to an equivalent untransformed plant or plant material.

The invention also provides a monocot plant or monocot plant material wherein the plant or plant material has increased expression, level or activity of EPF compared with an unmodified control plant, wherein said plant or plant material has improved resistance to a microbial pathogen compared to an equivalent untransformed plant or plant material. Optionally the microbial pathogen may be a fungal pathogen, for example a *Septoria* or a *Puccinia* pathogen. Preferably, the pathogen is a bacterial pathogen. More preferably, the pathogen is of the genus *Pseudomonas*. Even more preferably the pathogen is *Pseudomonas syringae*.

In other embodiments, preferably the pathogen is a fungal pathogen. More preferably the pathogen is of the genus *Puccinia*. Even more preferably the pathogen is *Puccinia hordei*.

Modifying Presence, Expression or Activity of EPF

Modulating the levels or activity of a polypeptide encoded by a nucleic acid molecule may be achieved by various means. For example, elevating or reducing mRNA levels encoding said polypeptide by placing the nucleotide under the control of a strong promoter sequence or altering the gene dosage by providing a cell with multiple copies of said gene or its complement. Alternatively, the stability of the mRNA encoding said polypeptide may be modulated to alter the steady state levels of an mRNA molecule, this is preferably achieved via alteration to the 5' or 3' untranslated regions of the mRNA. Similarly, the production of a polypeptide may be modified by altering the efficiency of translational processing, increasing or decreasing protein stability or by altering the rate of post translational modification (e.g. proteolytic cleavage) or secretion.

Commonly, where a plant naturally expresses said EPF, modification of EPF expression may be achieved by altering the expression pattern of the native gene(s) and/or the processing and/or production of the polypeptide. This may be achieved by any suitable method, including, but not limited to altering transcription of the gene, and/or translation of the mRNA into polypeptide, and post-translational modification of the polypeptide. Altering the expression pattern of a native gene may be achieved by placing it under control of a heterologous regulatory sequence, which is capable of directing the desired expression pattern of the gene. Suitable regulatory sequences may be placed 5' and/or 3' of the endogenous gene and may include, but are not limited to promoter sequences, terminator fragments, polyadenylation sequences or enhancer sequences (e.g. VP16 transactivation domain) operably linked to the sequences of interest.

Alteration, whether activation or repression of the expression pattern of the native EPF gene(s) and/or the processing and/or production of the polypeptide(s) may also be achieved by using CRISPR-Cas technology, for example, by providing a catalytically inactive Cas9 (dCas9) fusion to synthetically repress or activate expression of EPF. In both approaches, a single guide RNA (sgRNA) may be designed to direct the dCas9 repressor or activator to a chosen genomic location, i.e. a genomic sequence specific to EPF. Potential target locations include promoter regions, regulatory regions, and early coding regions. To achieve transcriptional repression, dCas9 can be used by itself (repressing transcription through steric hindrance) or as part of a dCas9-KRAB transcriptional repressor fusion protein. Alternatively, transcriptional activation of EPF can be achieved by various approaches, for instance using the VP64 transcriptional activator. One approach is a dCas9-VP64 fusion protein. Another, aimed at signal amplification, requires fusion of dCas9 to a repeating array of peptide epitopes, which modularly recruit multiple copies of single-chain variable fragment (ScFv) antibodies fused to transcriptional activation domains. A further approach is a dCas9-VP64 fusion protein together with a modified sgRNA scaffold with an MS2 RNA motif loop. This MS2 RNA loop recruits MS2 coat protein (MCP) fused to additional activators such as p65 and heat shock factor 1 (HSF1). In this way, expression of EPF can be elevated or knocked-down as desired. A number of plasmids which are designed to be manipulated for the purpose are freely available from plasmid repositories, such as https://www.addgene.org/crispr/.

Plant Transformation

Plants transformed with a polynucleotide or expression construct of the invention may be produced by standard techniques for the genetic manipulation of plants which are known in the art. DNA may be introduced into plant cells using any suitable technology, such as gene transfer via a disarmed Ti-plasmid vector carried by *Agrobacterium tumefaciens*, using *Agrobacterium* sp.-mediated transformation, vacuum infiltration, floral dip, spraying, particle or microprojectile bombardment, protoplast transformation, electroporation, microinjection, electrophoresis, pollen-tube pathway, silicon carbide- or liposome-mediated transformation, uptake by the roots, direct injection into the xylem or phloem or other forms of direct DNA uptake. Microprojectile bombardment, electroporation and direct DNA uptake are preferred where *Agrobacterium* is inefficient or ineffective. Alternatively, a combination of different techniques may be employed to enhance the efficiency of the transformation process, e.g. bombardment with *Agrobacterium*-coated microparticles or microprojectile bombardment to induce wounding followed by co-cultivation with *Agrobacterium*.

Preferably, polynucleotides encoding EPF may be directly introduced into cells of cereal plants using microprojectile bombardment. Preferably, cereal transformation using microprojectile bombardment will include the acceleration of gold particles, coated with plasmid DNA (e.g. pBRACT214 gateway vector) comprising EPF genomic (SEQ ID NO: 14) or cDNA (SEQ ID NO: 11) polynucleotide sequences and one or more regulatory sequences (e.g. the maize ubiquitin promoter).

According to the present invention, whole plants, plant material or plant parts may be stably or transiently transformed as desired, wherein stable transformation refers to polynucleotides which become incorporated into the plant host chromosomes such that the host genetic material may be permanently and heritably altered and the transformed cell may continue to express traits caused by this genetic material, even after several generations of cell divisions. Transiently transformed plant cells refer to cells which contain heterologous DNA or RNA, and are capable of expressing the trait conferred by the heterologous genetic material, without having fully incorporated that genetic material into the cell's DNA. Heterologous genetic material may be incorporated into nuclear or plastid (chloroplastic or mitochondrial) genomes as required to suit the application of the invention. Where plants are transformed with more than one polynucleotide it is envisaged that combinations of stable and transient transformations are possible.

Polypeptide and Polynucleotide Sequences

The polypeptide sequences and polynucleotides used in the present invention may be isolated or purified. By "purified" is meant that they are substantially free from other cellular components or material, or culture medium. "Isolated" means that they may also be free of naturally occurring sequences which flank the native sequence, for example in the case of a nucleic acid molecule, isolated may mean that it is free of 5' and 3' regulatory sequences. According to the present invention, for use in altering the expression of EPF in a cell of a plant, appropriate polynucleotide sequences may be integrated into an expression cassette, or construct (e.g. an expression vector) comprising one or more regulatory sequences to modulate the expression of the native EPF genes in a recipient plant. Preferably, the one or more regulatory sequences are designed to be operably linked to the polynucleotide sequences, in order to direct expression in a manner according to the present invention.

Expression Vectors and Regulatory Elements

The polynucleotides as described herein, and regulatory sequences are preferably provided as part of an expression cassette (e.g. an expression vector) for expression of the polynucleotide in a cell or tissue of interest of a monocot plant. Suitable expression vectors will vary according to the recipient plant chosen and suitably may incorporate regulatory elements which allow expression in the plant or plant cell of interest. Suitable expression cassettes for use in the present invention may be constructed by standard techniques known in the art, to comprise 5' and 3' regulatory sequences. Such regulatory sequences may be capable of influencing transcription or translation of a gene or gene product, for example in terms of initiation, accuracy, rate, stability, downstream processing and mobility. Examples of regulatory sequences include promoters, 5' and 3' UTR's, enhancers (e.g. VP16 transactivation domain), transcription factor or protein binding sequences, start sites and termination sequences, ribosome binding sites, recombination sites, polyadenylation sequences, sense or antisense sequences. They may be DNA, RNA or protein. The regulatory sequences may be operably linked to the sequences of interest. The regulatory sequences may be plant-, bacteria-, fungi- or virus-derived, and preferably may be derived from the same species of plant as the plant being modulated. Such elements may be included in the expression construct to obtain the optimal expression and function of EPF in the plant or plant material or, depending on the desired application, to obtain optimal reduction in, or elimination of expression of EPF in the plant or plant material. In addition, polynucleotides encoding, for example, selectable markers and reporter genes may be included. The expression cassette preferably also contains one or more restriction sites, to enable insertion of the nucleotide sequence and/or a regulatory sequence into the plant genome, at pre-selected loci. Also provided on the expression cassette may be transcription and translation initiation regions, to enable expression of the incoming genes, transcription and translational termination regions, and regulatory sequences. These sequences may be native to the plant being transformed, or may be heterologous. The expression cassettes may be a bi- or multi-functional expression cassette which functions in multiple hosts. Furthermore, as the application requires, the expression vector may further comprise additional elements which influence expression of the protein of interest in the host plant. Such regulatory sequences and elements can permit a skilled person to select in a predetermined manner a desired expression pattern in a host plant of interest depending on the application concerned. Suitable expression vectors may comprise additional sequences encoding selectable markers which allow for the selection of said vector in a plant cell and/or under particular conditions. Suitable expression vectors may also comprise additional sequences which enable visualisation or quantification of the expressed protein (e.g. 3' GFP or Luciferase fusion tags) in the plant cell of interest. Furthermore, the expression vector comprising the heterologous polynucleotide sequence may optionally comprise polynucleotide sequences coding for one or more transit peptides, capable of to localising the expressed protein to a particular cellular compartment in the recipient plant cell. Advantageously, such suitable transit peptides may cause the protein to localize to, for example, the cell wall, nucleus or chloroplasts. Preferably, expression vector will be the pBRACT214 gateway vector. More preferably, the expression vector will comprise EPF genomic (SEQ ID NO: 14) or cDNA (SEQ ID NO: 11) polynucleotide sequence(s) and one or more regulatory sequences (e.g. the maize ubiquitin promoter).

A regulatory sequence is a nucleotide sequence which is capable of influencing transcription or translation of a gene or gene product, for example in terms of initiation, accuracy, rate, stability, downstream processing and mobility. Examples of regulatory sequences include promoters, 5' and 3' UTR's, enhancers, transcription factor or protein binding sequences, start sites and termination sequences, ribosome binding sites, recombination sites, polyadenylation sequences, sense or antisense sequences. They may be DNA, RNA or protein. The regulatory sequences may be plant-, bacteria-, fungal- or virus derived, and preferably may be derived from the same species of plant as the plant being modulated to achieve optimal function of the sequences of interest in the recipient plant background and to reduce unwanted effects.

Typically, the one or more promoters controlling the expression of polynucleotides encoding EPF or sequences capable of hybridizing thereto, are optionally tissue or organ specific, such that expression of EPF or sequences capable of hybridizing thereto, can be directed to a particular organ or tissue, such as leaf tissue, preferably the epidermis. These promoters may be constitutive, whereby they direct expression under most environmental conditions or developmental stages, developmental stage specific, tissue-specific or inducible. Preferably, the promoter is tissue-specific, initiating transcription in the leaf tissue only. More preferably the promoter is inducible, to direct expression in response to environmental, chemical or developmental cues, such as temperature, light, chemicals, drought, heat stress, and other stimuli. It may be desirable for example to differentially control the number or density of stomata in different locations in the plant. For example it may be desired to transform the recipient plant with multiple copies of EPF, controlled by different regulatory elements, in order to differentially control the density of stomata in different tissues. It is also envisaged that EPF may be up-regulated in one part of the plant, e.g. in the leaves, but down-regulated elsewhere, e.g. in the anthers, or such that the stomatal density of the plant, or a particular tissue, changes at different developmental stages of growth. Clearly, a mixture of the approaches described herein may appropriately be used to achieve this.

It will be understood that a range of promoter sequences could in principle be used to drive the expression of the polynucleotide sequences disclosed herein, depending on the desired pattern of transcript accumulation. Commonly, strong promoters capable of producing a high-level of mRNA transcript of the gene of interest in the host plant will be used. In particular, those capable of driving high-levels of mRNA transcript of the gene of interest in the specific tissue of interest, will be selected for use in accordance with the present invention. Suitable promoter sequences may include but are not limited to those of the T-DNA of *A. tumefaciens*, including mannopine synthase, nopaline synthase, and octopine synthase; alcohol dehydrogenase promoter from *Zea mays*; light inducible promoters such as ribulose-biphosphate-carboxylase small subunit gene from various species and the major chlorophyll a/b binding protein gene promoter; histone promoters, actin promoters; *Zea mays* ubiquitin 1 promoter; 35S and 19S promoters of cauliflower mosaic virus; developmentally regulated promoters such as the waxy, zein, or bronze promoters from *Zea mays*; as well as synthetic or other natural promoters including those promoters exhibiting organ-specific expression or expression at specific plant development stages, such as the alpha-tubulin promoter. Preferred promoters for driving polynucleotide expression in recipient plants will include those which generate constitutive expression, for example the maize ubiquitin promoter. Alternative preferred promoters for driving expression of polynucleotides of the invention in recipient plants include those that generate stable expression in the leaf epidermal cells of the recipient plant. Preferred epidermis-specific promoters include *ARABIDOPSIS THALIANA* MERISTEM L1 (ATML1) and PROTODERMAL FACTOR2 (PDF2), the sequences of which are known in the art (San-Bento et al., Plant Journal 2014 77: 46-58). In a preferred embodiment, the ubiquitin promoter may be used to drive accumulation of EPF or sequences hybridizable thereto. It will also be appreciated that constitutive expression may not always be desired. For instance, particular applications may require subtle changes in stomatal density and therefore it may be desirable to match the strength of any promoter and/or regulatory sequences used to drive polynucleotide expression (e.g. polynucleotides encoding EPF) to the desired level of expression or activity in the host plant. Suitable promoters may be plant-, bacteria-, fungal- or virus derived or from any other suitable organism providing that they produce the desired expression pattern in the recipient plant. Suitable promoters need not be monocot derived, and could in principle be derived from another plant species such as, *Arabidopsis*. Preferably, however, promoter sequences may be derived from the same species of plant as the plant being modulated. Preferably, the promoters will be derived from Maize, Barley or Wheat.

An expression cassette comprising the heterologous nucleic acid may also comprise sequences coding for a transit peptide, to drive the protein coded by the heterologous gene into a desired part of the cell, for example the cell wall, nucleus or chloroplasts. Such transit peptides are well known to those of ordinary skill in the art, and may include single transit peptides, as well as multiple transit peptides obtained by the combination of sequences coding for at least two transit peptides (e.g. optimized transit peptide or chloroplast transit peptide), comprising in the direction of transcription a first DNA sequence encoding a first chloroplast transit peptide, a second DNA sequence encoding an N-terminal domain of a mature protein naturally driven into the chloroplasts, and a third DNA sequence encoding a second chloroplast transit peptide.

The invention also provides a composition comprising an expression vector as defined herein. Accordingly, such a composition may comprise an expression vector comprising a nucleotide sequence of any of SEQ ID NOs: 10 to 16 or variants thereof as defined herein.

In accordance with methods of the invention, in use, the vectors or compositions disclosed herein are usually applied directly onto the surface of the plant or crop. Typically, this may be achieved by direct application to the plant or crop, for example by rub-inoculation or by spraying the vector or composition directly onto the plant material, for example onto leaves, stems or roots of the plant during vegetative phase although other equally feasible methods of application will be known in the art. It is envisaged that the compounds disclosed herein may also be applied indirectly to the medium (e.g. soil or water) in which the plants or crop are grown.

Transformation of plants in accordance with the methods of the invention may involve a single application of the vector or composition either to the plant or to the growth medium. However, it will be understood that treatment may alternatively involve multiple applications of the same vector or composition or indeed combinations of the vectors or compositions disclosed herein. Where multiple (i.e. two or more) different vectors or compositions are applied to the same plant, these may be applied simultaneously, separately (in any order) or sequentially.

The vectors or compositions disclosed herein are typically provided to the plant or crop in the form of an aqueous solution. However, the vectors or compositions disclosed herein may also be provided to the plant or crop in solid form such as a powder, dust or in granular form and combinations thereof.

The invention provides the use of a composition comprising any of the vectors disclosed herein (and combinations thereof), either in expressing high-levels of EPF protein in a monocot plant to reduce stomatal density of the recipient plant compared to controls or alternatively in reducing the expression, level or activity of EPF in a monocot plant to increase stomatal density of the recipient plant compared to controls. Accordingly, the vectors or compositions disclosed herein are preferably to be applied to the plant or growth medium as an aqueous solution.

For convenience, vectors or compositions disclosed herein may be combined with other active ingredients used for the treatment of plants, for example they may be incorporated into other agrochemical products such as fertilisers, herbicides, anti-bacterial or anti-fungal agents and/or pesticides.

Determining EPF Expression

In various applications of the invention, it may be desirable to determine the expression levels of the EPF protein in recipient plants, plant parts, plant tissues or plant cells. Expression levels may be determined by various techniques which are routinely used in the art. In preferred embodiments of the present invention the expression levels of the protein in host organisms of interest may be determined. In some instances, it may be possible to directly determine functional expression, e.g. as with GFP or by enzymatic action of the protein of interest (POI) to generate a detectable optical signal. However, in some instances it may be chosen to determine physical expression, e.g. by antibody probing, and rely on separate test to verify that physical expression is accompanied by the required function.

In preferred embodiments of the invention, EPF expression will be detectable by a high-throughput screening method, for example, relying on detection of an optical signal. For this purpose, it may be necessary for the protein of interest (POI) to incorporate a tag, or be labelled with a removable tag, which permits detection of expression. Such a tag may be, for example, a fluorescence reporter molecule translationally-fused to the POI, e.g. Green Fluorescent Protein (GFP), Yellow Fluorescent Protein (YFP), Red Fluorescent Protein (RFP), Cyan Fluorescent Protein (CFP) or mCherry. Such a tag may provide a suitable marker for visualisation of functional EPF expression since its expression can be simply and directly assayed by fluorescence measurement in host organisms of interest. It may be an enzyme which can be used to generate an optical signal. Tags used for detection of expression may also be antigen peptide tags. Any tag employed for detection of expression may be cleavable from the POI. Other kinds of label may be used to mark the nucleic acid including organic dye molecules, radiolabels and spin labels which may be small molecules.

Plants and Plant Material

In all aspects of the invention, plant or plant material may be selected from any of whole plants, plant parts, plant tissues or plant cells. In accordance with the present invention, plants, plant material, or plant parts may refer to leaves, stems, leaf sheaths, roots, seed, grain, embryo, pollen, ovules, flowers, siliques, pods, ears, cobs, husks, stalks, fruits, root tips, anthers, pericarp, glumes, peduncles, silk, tissue or cells.

Modified plants of the invention, methods of generating them and polynucleotides or polypeptides employed in those methods may usually be directed at generating plants with either reductions in or increases in stomatal density in leaves compared with controls depending on the desired application, by varying the expression of EPF in leaves, or in all cells in the plant. However, the downstream effects of changes in stomatal density, namely improved WUE, drought tolerance and pathogen resistance will normally be derived in many parts of the plant, even if a change in EPF expression is only achieved in the leaves. Leaves may also not form part of the material of interest for harvesting purposes.

Host Plants (Improved WUE and/or Drought Tolerance)

In accordance with aspects of the present invention which relate to improved WUE, drought tolerance; plants, plant material or plant parts may be of any monocot species.

It will be appreciated that the methods, polynucleotides, polypeptides and expression vectors of the present invention are of broad utility and as such will find application in many monocot host (or recipient) plants. In particular, appropriate plants for use in accordance with the present invention may include monocot grasses, crops, vegetables and ornamentals. Of particular interest, plants suitable for modification with polypeptides and/or polynucleotides disclosed herein in accordance with the present invention are those which produce a high yield of grain for food, feedstock or biomass for fuel or paper production. Examples of suitable plant types include, but are not limited to, fast growing monocot crops, for example Wheat, Soybean, Rice, Maize, Sorghum, Millet, Barley, Rye, Oat, Sugar Cane and Sugar Beet. Preferably, the plant is a cereal crop selected from the genera *Triticum, Aegilops, Panicum, Setaria, Zea, Oryza, Hordeum, Sorghum, Avena, Saccharum* or *Secale*. In particular, the plant may be a *Hordeum* sp. plant or a *Zea* sp. plant. Where the plant is a *Hordeum* sp. plant, preferably the plant is a *Hordeum vulgare* plant. Where the plant is a *Zea* sp. plant, preferably the plant is a *Zea mays* plant.

Other appropriate plants may include those plants which have a high water demand and/or are used for biofuel or cellulose production, for example energy grasses. Preferred perennial grasses for use in the invention include Switchgrass (*Panicum virgatum*), Prairie Cordgrass (*Spartina* sp.), Reed Canary Grass (*Phalaris arundinacea*), Purple False Brome (*Brachypodium distachyon*), Sudan Grass (*Sorghum×drummondii*) and Elephant Grass (*Miscanthus* sp.).

Commonly, an appropriate plant for use in accordance with the invention is used typically as a crop, whether for food, energy or other purposes. In preferred aspects of the invention said plant may be selected from: Barley (*Hordeum vulgare*), Wheat (*Triticum aestivum, Triticum durum*), Maize (*Zea mays*), Canola (*Brassica napus, Brassica rapa* sp.), Rice (*Oryza sativa*), Sugar Beet (*Beta vulgaris*), Oat (*Avena sativa*), Rye (*Secale cerale*), Sorghum (*Sorghum* bicolor, *Sorghum vulgare*), Soybean (*Glycine max*), Millet (for example Pearl Millet (*Pennisetum glaucum*), Foxtail Millet (*Setaria viridis*), Finger Millet (*Eleusine coracana*), Proso Millet (*Panicum miliaceum*)), *Miscanthus* sp. (e.g. *Miscanthus×giganteus, Miscanthus sinensis* and *Miscanthus sacchariflorus*), Tausch's Goatgrass (*Aegilops tauschii*), *Pennisetum* sp., banana (*Musa* spp.), Ginger (*Zingiber* sp.), Orchids (Orchidaceae), Onions, Garlic, Tulips (*Tulipa* sp.), Lilies, Daffodils (*Narcissus*), Irises, or Amaryllis.

Usefully, the plant may be a plant of the genus *Hordeum* L., *Triticum* L., *Oryza* L., or *Zea* L. or the plant material is derived from a plant of the genus *Hordeum* L., *Triticum* L., *Oryza* L., or *Zea* L. The plant may be a *Hordeum vulgare* L. plant or the plant material may be derived from a *Hordeum vulgare* L. plant. Similarly, the plant may be a *Triticum*

*aestivum* L. plant or the plant material may be derived from a *Triticum aestivum* L. plant. Equally, the plant may be an *Oryza sativa* L. plant or the plant material may be derived from an *Oryza sativa* L. plant. Alternatively, the plant may be a *Zea mays* L. plant or the plant material may be derived from a *Zea mays* L. plant.

Host Plants (Improved Resistance to Infection by Microbial Pathogens)

In accordance with aspects of the present invention which relate to improved resistance to infection by microbial pathogens; plants, plant material or plant parts may be of any plant species, which may be monocots or dicots. In contrast to other aspects of the invention disclosed herein, which are restricted in their application to monocot plants, aspects of the invention which relate to methods of modifying a plant or plant material to impart at least partial resistance to, or improve resistance to infection by a microbial pathogen, wherein the method comprises increasing the expression and/or level and/or activity of EPF polypeptide in cells of the plant or plant material compared to cells of an equivalent control plant or plant material; are applicable to both monocot and dicot plants. Although in preferred aspects, the plant is still a monocot plant, and preferably the plant is of, or the plant material is derived from a plant selected from the genera *Hordeum* L., *Triticum* L., *Oryza* L., or *Zea* L., increases in the expression level and/or activity of EPF improve resistance to microbial pathogens in both monocot (e.g. *Oryza*) and dicot (e.g. *Arabidopsis*) host backgrounds compared to an equivalent unmodified or untransformed control plant or plant material. Therefore, methods of improving resistance to pathogen infection disclosed herein are applicable to any plant species, which may be used as a host system for mis-expression or over-expression of EPF. Accordingly, in addition to the monocot host species disclosed herein, suitable host plants may include, but are not limited to; for example, tobacco (*Nicotiana tabacum*), potato (*Solanum tuberosum*), tomato (*Solanum lycopersicum*) or *Arabidopsis*. Typically, the plant may be a *Hordeum vulgare* L. plant or the plant material may be derived from a *Hordeum vulgare* L. plant. Similarly, the plant may be a *Triticum aestivum* L. plant or the plant material may be derived from a *Triticum aestivum* L. plant. Equally, the plant may be an *Oryza sativa* L. plant or the plant material may be derived from an *Oryza sativa* L. plant. Alternatively, the plant may be a *Zea mays* L. plant or the plant material may be derived from a *Zea mays* L. plant. The plant may be an *Arabidopsis thaliana* L. plant or the plant material may be derived from an *Arabidopsis thaliana* L. plant.

Stomatal Density

Stomatal densities of modified, transgenic or transformed plants produced in accordance with the invention will usually be assessed by assaying number of stomata per unit area in tissues of resultant plants, preferably leaves. In particular, the epidermis of leaves may be assessed. This may be done using techniques which are well known in the art, that include, for example, producing an epidermal impression by coating a leaf surface, for example the abaxial leaf surface with e.g. nail varnish, peeling off the dried layer of nail varnish, mounting in water on a slide and examining the impression under a microscope. Stomatal number per unit leaf area may then be calculated. Typically, the first leaves of seedling host plants may be compared with control plants (transformed with an empty-vector). Stomatal index (SI) may also be calculated, wherein the stomatal index is stomatal density expressed as a percentage of all cells on the epidermis.

Such stomatal densities and/or indices of modified or transformed plants may appropriately be compared to those of genetically equivalent, but unmodified or untransformed control plants. Modifications (i.e. increases or reductions) in leaf stomatal density or stomatal index may suitably be assessed on a single leaf basis or across multiple leaves.

Plants, plant material or plant parts with "altered stomatal density", or "modified stomatal density" may refer to plants having alterations in the location of stomates, increases or reductions in the number of stomata per unit area (Stomatal Density or SD) and/or per epidermal cell number (Stomatal Index or SI) relative to unmodified or untransformed plants, plant material or plant parts. In preferred embodiments, the number of stomata per unit leaf area in a modified plant, plant part or plant material is increased relative to that of an equivalent, control plant. More preferably, where the goal is increased stomatal number, the stomatal index, that is the density of stomata per epidermal cell number in a modified plant, plant part or plant material is increased relative to that of an equivalent, control plant. Alternatively, the density of stomata, that is the number of stomata per unit leaf area in a modified plant, plant part or plant material may be reduced relative to that of an equivalent, control plant. The stomatal index of a modified or transformed plant may be reduced compared to that of an equivalent, control plant. Additionally, stomata may also be ectopically located relative to that of an equivalent, control plant.

In embodiments of the invention where the stomatal density is reduced relative to controls, the stomatal density of modified plants may optionally be 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% of control values.

In embodiments of the invention where the stomatal density is increased relative to controls, the stomatal density of modified plants may optionally be 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, optionally in the range 150% to 199%, 200% to 249%, 250%, to 299%, 300% to 349%, 350% to 399%, 400% to 449%, 450% to 499%, 500% to 599%, 600% to 699%, 700% to 799%, 800% to 899% or 900% to 1000% of control values.

The methods, polypeptides, polynucleotides and expression vectors disclosed herein may usefully be deployed to vary the levels of stomatal density in a recipient host plant such that it may be tuned to the required environmental or biotic conditions. The level of stomatal density may conveniently be controlled by varying the strength of expression of the polypeptide or polynucleotide. In the case of EPF, this will be an inverse relationship with stomatal density. Such variation in EPF levels may be achieved by techniques which are well known in the art and may include but are not limited to selecting a promoter to drive appropriate levels of transcript accumulation, using activator sequences or enhancer elements operably linked to the polynucleotide encoding EPF or by increasing the stability of the transcript or protein.

The methods, polypeptides, polynucleotides and expression vectors disclosed in accordance with the present invention find general utility in generating monocot plants with modifications in stomatal density. Depending on the desired application, modified stomatal density may mean increased stomatal density relative to unmodified control plants, or alternatively it may mean reduced stomatal density relative to unmodified control plants. It will also be appreciated that the discovery of a master switch governing the control of stomatal development which is capable of operation in monocots allows the generation of monocot plants in which stomatal density may be varied temporally, developmentally or in response to chemical or environmental cues.

Isolated Polynucleotides

The invention also provides an isolated polynucleotide comprising a polynucleotide sequence of;

SEQ ID NO: 9; or a sequence of at least 67%; preferably at least 90%; more preferably at least 95%; even more preferably at least 98% identity thereto; or SEQ ID NO: 10; or a sequence of at least 67%; preferably at least 90%; more preferably at least 95%; even more preferably at least 98% identity thereto; or SEQ ID NO: 11; or a sequence of at least 59%; preferably at least 90%; more preferably at least 95%; even more preferably at least 98% identity thereto; or SEQ ID NO: 13; or a sequence of at least 66%; preferably at least 90%; more preferably at least 95%; even more preferably at least 98% identity thereto; or SEQ ID NO: 14; or a sequence of at least 58%; preferably at least 90%; more preferably at least 95%; even more preferably at least 98% identity thereto.

Expression Cassettes/Vectors

Any of the polynucleotides disclosed herein may be conveniently provided integrated in an expression vector, in order that they may rapidly be used in the transformation of host plant material. Accordingly, the invention provides an expression vector comprising a polynucleotide sequence of any of SEQ ID NO: 9, SEQ ID NO: 10, SEQ ID NO: 11, SEQ ID NO: 13, SEQ ID NO: 14, SEQ ID NO: 15, or SEQ ID NO: 16 or a variant sequence thereof as defined herein by percentage sequence identity.

Such an expression vector may be any vector which is capable of driving expression of the polynucleotide contained therein in a tissue of interest in a monocot plant, at a developmental stage of interest or in response to an environmental or chemical cue. As such appropriate vectors may contain any appropriate genetic architecture suitable for enabling high-level expression of the polynucleotides contained therein in the recipient plant or plant material, compared to the native level of EPF expression in an unmodified plant, including, for example, promoters, enhancers, 5' and/or 3' control regions.

The present invention provides an expression vector, wherein the vector comprises a polynucleotide sequence of SEQ ID NO: 10 to 16, and any percentage variant thereof as herein defined by percentage sequence identity.

The present invention provides an expression vector comprising a polynucleotide capable of hybridizing to a polynucleotide comprising SEQ ID NO: 14 or SEQ ID NO: 9 under stringent conditions.

Expression vectors disclosed herein may suitably be provided as a component of a kit of parts, together with instructions for use.

Vector Delivery

The vectors can be delivered in several different ways into the recipient plant, such as for example, Wheat, Barley or Rice.

Optionally, the vectors may be delivered into the recipient plant by direct agro-inoculation of *Agrobacterium* cultures transformed with binary vectors. Alternatively, the vectors may be delivered into the recipient plant by rub inoculation of plant leaves with sap prepared from another agro-inoculated host. In a further alternative, the vectors may be delivered into the recipient plant by rub-inoculation of plant leaves with in vitro transcript. In another alternative, the vectors may be delivered into the recipient plant by bombardment of plant leaves with gold particles coated with the plasm ids.

Transformation of the plants with expression vectors disclosed herein, in accordance with the methods of the invention may involve a single application of the vector to the plant. However, it will be understood that treatment may alternatively involve multiple applications of the same vector or composition or indeed combinations of the expression vectors disclosed herein. Where multiple (i.e. two or more) different vectors are applied to the same plant, these may be applied simultaneously, separately (in any order) or sequentially. The vectors may be delivered into the recipient plant by any combination of the above methods.

Methods for Identifying Plants with Improved WUE, Drought Resistance and/or Improved Pathogen Resistance In certain circumstances it may be desirable to test plant material, for example seed, to determine if it has polynucleotide sequences, which on expression confer the plant or plant material with either increased or decreased expression of EPF. Accordingly, the present invention provides a method for identifying whether a plant has resistance to infection by a microbial pathogen comprising detecting in a sample of the plant the level of expression of:

a. a polynucleotide of any of SEQ ID NO: 10 to 16, and any percentage variant thereof as defined herein by percentage sequence identity; or b. a polypeptide of any of SEQ ID NO: 1 to 8, and any percentage variant thereof as defined herein by percentage sequence identity;

and comparing the level of expression to that of a control plant; wherein an increase in expression relative to that of the control plant is indicative of resistance to infection by a microbial pathogen.

Polynucleotides or polypeptides encoding EPF in the sample(s) from the plant being tested for resistance are said to be differentially expressed and indicative of resistance to infection by a microbial pathogen, and/or of improved WUE and/or of improved drought tolerance, where they are significantly up-regulated in comparison to those of a control plant. Depending on the individual marker, resistance to infection by a microbial pathogen may be detected in a plant sample by an increase in EPF expression level, scaled in relation to sample mean and sample variance, relative to those of control plants or one or more reference values. Variation in the plants, the regulatory architecture used to drive expression of the polynucleotides encoding EPF, material therefrom and samples mean that different levels of confidence are attached to each marker. EPF expression levels are said to be highly significantly up-regulated when after scaling of biomarker expression levels in relation to sample mean and sample variance, they exhibit a 2-fold change compared with controls or one or more reference values. Preferably, samples of plants with resistance to infection by a microbial pathogen will exhibit a 3-fold change or more compared with the reference value. More preferably plants with resistance to infection by a microbial pathogen will exhibit a 4-fold change or more compared with the reference value. That is to say, in the case of increased expression level (up-regulation relative to reference values), the expression level will be more than double that of the reference value. Preferably the expression level of a resistant plant will be more than 3 times the level of the reference value. More preferably, the expression level of a resistant plant will be more than 4 times the level of the reference value.

The expression level of EPF in resistant plants or plant material may optionally be 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, optionally in the range 150% to 199%, 200% to 249%, 250%, to 299%, 300% to 349%, 350% to 399%, 400% to 449%, 450% to 499%, 500% to 599%, 600% to 699%, 700% to 799%, 800% to 899% or 900% to 1000% relative to that of one or more control values. Ordinarily, a control value will be that of a genetically equivalent, but unmodified control plant or equivalent material thereof. Such a control value may appropriately be calculated as a mean value of several control plants.

The pathogen may be a fungal or bacterial pathogen. The pathogen may be of the genus *Puccinia, Pseudomonas, Septoria* or *Xanthomonas*. The pathogen may be *Pseudomonas syringae*. The pathogen may be *Puccinia hordei*. The pathogen may be *Zymoseptoria tritici*. The pathogen may be *Xanthomonas oyzae*. In this aspect of the invention, the plant may be a monocotyledonous plant (e.g. *Oryza*) or alternatively may be a dicotyledonous plant (e.g. *Arabidopsis*). Preferably, the plant is a plant of the genus *Hordeum* L., *Triticum* L., *Oryza* L. or *Zea* L, for example selected from *Hordeum vulgare* L., *Triticum aestivum* L., *Oryza sativa* L. and *Zea mays* L.

Diagnostic Devices

In a further aspect, the present invention provides a diagnostic device for use in the detection of a plant having at least partial microbial resistance, the device comprising: a loading area for receiving a biological sample; a substrate comprising at least one binding partner specific for a target molecule indicative of the expression of a polynucleotide of SEQ ID NO: 11 or SEQ ID NO: 14; and any percentage variant thereof as herein defined by percentage sequence identity; or a polypeptide of SEQ ID NO: 8 and any percentage variant thereof as herein defined by percentage sequence identity; and detection means to detect the levels of said polynucleotide or polypeptide present in the sample. Preferably the at least one binding partner comprises nucleic acid primers adapted to hybridize specifically to a polynucleotide of SEQ ID NO: 11 or SEQ ID NO: 14, or a fragment thereof under stringent conditions. Preferably the at least one binding partner further comprises a fluorescent moiety, for example a molecular beacon.

Such a device may suitably be a microarray or DNA chip or a flow and capture device. Suitably the device comprises specific binding partners which selectively bind to a target molecule indicative of the presence or expression of a polynucleotide as hereinbefore defined. Target molecules may suitably be RNA molecules, DNA molecules, cDNA molecules or alternatively proteins or polypeptides encoded by a polynucleotide as hereinbefore defined. A variety of suitable array or chip-based or liquid-based capture technologies are well known in the art and suitable for the purpose.

Suitably the at least one binding partner are selected from the group consisting of: complementary nucleic acids; aptamers; antibodies or antibody fragments. Suitable classes of binding partners for any given polynucleotide or protein will be apparent to the skilled person.

Preferably, the at least one binding partner comprises nucleic acid primers adapted to hybridize specifically to a polynucleotide of SEQ ID NO: 10 or SEQ ID NO: 11 or a fragment thereof under stringent conditions.

More preferably, the at least one binding partner preferably comprises nucleic acid primers adapted to hybridize specifically to a polynucleotide of SEQ ID NO: 11 or a fragment thereof under stringent conditions.

The device is preferably adapted to detect and quantify the levels of said polynucleotides or proteins present in the biological sample. This may be with reference to a positive control or alternatively with reference to an internal standard.

Preferably, the biological sample is an extract or lysate from a plant, plant cell, plant tissue or plant part, for example homogenized leaf tissue. The biological sample may suitably be homogenized, processed, buffered and/or purified prior to loading on the device.

Suitably the levels of the target molecules in the biological sample are detected by direct assessment of binding between the target molecules and binding partners.

Usually, the levels of the target molecules in the biological sample are detected using a reporter moiety attached to a binding partner.

Preferably the reporter moiety is selected from the group consisting of: fluorophores; chromogenic substrates; and chromogenic enzymes.

More preferably, the at least one binding partner further comprises a fluorescent moiety, for example a molecular beacon.

One particularly useful application of the present invention is the ability to easily identify plants which are resistant to a bacterial infection, in particular those resistant to infection by *Pseudomonas*, preferably *Pseudomonas syringae*.

One particularly useful application of the present invention is the ability to easily identify plants which are resistant to a fungal infection, in particular those resistant to infection by *Puccinia*, preferably *Puccinia hordei*.

Kits for Determining Expression Levels of EPF

The present invention also provides a kit of parts for selectively determining, in a sample, the expression levels of one or more of the polynucleotides of SEQ ID NO: 9, SEQ ID NO: 10, SEQ ID NO: 11, SEQ ID NO: 13, and/or SEQ ID NO: 14, and any percentage variant thereof as herein defined by percentage sequence identity; or a polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, and/or SEQ ID NO: 8; wherein the kit comprises: at least one binding partner that selectively binds to a polynucleotide or polypeptide as hereinbefore defined, or a fragment thereof; a positive control for the detection of said polynucleotide or polypeptide; at least one binding partner that selectively binds to a nucleic acid or polypeptide which operates as an internal control; and optionally an internal standard.

Binding PARTNERS

In certain embodiments of the invention, the existence of at least partial bacterial or fungal resistance in a plant may be investigated by determining the presence or expression of one or more of the polynucleotides of SEQ ID NO:9; SEQ ID NO: 10, SEQ ID NO: 11, SEQ ID NO: 13 and/or SEQ ID NO: 14, and any percentage variant thereof as herein defined by percentage sequence identity; or a polypeptide of SEQ ID NO: 1, SEQ ID NO: 2, SEQ ID NO: 3, SEQ ID NO: 4, SEQ ID NO: 5, SEQ ID NO: 6, SEQ ID NO: 7 and/or SEQ ID NO: 8; and any percentage variant thereof as herein defined by percentage sequence identity. Preferably, the existence of at least partial bacterial and/or fungal resistance in a plant may be investigated by quantifying the expression levels in a biological sample of any of the target molecules indicative of the expression of a polynucleotide of SEQ ID NOs: 9, 10, 11, 13 or 14 or a polypeptide of any of SEQ ID NOs: 1 to 8, using binding partners which bind or hybridize specifically to the target molecules or a fragment thereof under stringent conditions. In relation to the present invention the term 'binding partners' may include any ligands, which are capable of binding specifically to the relevant target molecule and/or nucleotide or peptide variants thereof with high affinity. Said ligands include, but are not limited to nucleic acids (DNA or RNA), proteins, peptides, antibodies, synthetic affinity probes, carbohydrates, lipids, artificial molecules or small organic molecules such as drugs. In certain embodiments the at least one binding partner may be selected from a complementary nucleic acid; aptamer; antibody or antibody fragment. In the case of detecting mRNAs, nucleic acids represent particularly suitable binding partners.

In the context of the present invention, a binding partner specific to a target molecule should be taken as requiring that the binding partner should be capable of binding to or hybridizing to at least one such target molecule in a manner that can be distinguished from non-specific binding to molecules that are not target molecules. A suitable distinction may, for example, be based on distinguishable differences in the magnitude or affinity of such binding.

In preferred embodiments of the methods or devices of the invention, the target molecule is a nucleic acid, preferably an mRNA molecule, and the at least one binding partner is a complementary nucleic acid or aptamer.

Suitably the binding partner is a nucleic acid molecule (typically DNA, but it can be RNA) having a sequence which is complementary to the sequence of the mRNA or cDNA against which it is targeted. Such a nucleic acid is often referred to as a 'probe' (or a reporter or an oligo) and the complementary sequence to which it binds is often referred to as the 'target'. Probe-target hybridization is usually detected and quantified by the detection of fluorophore-, silver-, or chemiluminescence-labelled targets to determine relative abundance of nucleic acid sequences in the sample.

Probes may be from 25 to 1000 nucleotides in length. However, lengths of 30 to 100 nucleotides are preferred, and probes of around 50 nucleotides in length are most commonly used with success in transcriptome and genome analyses.

While the determination of suitable probes can be difficult, e.g. in very complex arrays, there are many commercial sources of complete transcriptome arrays available, and it is routine to develop bespoke arrays to detect any given set of specific mRNAs or DNAs using publically available sequence information. Commercial sources of microarrays for transcriptome analysis include Illumina and Affymetrix and for exome capture analysis include NimbleGen and MYcroarray and for genome analysis include Affymetrix, low and high density arrays.

Where the target molecules to be detected are polynucleotides, for example polynucleotides of SEQ ID NO: 9, SEQ ID NO: 10, SEQ ID NO: 11, SEQ ID NO: 13 or SEQ ID NO: 14, and any percentage variant thereof as herein defined by percentage sequence identity; probe sequences may be designed to any sequence region of the cDNA transcript or a fragment or variant thereof. The person skilled in the art will appreciate that equally effective probes can be designed to a number of different regions of the transcript, and that the effectiveness of the particular probes chosen will vary, amongst other things, according to the platform used to measure transcript abundance and the hybridization conditions employed. It will therefore be understood that probes targeting different regions of the transcript may also be used in accordance with the present invention. Preferably, the target molecule to be detected is a polynucleotide of SEQ ID NO: 9, SEQ ID NO: 10, SEQ ID NO: 11 or SEQ ID NO: 14, or a fragment or variant thereof and probes which are capable of binding specifically to the polynucleotide under stringent conditions may be designed accordingly.

In other suitable embodiments of the invention, the target molecule may be a protein, and the at least one binding partner selected from an antibody, antibody fragment or an aptamer.

Where the target molecule is a polypeptide, antibodies may be designed to any sequence region of the SEQ ID NO: 8 amino acid sequence or a fragment or variant thereof.

Polynucleotides encoding any of the specific binding partners of target molecules of the invention recited above may be isolated and/or purified nucleic acid molecules and may be RNA or DNA molecules.

Commonly, polypeptide sequences and polynucleotides used as binding partners in the present invention may be isolated or purified. By "purified" is meant that they are substantially free from other cellular components or material, or culture medium. "Isolated" means that they may also be free of naturally occurring sequences which flank the native sequence, for example in the case of nucleic acid molecule, isolated may mean that it is free of 5' and 3' regulatory sequences.

Commonly, polypeptide sequences and polynucleotides may be used as binding partners within living tissues. These polypeptide sequences and polynucleotides may be expressed partners that are tagged with different fluorescent proteins, for example Cerulean protein and Venus protein. Tagged proteins are often used as a donor-acceptor pair by researchers in Förster Resonance Energy Transfer (FRET) based co-localization studies to monitor protein interactions.

In a preferred embodiment the nucleic acid is mRNA. There are numerous suitable techniques known in the art for the quantitative measurement of mRNA transcript levels in a given biological sample. These techniques include but are not limited to; "Northern" RNA blotting, Real Time Polymerase Chain Reaction (RTPCR), Quantitative Polymerase Chain Reaction (qPCR), digital PCR (dPCR), multiplex PCR, Reverse Transcription Quantitative Polymerase Chain Reaction (RT-qPCR), branched DNA signal amplification or by high-throughput analysis such as hybridization microarray, Next Generation Sequencing (NGS) or by direct mRNA quantification, for example by "Nanopore" sequencing. Alternatively, "tag based" technologies may be used, which include but are not limited to Serial Analysis of Gene Expression (SAGE). Commonly, the levels of target molecule mRNA transcript in a given biological sample may be determined by hybridization to specific complementary nucleotide probes on a hybridization microarray or "chip", by Bead Array Microarray technology or by RNA-Seq where sequence data is matched to a reference genome or reference sequences.

In a preferred embodiment, the present invention provides a method for identifying whether a plant has resistance to a bacterial or fungal infection comprising detecting in a sample of the plant the presence or expression level of a polynucleotide of SEQ ID NO: 9, SEQ ID NO: 10, SEQ ID NO: 11, or the expression level of a polynucleotide encoded by SEQ ID NO: 13 or SEQ ID NO: 14, and any percentage variant thereof as herein defined by percentage sequence identity; or a polypeptide of SEQ ID NO: 1, SEQ ID NO: 2, SEQ ID NO: 3, SEQ ID NO: 4, SEQ ID NO: 5, SEQ ID NO: 6, SEQ ID NO: 7 and/or SEQ ID NO: 8; and any percentage variant thereof as herein defined by percentage sequence identity.

Preferably, the method for identifying whether a plant has resistance to a bacterial infection comprises detecting in a sample of the plant the expression level of: a polynucleotide of SEQ ID NO: 9 or SEQ ID NO: 11. The expression level of a polynucleotide of any of SEQ ID NOs: 9, 10, 11, 13 or 14 may expeditiously be determined by PCR, for example by qPCR, dPCR, RTPCR or multiplex PCR. Preferably the abundance of mRNA transcript generated by SEQ ID NO: 14 or a fragment or variant thereof will be quantified (e.g. SEQ ID NO: 9).

The person skilled in the art will appreciate that effective nucleotide primers may be designed to any sequence region of a polynucleotide of SEQ ID NO: 14 or a fragment or variant thereof or a region of the transcript generated from expression of SEQ ID NO: 14, and that the effectiveness of the particular primers chosen will vary, amongst other things, according to the platform used to measure transcript abundance, the biological sample and the hybridization conditions employed. Although it will be appreciated that, in principle, primers targeting any region of the transcript may be used in accordance with the present invention, the person skilled in the art will recognise that in designing appropriate primer sequences to detect polynucleotide expression, it is required that the primer sequences be capable of binding selectively and specifically to the cDNA sequence of SEQ ID NO: 11 or a fragment or variant thereof (e.g. SEQ ID NO: 10).

In a further aspect, the present invention provides a kit of parts for selectively determining, in a sample, the expression levels of one or more of the polynucleotides of SEQ ID NOs: 9 to 16, wherein the kit comprises:
 a. at least one binding partner that selectively binds to a polynucleotide of any of SEQ ID NOs: 9 to 16, or a fragment thereof;
 b. a positive control for the detection of said polynucleotide;
 c. at least one binding partner that selectively binds to a nucleic acid which operates as an internal control; and
 d. optionally an internal standard.

Suitably the device comprises specific binding partners to the polynucleotide(s) being amplified. The binding partners are preferably nucleic acid primers adapted to bind or hybridize specifically to the polynucleotide of SEQ ID NOs: 9 to 16. Preferably primers will be provided that specifically target a polynucleotide of SEQ ID NO: 14 or a fragment thereof.

A variety of suitable PCR amplification-based technologies are well known in the art. PCR applications are routine in the art and the skilled person will be able to select appropriate polymerases, buffers, positive controls, internal standards, reporter moieties and reaction conditions as desired.

Detailed Description of the Invention

BRIEF DESCRIPTION OF THE FIGURES

The invention will now be described in detail with reference to examples and with reference to the accompanying drawings, in which:

FIG. 1a discloses SEQ ID NOS 8, 29, and 30, respectively, in order of appearance. (b) Overexpression of HvEPF1 under the control of the CaMV35S promoter in Arabidopsis leads to a significant decrease in stomatal density. (c) Epidermal tracings from Arabidopsis cotyledons overexpressing EPF1, EPF2, and HvEPF1 alongside the background control Col-0. Red dots mark location of stomata whilst green dots mark location of arrested meristemoids. N=5 plants, asterisks indicate $P<0.05$, (Dunnett's test after one-way ANOVA). Error bars represent SE.

FIG. 8 (Panel A) discloses SEQ ID NOS 31-45, 11, and 46, respectively, in order of appearance.

Panel B shows an alignment of deduced EPF1/2 like proteins from *Arabidopsis thaliana* (At), *Triticum aestivum* (Ta), *Oryza sativa* (Os), *Hordeum* vulgarum (Hv) and *Zea mays* (Zm). Cysteine residues unique to stomatal density altering EPFs are indicated with an asterisk. Conserved (active) region is indicated (shaded box). FIG. 8 (Panel A) discloses SEQ ID NOS 31-45, 11, and 46, respectively, in order of appearance.

FIG. 9-3 shows Phylogenetic tree of predicted *Arabidopsis* and barley epidermal patterning factor peptide sequences constructed using Multalin. Barley annotations taken from Ensembl Plants. HvEPF1 is highlighted in red.

FIG. 9-5 shows growth of barley plants is inhibited by the water-restricted conditions used in this study (25% soil water content) in comparison to growth in well-watered conditions (60% soil water). From left to right: Control plant well-watered, control water-restricted, HvEPF1OE-1 well watered, HvEPF1OE-1 water-restricted, HvEPF1OE-2 well-watered and HvEPF1OE-2 water-restricted.

FIG. 9-6 shows plant heights of controls and HvEPF1OE-3 or HvEPF1OE-4 were not significantly different within either well-watered or water-restricted conditions. Error bars represent SE.

FIG. 9-7 shows above ground biomass of control and HvEPF1OE-3 or HvEPF1OE-4 plant lines were not significantly different under either well-watered or water-restricted conditions. N=5 plants. Error bars represent SE.

FIG. 9-1 shows schematic of the gene expression construct inserted into the barley genome to overexpress the HvEPF1 gene.

FIG. 9-2 shows qPCR results the confirming significant overexpression of HvEPF1 the barley lines. N=5 plants, asterisk indicates significance to at least $P<0.05$ (Dunnett's tests after one-way ANOVA). Error bars represent SE.

FIG. 9-4 shows an alignment of HvEPF1 and HvEPF2 proteins with At1g34245, At1g71866, and At2g20875. FIG. 9-4 discloses SEQ ID NOS. 8, 29, 60-61, and 30, respectively, in order of appearance.

*Arabidopsis* plants with altered stomatal density do not have altered resistance to infection when syringe infiltrated to overcome any stomatal limitation.

Figure 11:
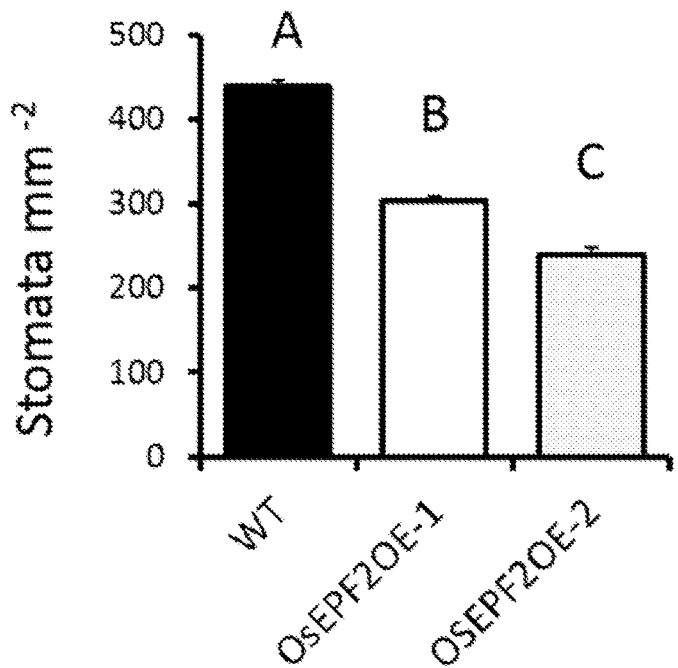
Figure 11:
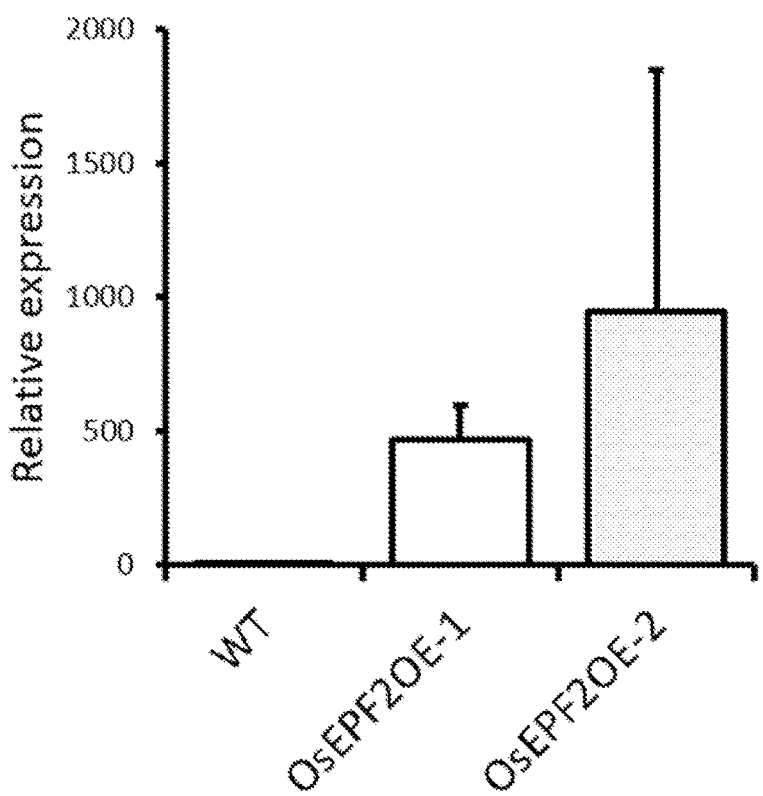

FIG. 11 shows reduced stomatal density and overexpression of EPF in Rice. Panel A shows stomatal density is reduced in rice transformed with OsEPF2 in the pSC310 vector. Letters indicate EPF2 overexpression lines are statistically significant from wild type in first leaf. Panel B shows qPCR expression showing over-expression of the OsEPF2 gene at 8 days old in two transgenic lines.

Figure 12:
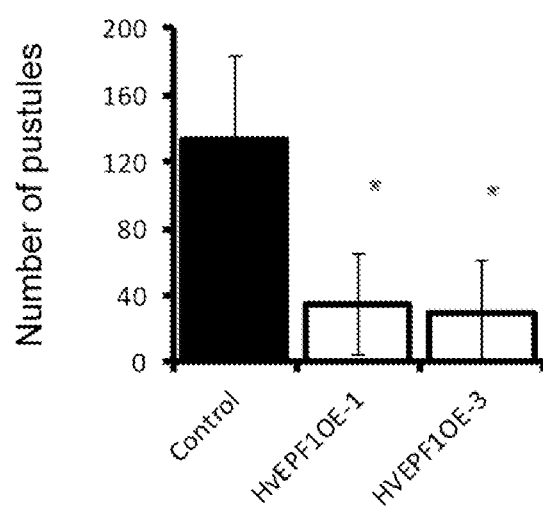

FIG. 12 shows reduced infection by brown rust in barley lines with reduced stomatal density. Lines HvEPF1OE1 and HvEOPF10E3 were infected with spores of *Puccinia hordei* and showed a significant ($p<0.01$ by t:test) reduction in infection as measured by pustule number. Significant differences indicated by *. n=6 plants.

Figure 13:
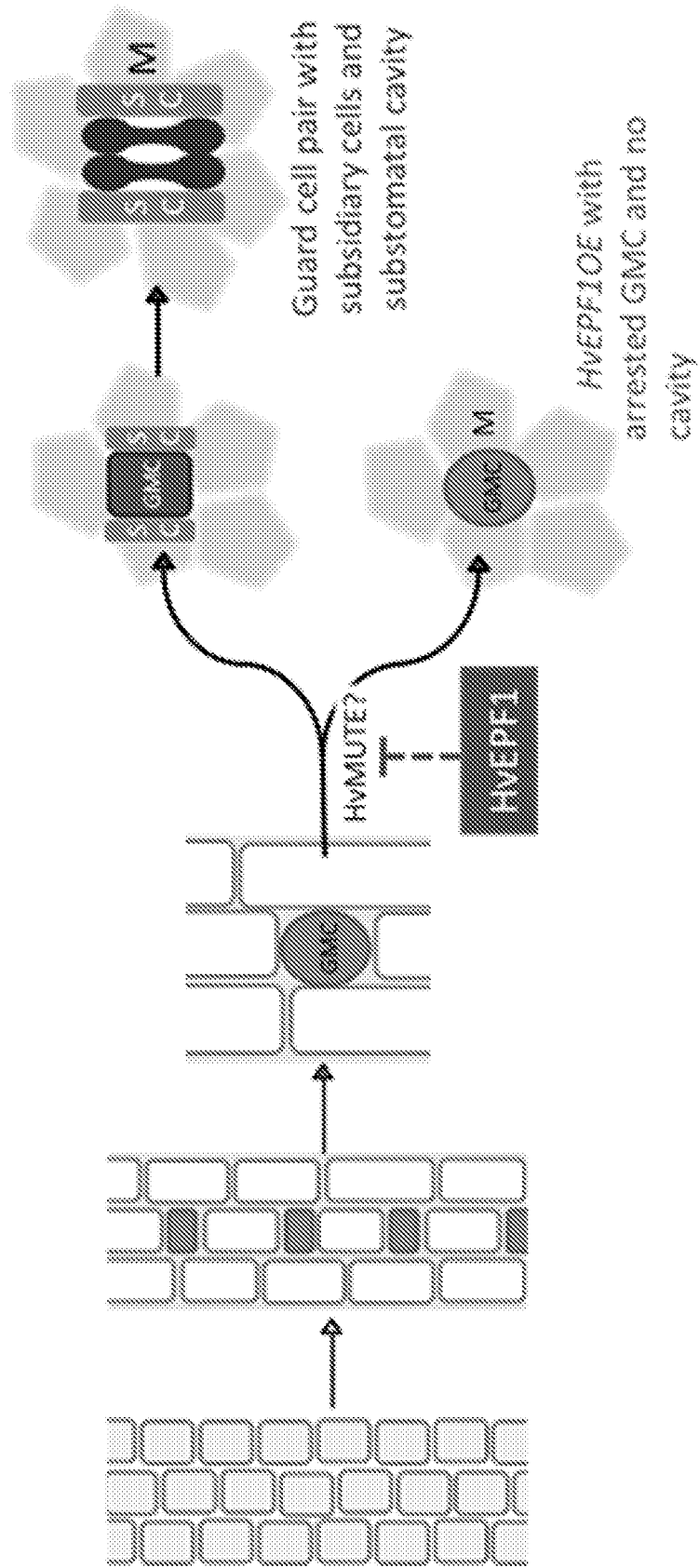

FIG. 13 shows HvEPF1 may act to prevent guard mother cell maturation and subsequent substomatal cavity and subsidiary cell formation. Schematic to illustrate the putative mode of action of HvEPF1 in barley stomatal development. Left to right: Undifferentiated epidermal cells at the base of leaves are formed in cellular files. Cells in some files gain the capacity to divide asymmetrically to create small stomatal precursor cells shown here as immature guard mother cells (GMC, green). A developmental step, potentially under the control of the transcription factor MUTE, stimulates guard mother cell maturation (dark green) and division of adjacent epidermal cells to form subsidiary cells (SC, orange). Mature GMCs then divide symmetrically to form pairs of dumbbell shaped guard cells (red). In the underlying mesophyll layer (M, green shaded regions) a substomatal cavity forms during either the mature GMC or guard cell stage, although the exact developmental staging of this is process is unknown. In the HvEPF1 overexpressing plants, HvEPF1 prevents GMC maturation perhaps through the suppression of MUTE activity, resulting in arrested GMCs which are unable to differentiate further or to form subsidiary cells, guard cells or substomatal cavities. Drawn with reference to *Brachypodium* development in Raissig et al. 2016.

EXAMPLES

Example 1: Identification of EPF1 Gene in Monocots

The inventors have been able to identify a putative EPF ortholog in the barley genome (HvEPF1, MLOC_67484). HvEPF1 is expressed at low levels during development of aerial tissues (IBSC 2012. International Barley Genome Sequencing Consortium: Nature Publishing Group. 711-716). The function of this ortholog in grasses, was unknown until now.

Example 2: Vector Construction

HvEPF1 genomic gene was PCR amplified from *Hordeum vulgare* cultivar Golden Promise (seed from Robbie Waugh, The James Hutton Institute, Invergowrie, Dundee DD2 5DA, Scotland UK, 2013) DNA using primers in Table 1. The HVEPF1 gene is annotated as MLOC67484 at Ensembl Plants (http://plants.ensembl.org/index.html) but is incorrectly translated in this prediction. We used FGENESH (http://www.softberry.com/) to generate an alternative translation which includes a putative signal sequence at the N-terminus. The PCR product was recombined pENTR/D/TOPO then by LR recombination into pCTAPi (Rohila et al., 2004, Plant J 38: 172-181) transformation vector under the control of the CaMV35S promoter, and introduced into *Arabidopsis thaliana* Col-0 background (NASC stock code N6673, obtained 2001) by floral dip (Clough & Bent, 1998, Plant J 16: 7 35-743). Transformation and expression of the transgene were confirmed by PCR and RT-PCR using the primers (shown in Table 1) of SEQ ID NO. 17 and SEQ ID NO. 18 for confirmation of hygromycin gene, and SEQ ID NO. 23 and SEQ ID NO. 24 for RT-PCR to measure levels of HVEPF1 cDNA.

TABLE 1

Primer sequences used for PCR and RT-qPCR detailed in the methods section of the manuscript.

| Gene | Forward | Reverse |
| --- | --- | --- |
| Hygromycin | ACTCACCGCG ACGTCTG (SEQ ID NO.17) | GCGCGTCTGC TGCTCCATA (SEQ ID NO.18) |
| Hv GAPDH | GTGAGGCTGG TGCTGATT (SEQ ID NO.19) | CGTGGTGCAG CTAGCATTTG AGAC (SEQ ID NO.20) |
| Hv Tubulin | AGTGTCCTGTC CACCCACTC (SEQ ID NO.21) | AGCATGAAGT GGATCCTTGG (SEQ ID NO.22) |
| HvEPF1 (qPCR) | GTGGAGGAGA AGAAGGATGG (SEQ ID NO.23) | ATGGAGCACT TGAAGCTGAC (SEQ ID NO.24) |
| HvEPF1 (vector construction) | CACCATGAAG AGGCACGGTC TT (SEQ ID NO.25) | CTAGCTGGAG GGGACGGGGT (SEQ ID NO.26) |

TABLE 2

Gene copy number data for all lines generated. Sample names followed by * indicate the transformed plant lines used in this study.

| Sample | Copies_Hyg |
| --- | --- |
| HvEPF1OE-1* | 5 |
| S10 | 5 |
| S11 | 5 |
| S22 | 2 |
| S25 | 2 |
| S9 | 2 |
| S2 | 2 |
| S12 | 1 |
| HvEPF1 OE-2* | 1 |
| S4 | 1 |
| HvEPF1 OE-3* | 1 |
| HvEPF1 OE-4* | 1 |

Figure 4:
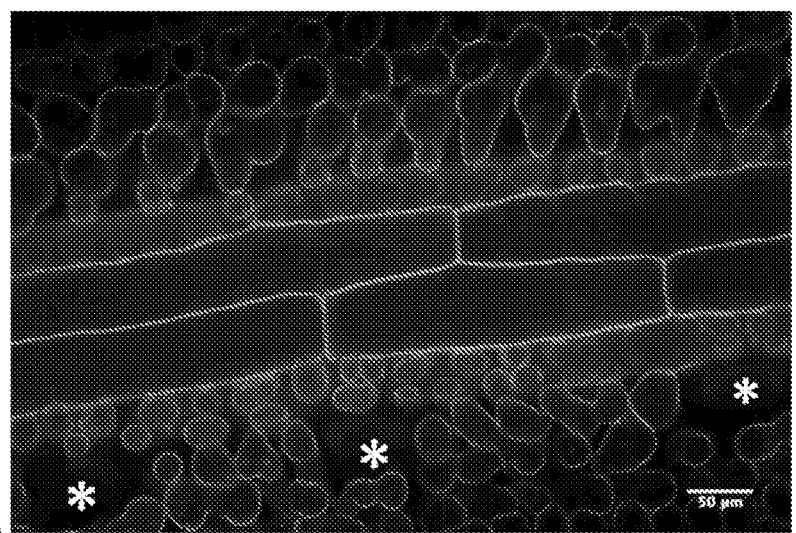
FIG. 4 shows cellular structure of HvEPF1OE stomatal complexes. (a) Representative propidium iodide stained confocal image of a Z-plane below the HvEPF1OE-1 abaxial epidermal surface. Yellow asterisks mark the location of the substomatal cavity under mature guard cells. (b) Higher Z-plane image of the same field of view as (a) to reveal position of stomata. White asterisks mark the location of arrested stomatal precursors and the lack of underlying substomatal cavities in (a).
Figure 4:
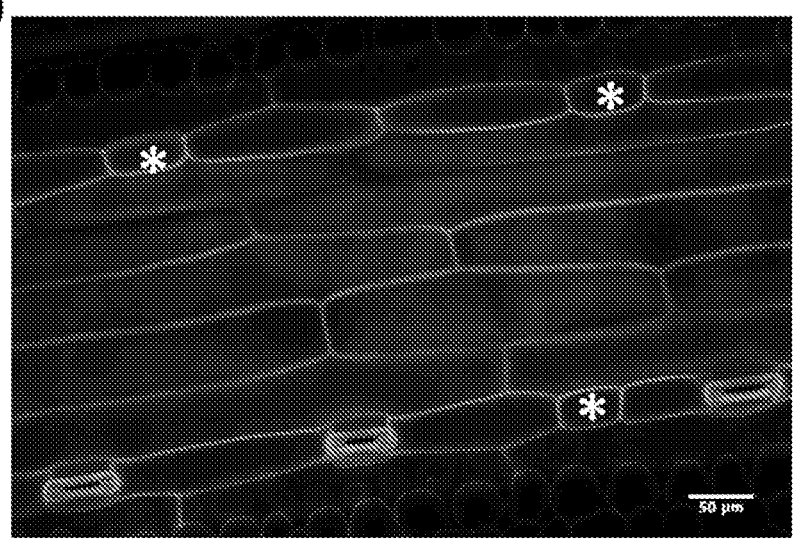
Figures 1, 9:
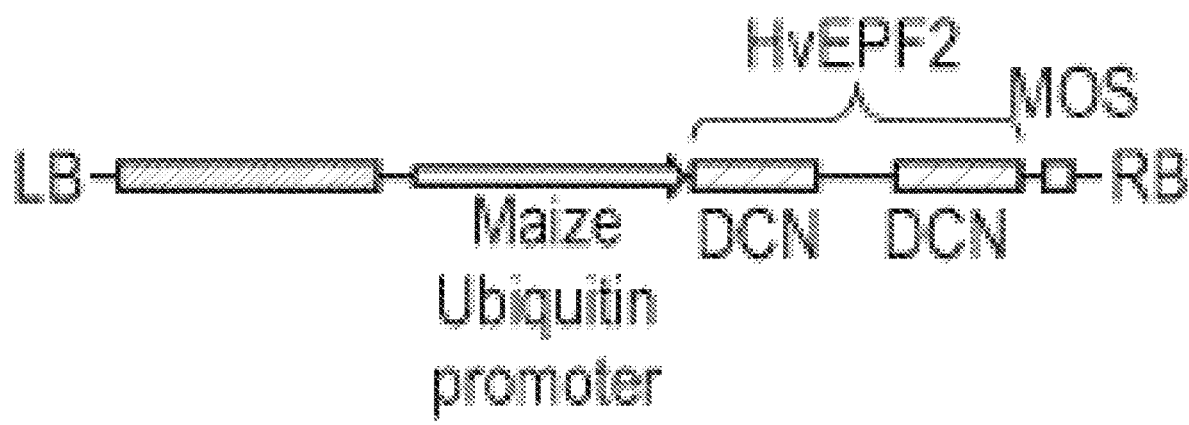
Figures 2, 3, 9:
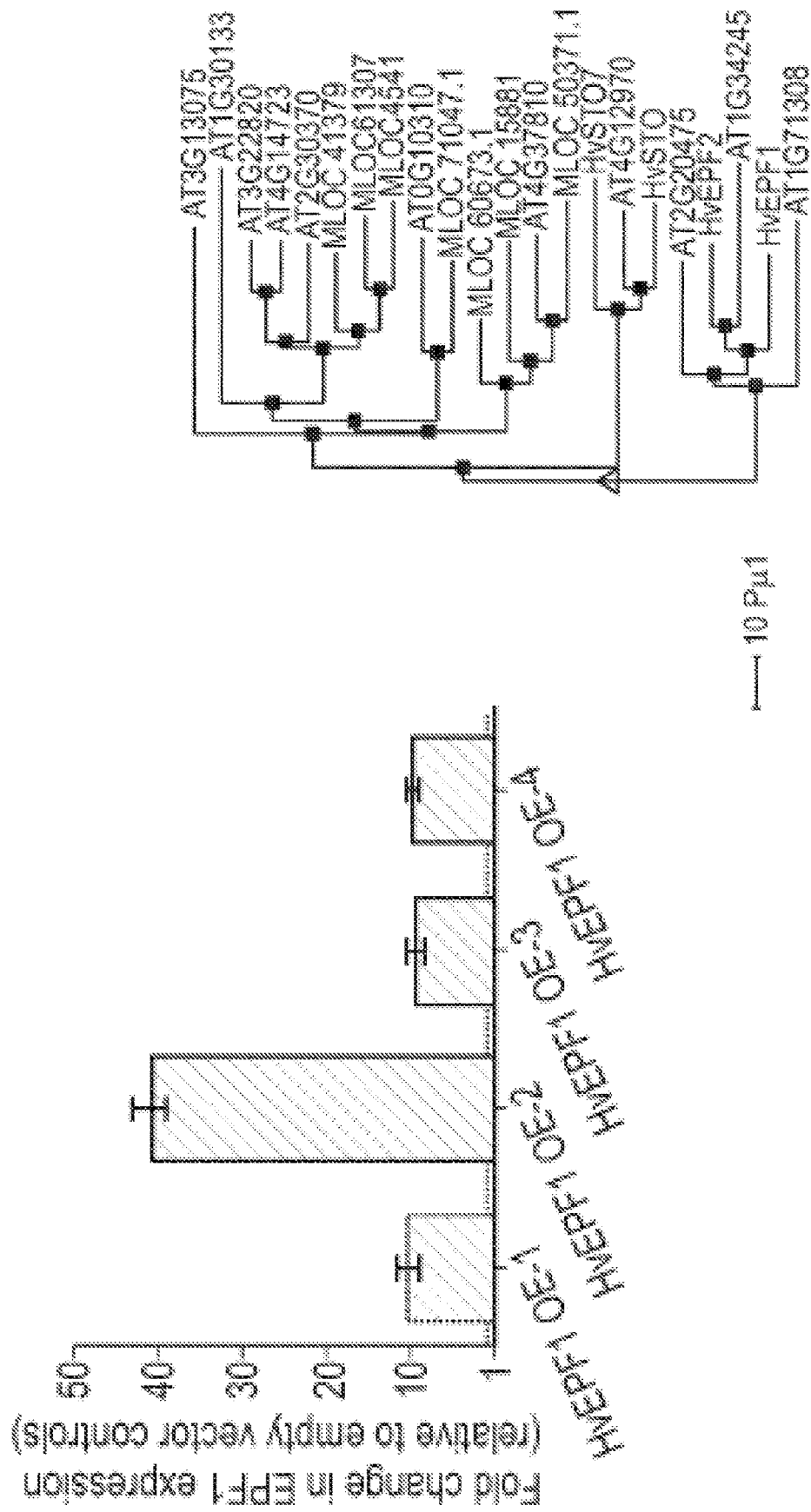
Figures 4, 9:
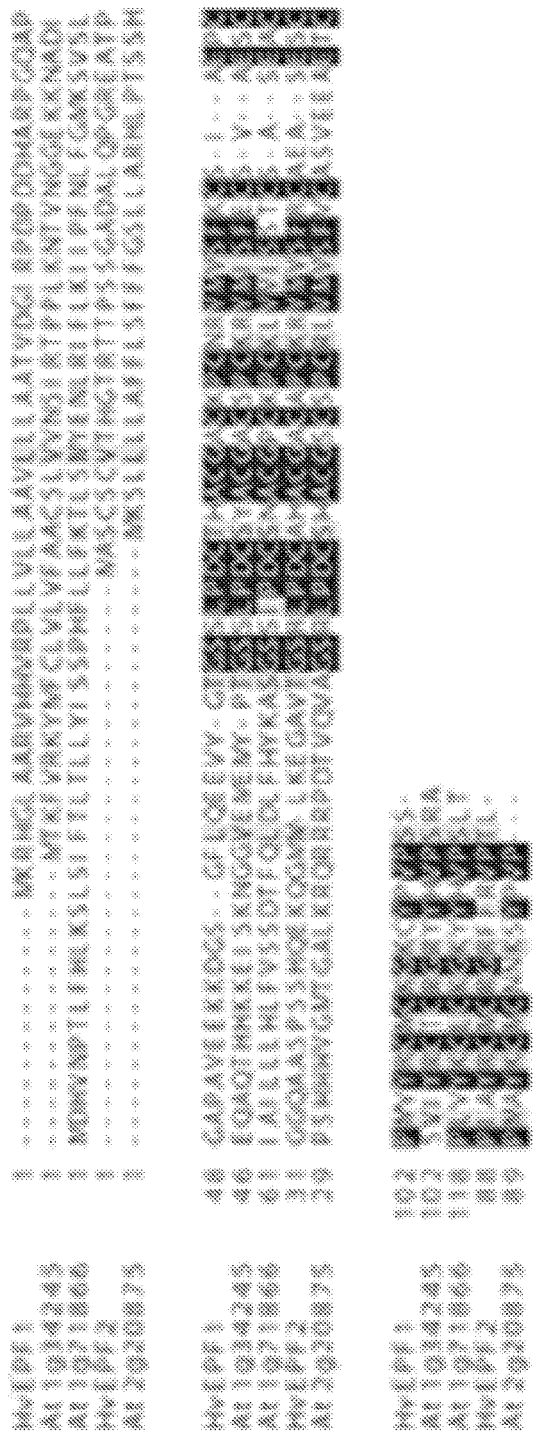
Figures 5, 9:
Figures 6, 9:
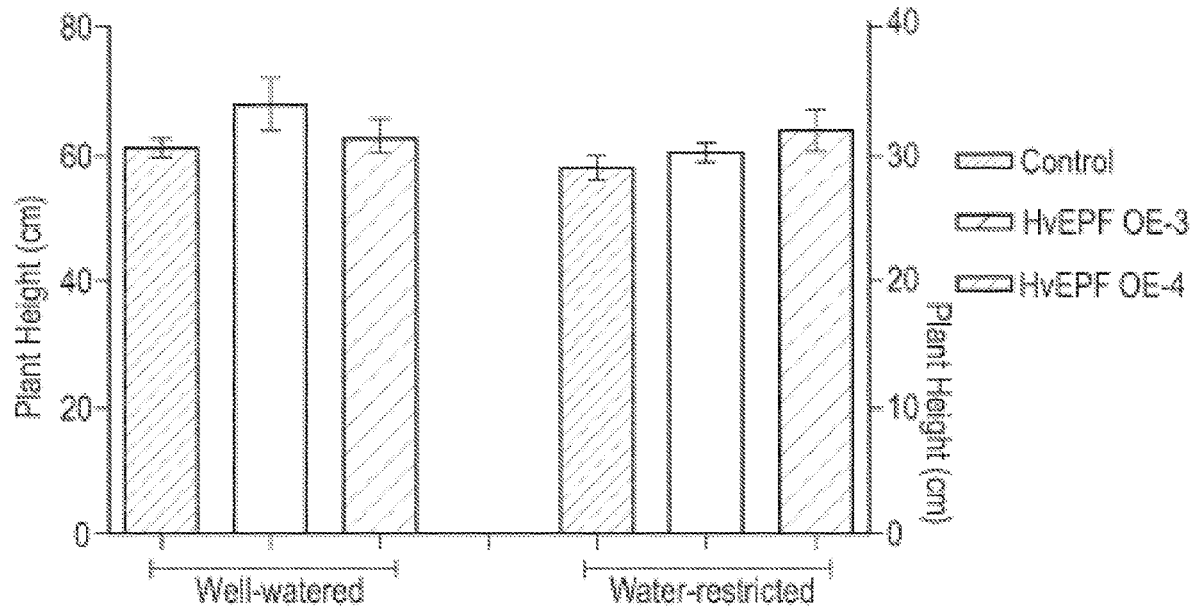

For barley transformation the HvEPF1 genomic gene was introduced by LR recombination into pBRACT214 gateway vector under the control of the maize ubiquitin promoter, adjacent to a hygromycin resistance gene under the control of a CaMV35S promoter (FIG. 9-4). Barley transformations were carried out in background Golden Promise (seed from Robbie Waugh, The James Hutton Institute, Invergowrie, Dundee DD2 5DA, Scotland UK, 2013) using the method described by Harwood et al. (Harwood et al., 2009, Methods Mol Biol 478:137-147). Plants harbouring just the hygromycin resistance cassette were regenerated alongside to produce 'empty-vector control' plants. Potentially transformed plants were regenerated on selective medium and T0 individuals genotyped to confirm gene insertion by PCR. Gene copy number was estimated by IDna Genetics Ltd (www.idnagenetics.com) using a PCR based method. HvEPF1 overexpression was confirmed by RT-qPCR of T2 generation plants (FIG. 9-6). Total RNA was extracted from 10 day old seedlings using Spectrum plant total RNA kit (Sigma, UK) and reverse transcribed using Maxima H Minus Reverse Transcriptase cDNA synthesis kit (Thermo Scientific). RT-qPCR was performed using a Rotor-Gene SYBR® Green PCR kit (Qiagen) with tubulin and GADPH used as housekeeping reference genes, with primers of SEQ. ID NO. 19-22 in Table 1. Three plants of each transformed line were amplified to confirm overexpression of the HvEPF1 gene. Fold induction values of gene expression were normalised to average $2^{\Delta Ct}$ values relative to empty-vector control samples.

Example 3: Plant Growth Conditions

For plant growth, seeds were surfaced sterilised in 50% vol/vol ethanol/bleach before being placed onto water saturated filter paper and placed into sealed Petri dishes in the appropriate growth chamber. *Arabidopsis* plants were grown in a controlled growth chamber (Conviron model MTPS120) at 22° C./16° C., 9 hours light, 150-200 µmol $m^{-2}$ $s^{-1}$, 15 hours dark, ambient [$CO_2$] and 60% humidity. *Arabidopsis* plants were kept well-watered throughout. Barley plants were grown in a MTPS120 growth chamber at 21° C./15° C., 11 hours light at 300 µmol·$m^{-2}$·$s^1$, 13 hours dark, ambient [$CO_2$] and 60% humidity. For plants grown under greenhouse conditions, temperature was set at 20° C./16° C., 12 hours light, ambient humidity, and supplementary lighting ensured a minimum of 200 µmol $m^{-2}$ $s^{-1}$ at bench level.

At 5 days post-germination individual barley seedlings were placed into 13 cm diameter pots containing homogenised M3 compost/perlite (4:1) with the addition of Osmocote. For initial phenotyping and physiological measurements (FIG. 2), 'well-watered' plants were maintained at 60% of soil saturation by daily weighing of pots. 'Water-restricted' plants (reported in FIG. 2d, FIG. 6 and FIG. 7) were maintained at 25% of maximum soil saturation.

Example 4: Microscopy and Cell Counts

For both *Arabidopsis* and barley, stomatal and epidermal cell counts were taken from the abaxial surface of mature, fully expanded leaves or cotyledons. Cell counts were taken from the widest section of the first true leaf avoiding the mid vein. Dental resin (Coltene Whaledent, Switzerland) was applied in the region of maximum leaf width and left to set before removing the leaf and applying clear nail varnish to the resin. Stomatal counts were determined from nail varnish impressions by light microscopy (Olympus BX51). 5 areas per leaf were sampled from 4-8 plants of each genotype and treatment. For epidermal imaging (FIG. 2b-d), mature leaves were excised and the central vein of the leaf cut away. Leaf tissue was then serially dehydrated in ethanol. Samples were then placed into modified Clarke's solution (4:1 ethanol to glacial acetic acid solution) then cleared in 50% bleach overnight.

For epidermal phenotyping, the second fully expanded mature leaf of seedlings were excised and a 3-5 cm strip midway along the proximodistal axis of these leaves were cut out. These leaf samples were then submerged in Clarke's solution (3:1 ethanol to glacial acetic acid solution). Following 1 hour of vacuum infiltration the samples were left in Clarke's solution for 24 hours for fixation. Once fixed the samples were transferred into 100% ethanol. Prior to imaging the leaf samples were cleared in 50% bleach solution overnight. The midrib of each sample was then excised and the remaining leaf sections mounted in deionised water on microscope slides for imaging. Samples were viewed by light microscopy (Olympus BX51) using differential interference contrast functionality. For confocal microscopy (FIG. 4a, FIG. 4b), barley samples were prepared as described (Wuyts et al., 2010, Plant Methods 6: 1-14) and viewed on a Olympus FV1000 using 20× UPlan S-Apo N.A. 0.75 objective, 543 nm laser, 555-655 nm emission and Fluorview software.

Example 5: Physiological Measurements

A LI-6400 portable photosynthesis system (Licor, Lincoln, Nebr.) was used to carry out infrared gas analysis (IRGA) on mature, fully expanded, leaves that were still attached to the plant. Relative humidity inside the IRGA chamber was kept at 60%-65% using self-indicating desiccant, flow rate was set at 300 $\mu mol \cdot s^{-1}$ and leaf temperature at 20° C. Reference [$CO_2$] was maintained at 500 ppm and light intensity at 200 $\mu mol \cdot m^{-2} \cdot s^{1}$. Plants were allowed to equilibrate for 40-45 minutes the IRGA chamber being matched at least every 15 minutes. Once readings were stable measurements were taken every 20 seconds for 5 minutes. For soil water content calculations, the weight of pots containing water saturated (100% water content) or oven dried (0%) compost mix was first determined. Pots were then maintained at either 60% or 25% soil water content by weighing and addition of the appropriate amount of water every two days.

Once plants had matured and dried down the plants were harvested, with the total number and weight of seeds per plant being recorded and the average seed weight being calculated. All above-ground vegetative tissue was dried in an oven at 80° C. for two days and then weighed to provide the dry weight. Harvest index (ratio of yield to above-ground biomass) was then calculated. Throughout the terminal drought experiment the light adapted quantum yield of photosystem II ($\phi$PSII) was measured daily for both well-watered and water-withheld plants. The most recent fully expanded leaf of the primary tiller was selected for the measurement at day 1 and the same leaf was then monitored throughout the experiment. Readings were taken using a FluorPen FP100 (Photon Systems Instruments). Following the onset of the drought treatment the pots were weighed every day and used to calculate the percentage of initial soil water content remaining. Well-watered controls were maintained at 60% soil water content.

Leaf relative water content was determined from excised leaves from well-watered or droughted and their fresh weight measured immediately and leaves were floated on water overnight and weighed to record the hydrated weight. They were oven-dried overnight and weighed to obtain their dry weight; the RWC was calculated using the following formula RWC (%)=(fresh weight−dry weight)/(hydrated weight−dry weight)*100.

For carbon isotope discrimination (FIG. 6d), δ13C was assessed from the flag leaf of 5 plants from each of the two watering regimes (well-watered and restricted-watered), as described previously (Hepworth et al., 2015, New Phytologist 208: 336-341).

Example 6: Statistical Analysis

All comparisons were performed on Graph Pad Prism software. The appropriate post-hoc tests were conducted once significance was confirmed using an ANOVA test and an alpha level of 0.05 or below as significant.

Figure 1:
FIG. 1 shows HvEPF1 shares sequence similarity with Arabidopsis EPF1 and EPF2, and can restrict Arabidopsis stomatal development. (a) Alignment of the putative HvEPF1 mature signalling peptide with members of the Arabidopsis EPF family of signalling peptides. Conserved cysteine residues are highlighted. Amino acid sequences for the mature peptide region were aligned using Multalin and displayed using Boxshade.
Figure 1:
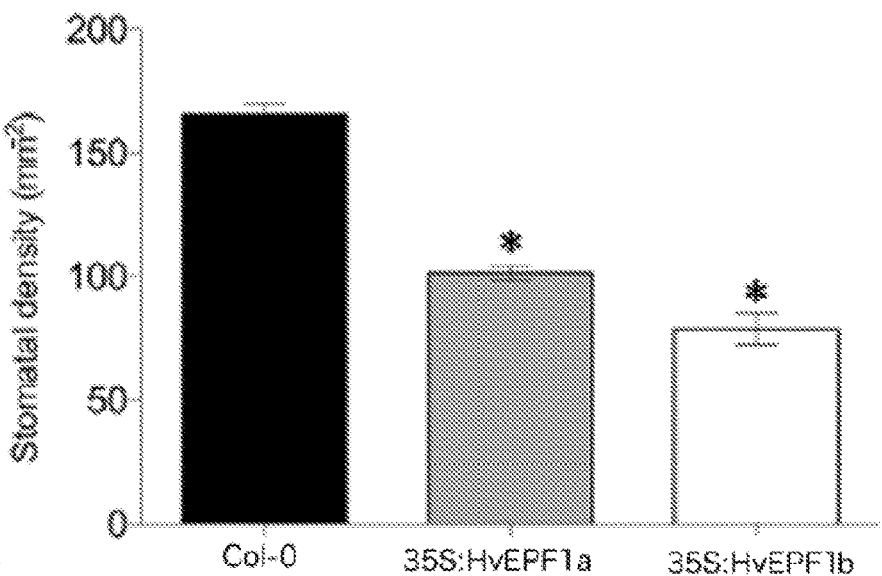
Figure 1:
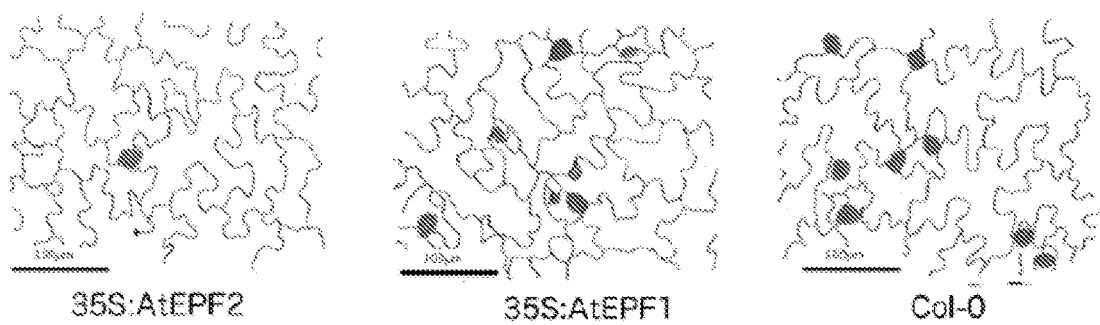
Figure 1:
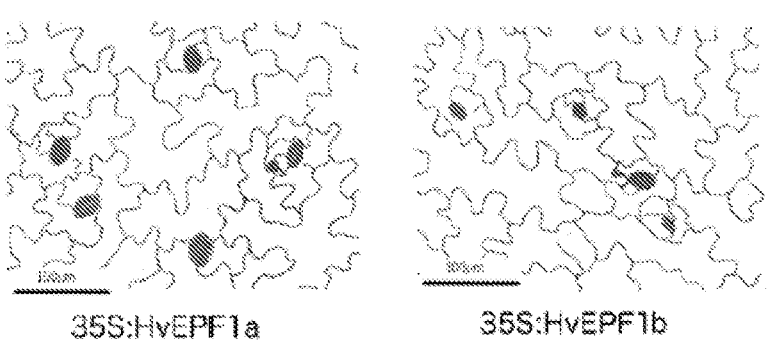

Example 7: Results 11 genes encoding putative EPF-like secreted peptides were identified in the barley genome sequence (IBSC, 2012) (FIG. 9-1). MLOC67484 which we refer to here as HvEPF1 encodes a peptide with extensive similarity to *Arabidopsis* epidermal patterning factors, and contains the 6 conserved cysteine residues (FIG. 1a) that are characteristic of *Arabidopsis* epidermal patterning factors (Ohki et al., 2011, Nature Communications 2: 512; Lau & Bergmann, 2012, Development 139: 3683-3692). Phylogenetic analysis of the encoded mature peptide sequence indicated that within the *Arabidopsis* EPF family, HvEPF1 is most closely related to the known inhibitors of stomatal development EPF1 and EPF2 which each contain two additional cysteine residues (FIG. 9-1). To confirm that this barley peptide gene could function in stomatal regulation, HvEPF1 was ectopically overexpressed in *Arabidopsis* under the control of the CaMV35S promoter. Analysis of cellular patterning on the epidermis of *Arabidopsis* plants overexpressing HvEPF1 confirmed that stomatal development had been disrupted; a phenotype similar to that observed on overexpression of *Arabidopsis* EPF1, namely a significant decrease in leaf stomatal density (FIG. 1b) and an increased number of arrested meristemoids (FIG. 1c) (Nara et al., 2007, Genes & Development 21: 1720-1725; Hara et al., 2009, Plant Cell Physiol 50: 1019-1031; Hunt & Gray, 2009, Curr Biol 19: 864-869). Next, barley plants ectopically over-expressing the epidermal patterning factor HvEPF1 under the control of a ubiquitin gene promoter were produced. Stomatal density (SD) was assessed from 13 transgenic lines of HvEPF1OE in the T1 generation under growth room conditions. The first leaves of seedling plants had SD ranging from approximately 70% down to <1% of that of control plants (transformed with the empty-vector) (FIG. 2a). Two lines were selected for further phenotyping: HvEPF1OE-(47%) and HvEPF1OE-(0.6%), which displayed approximately 47% and 0.6% of the SD of controls respectively. Significantly reduced leaf SD was observed in abaxial epidermal impressions (FIG. 2b) and unusually large patches of epidermis with an absence of stomates were seen in the leaves of HvEPF1O E (0.6%). Furthermore, arrested stomatal precursor cells were frequently observed in the mature, fully expanded, epidermis which were extremely rare in controls (black arrow in FIG. 2c).

Figure 2:
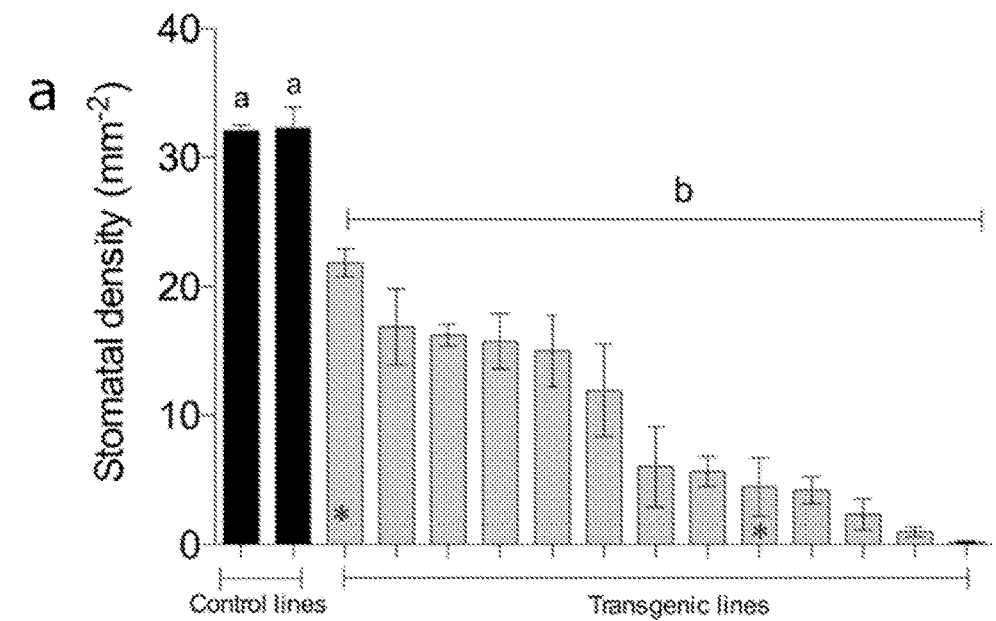
FIG. 2 shows over-expression of HvEPF1 in barley arrests stomatal development and reduces stomatal density. (a) The abaxial stomatal density (SD) of barley plants transformed to ectopically over-express HvEPF1 (grey bars) compared to control lines transformed with the empty-vector (black bars). All T1 generation HvEPF1 over-expressing lines demonstrated a significant reduction in SD in comparison to both control lines. Lines chosen for further phenotyping in T2 generations are indicated (asterisks) (b) Traced abaxial epidermal impressions of T1 generation control, HvEPF1OE-(47%) and HvEPF1OE-(0.6%) lines illustrating the reduction in SD. Red dots denote positions of stomatal complexes. (c) Abaxial epidermal micrographs of HvEPF1OE plants. Black arrow indicates arrested stomatal precursor cell. N=4-8 plants (Tukeys multiple comparisons test after one-way ANOVA). Error bars represent SE.
Figure 2:
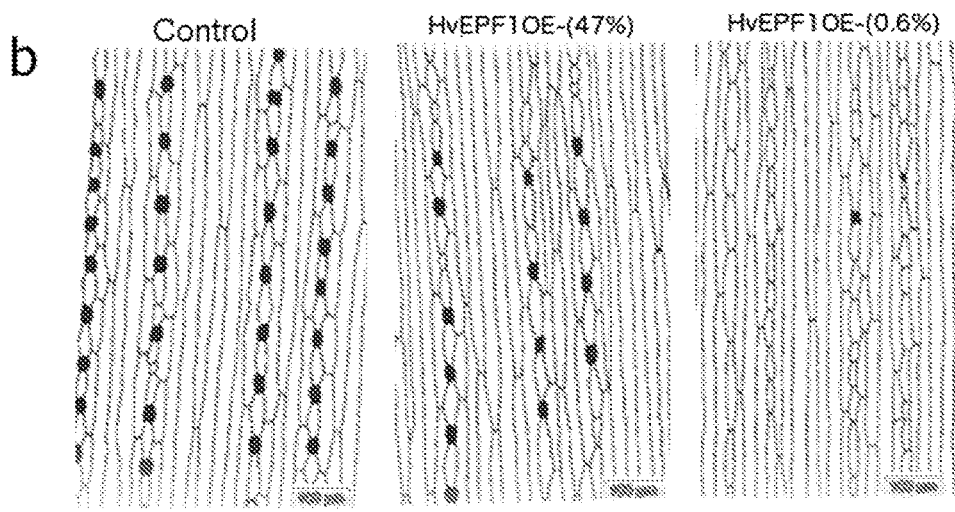
Figure 2:
Figure 2:
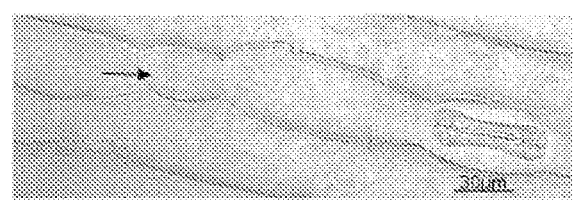

For more detailed physiological analysis, homozygous barley lines harbouring a single copy of the transgene (Table 1) were isolated (referred to as HvEPF1OE-1 and HvEPF1OE-2 and indicated by the left and right black asterisks in FIG. 2a respectively). T2 generation plants were grown under controlled chamber conditions and the abaxial SD of the second true leaf was significantly reduced by approximately 52% and 56% of controls for HvEPFOE-1 and HvEPFOE-2 respectively (FIG. 3a). In addition, the stomates that formed were smaller; guard cell length was significantly reduced in both HvEPF1OE lines (FIG. 3b). We also observed a small increase in epidermal pavement cell density, perhaps due to the smaller and less frequent stomata, however, this was not significant (FIG. 3c). These differences in cell densities combined to produce large reductions in stomatal index (SI; stomatal density as a percentage of all cells on the epidermis). SI of HvEPF1OE plants was reduced to approximately 50% of control values (FIG. 3d). Again we observed a significant increase in the number of arrested stomatal precursor cells in HvEPF1OE barley leaves (as shown in FIG. 2). To calculate whether the number of arrested stomatal precursor cells could entirely account for the observed reductions in SD we calculated the 'stomatal lineage cell index' (the percentage of stomata and arrested stomatal lineage cells compared to all cells on the epidermis). This indicated that if all arrested stomatal precursor cells were to have progressed normally to produce stomata, there would still be a significant reduction in stomatal index, suggesting that both the priming of cells to enter the stomatal lineage, and the progression of cells through the stomatal lineage are compromised by HvEPF1 overexpression (FIG. 3e).

Having shown that HvEPF1 can effectively regulate the frequency of stomatal development, we next explored whether other aspects of HvEPF1OE leaves were affected. First, we investigated the internal structure of leaves. Stacked confocal images were produced to visualise HvEPF1OE substomatal cavities. This revealed similar internal cellular structures, and mature HvEPF1OE stomatal complexes had guard cells positioned normally above substomatal cavities as in controls (yellow asterisks, FIG. 4a). However, on the same images, a lack of cavity formation was observed under the arrested stomatal precursor cells in both HvEPF1OE-1 and HvEPF1OE-2 lines (white asterisks, FIG. 4b).

Figure 5A:
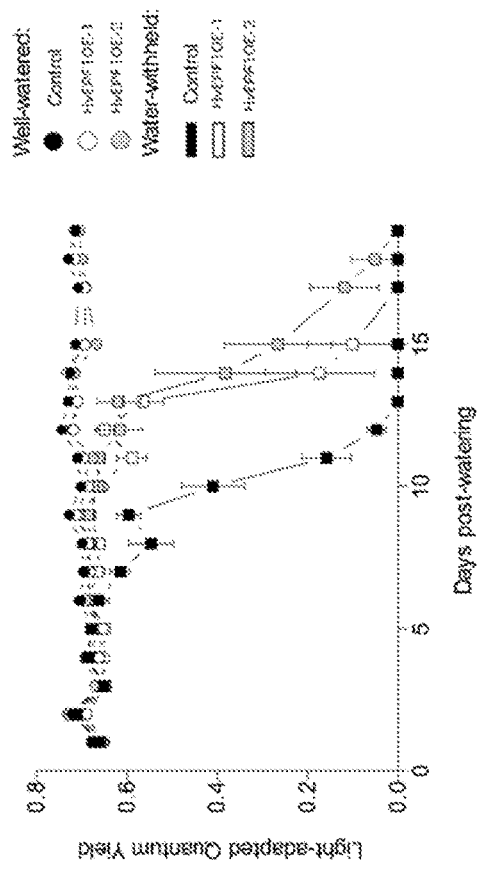
FIG. 5 shows reducing barley stomatal density enhances drought tolerance though conserving soil and plant water content. (a) 5 week old HvEPF1OE-1 and HvEPF1OE-2 barley plants maintain significantly higher soil water content in comparison to control plants when water is withheld from days 2-14. (b) Both HvEPF1OE-1 and HvEPF1OE-2 lines show significantly higher light adapted quantum yields (φPSII) from 10 to 14 days after water was withheld (square symbols; plants from same experiment as (a)). There were no significant differences between φPSII of well-watered plants (circular symbols). (c) Relative water content (RWC) of barley leaves from HvEPF1OE lines was significantly higher than controls after 6 days without watering. There were no differences in RWC between well-watered plants. (d) Photograph of representative plants to illustrate enhanced turgor maintenance in HvEPF1OE-1 and HvEPF1OE-2 on day 6 of water-withheld conditions. N=5 plants, asterisk indicates significance to at least $P<0.05$ (Dunnett's tests after one-way ANOVA for each watering group). Error bars represent SE.
Figure 5B:
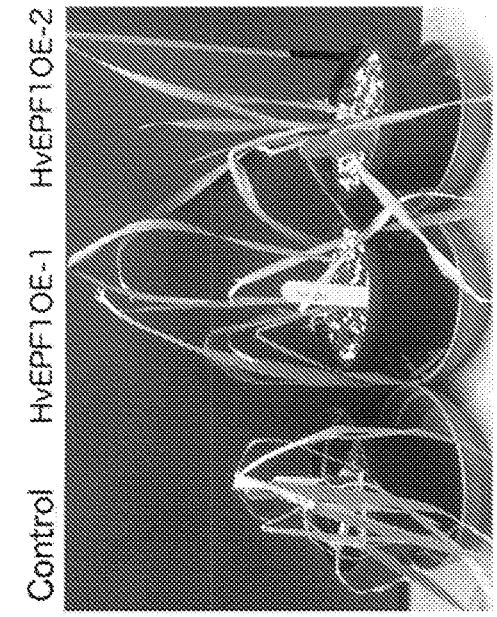
Figure 5C:
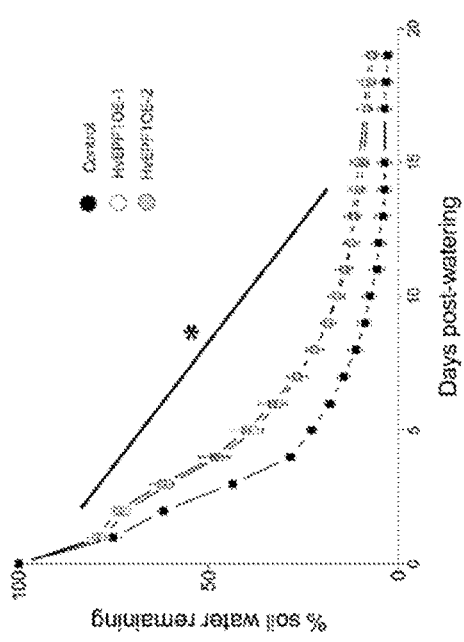
Figure 5D:
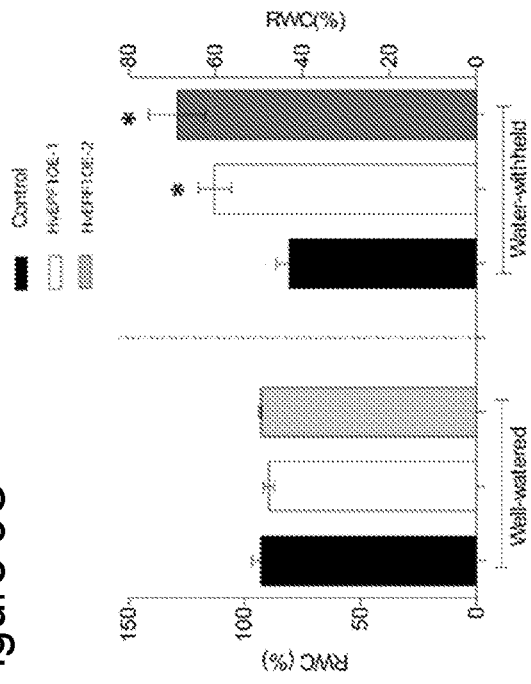

To more fully investigate the effect of reduced SD on drought tolerance, T2 generation plants were grown in a greenhouse with natural and supplemental lighting and temperature control. 5-week-old HvEPF1OE-1, HvEPF1OE-2 and control plants were subjected to a terminal drought experiment alongside a parallel set of plants that were kept well-watered (maintained at 60% maximum soil water content). Pots were weighed at the same time each day and this was used to calculate soil water loss. The results of this experiment revealed that both transformed barley lines lost water much more slowly and exhibited significantly greater soil water conservation in their pots from day 2 until day 14 under water-withheld conditions (FIG. 5a). Chlorophyll fluorescence measurements were used to measure any reductions in photosystem II efficiency, an indicator of plant stress. The light adapted quantum yield of photosystem II ($\phi_{PSII}$) was measured daily for both well-watered and water-withheld plants throughout the terminal drought experiment. There were no differences between the $\phi_{PSII}$ of HvEPF1OE and control plants at the start of the experiment or between genotypes under well-watered conditions indicating that the reduced stomatal density of the HvEPF1OE leaves was not restricting photosystem II efficiency. Remarkably however, the HvEPF1OE plants that had water withheld, displayed significantly enhanced rates of $\phi_{PSII}$ versus water-withheld controls from day 10 until day 14; both HvEPF1OE-1 and HvEPF1OE-2 plants maintained their photosystem II efficiency for approximately 4 days longer than controls under severe drought conditions. On day 6 of terminal drought, leaf samples were taken for leaf relative water content (RWC) estimation. This result indicated no significant difference in leaf RWC between controls and HvEPF1OE plants under well-watered conditions. However, under water-withheld conditions, both HvEPF1OE lines displayed significantly higher levels of leaf RWC versus controls (FIG. 5c), indicating an enhanced ability to retain water in their leaves under drought conditions. In addition, the HvEPF1OE plants were less susceptible to wilting and appeared visibly more 'drought tolerant' on day 6 of water-withheld conditions (FIG. 5d).

Figure 6A:
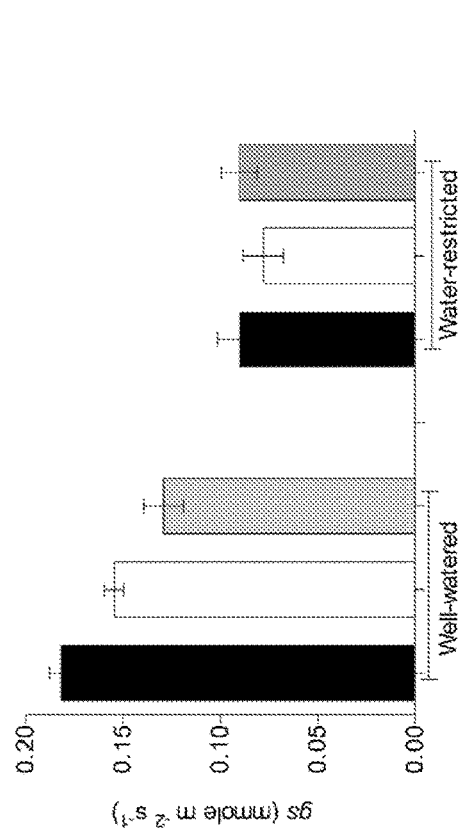
FIG. 6 shows reducing barley stomatal density lowers stomatal conductance and enhances water use efficiency. (a) Under well-watered conditions a significant decrease in rate of carbon assimilation was observed in both HvEPF1OE lines. Under water-restricted conditions there was no difference in assimilation. (b) Stomatal conductance (gs) was significant decreased in HvEPF1OE lines grown under well-watered conditions in comparison to controls. Under water-restricted conditions there was no difference in gs. (c) Under well-watered conditions, a significant improvement in intrinsic water use efficiency (iWUE) was observed in the HvEPF1OE-2 line when compared to control plants. Under water-restricted conditions there was no difference in iWUE. (d) Carbon isotope discrimination revealed a significant improvement in water use efficiency of the HvEPF1OE-2 barley line under well-watered conditions. Under water-restricted conditions, both HvEPF1OE lines displayed significantly improved water use efficiency in comparison to controls. N=5 plants, asterisk indicates significance to at least $P<0.05$ (Dunnett's tests after one-way ANOVA for each watering group). Error bars represent SE.
Figure 6B:
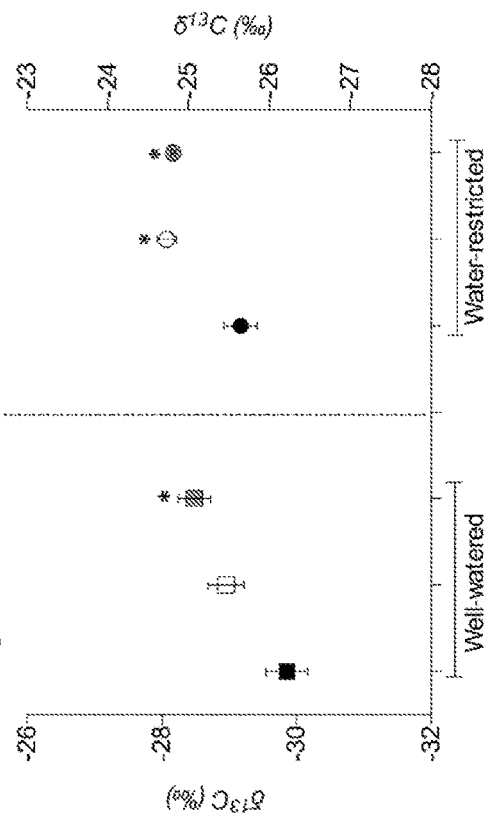
Figure 6C:
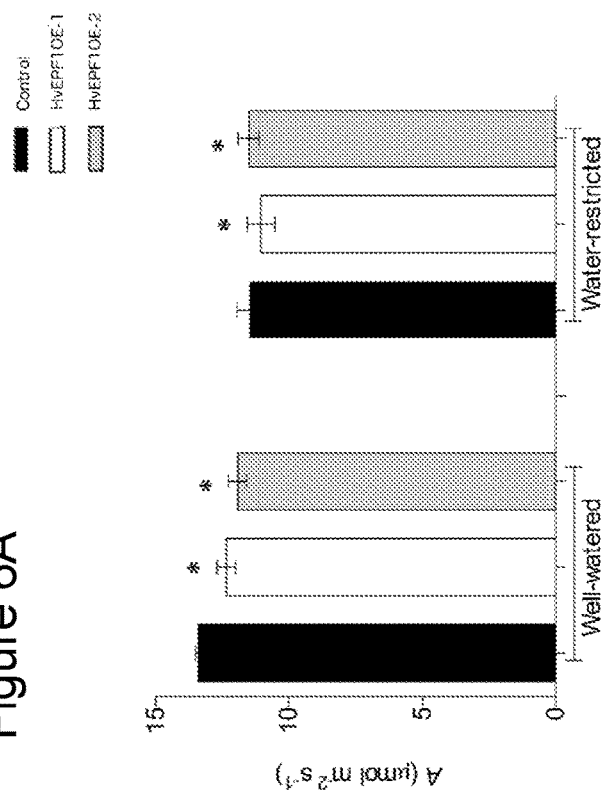
Figure 6D:
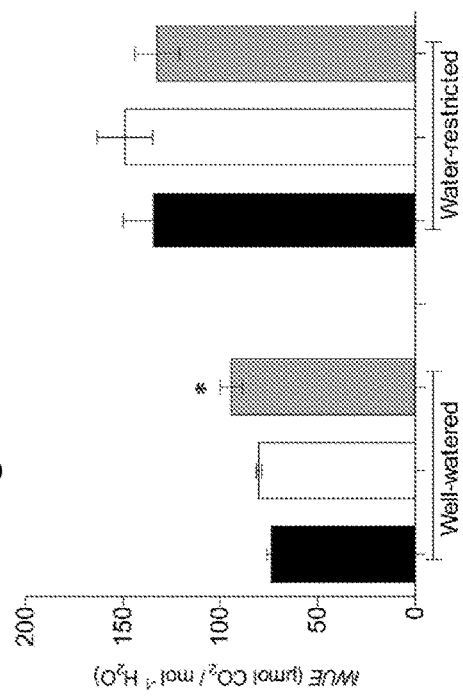
Figure 7A:
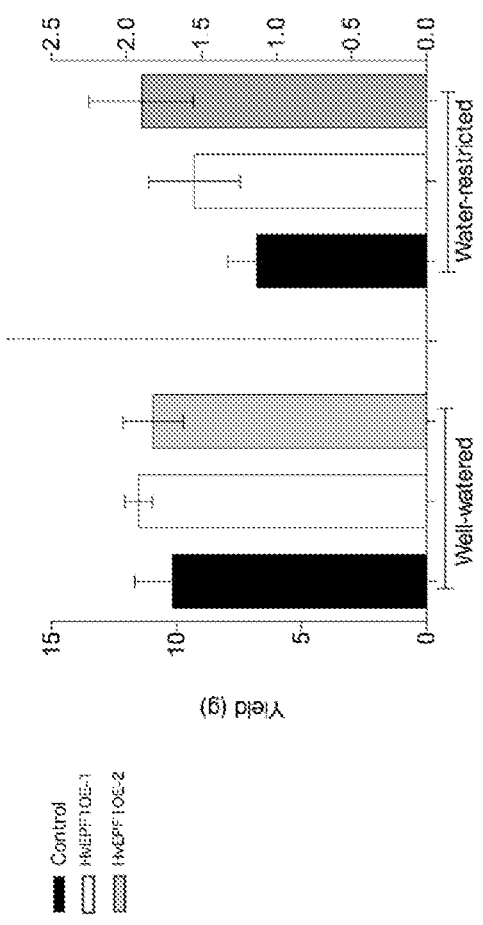
FIG. 7 shows reducing stomatal density in barley has no deleterious effect on yield. No significant differences in (a) seed number, (b) total weight of seed per plant, (c) average weight of individual seeds, (d) harvest index (the ratio of yield to total shoot biomass) were observed between HvEPF1OE-1, HvEPF1OE-2 and control plants under either watering condition. N=5 plants. Error bars represent SE.
Figure 7B:
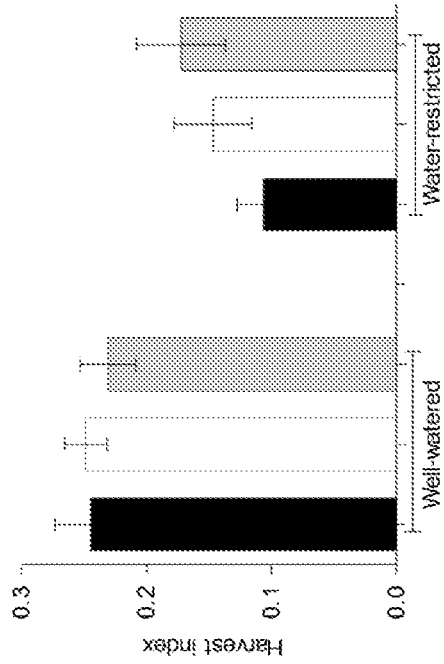
Figure 7C:
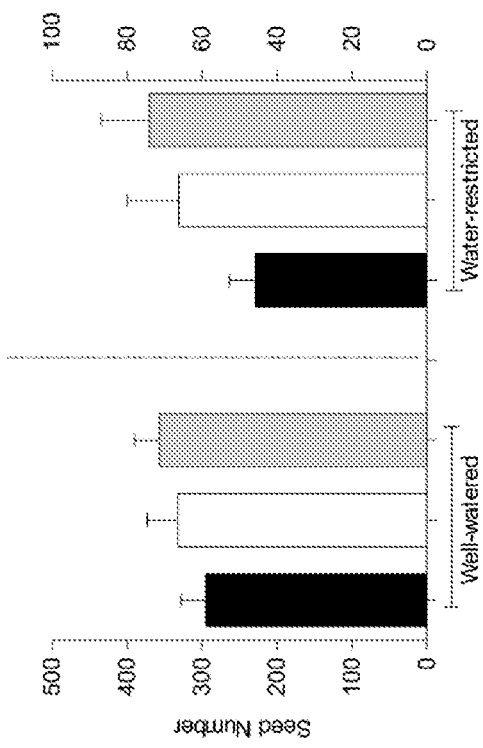
Figure 7D:
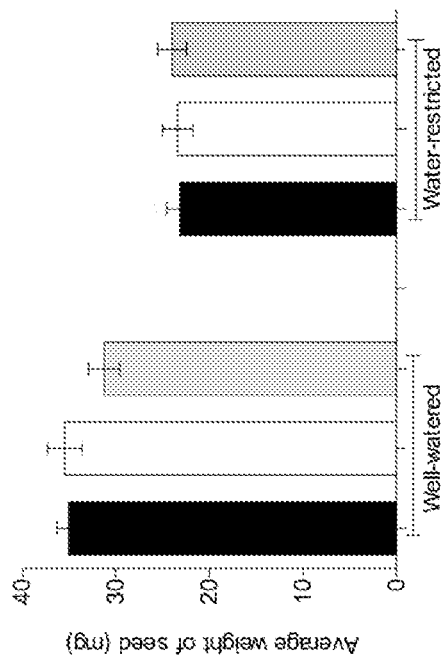

In a separate greenhouse experiment, we investigated whether the reduced SD of HvEPF1OE barley plants could confer any advantage to growth under conditions of limited water availability (rather than on complete withholding of water as above). HvEPF1OE-1, HvEPF1OE-2 and controls plants were grown under well-watered (60% soil water content) and water-restricted (25% soil water content) in parallel under controlled greenhouse conditions. This water-restricted regime was severe enough to attenuate the growth rate of the barley plants but not severe enough to cause visible signs of wilting (FIG. 9-2). Stomatal density and steady state gas exchange measurements were taken from the sixth fully expanded leaf of the primary tiller of the mature plants. This revealed that SD and photosynthetic assimilation were significantly reduced in comparison to controls in both HvEPF1OE lines under well-watered conditions. On these leaves the SD of HvEPF1 OE-1/2 were 24% and 12% of control values respectively. There was a significant decrease in A in both lines under well watered conditions but no significant differences in A between HvEPF1OE or control plants that had been grown under water-restriction (FIG. 6a). In addition, there was a significant reduction in stomatal conductance (gs) between HvEPF1OE and control plants within the well-watered treatment group and a reduction in the gs of all plants within the water-restricted treatment (FIG. 6b). As a result of the large reductions in gs and relatively small reductions in A, intrinsic (iWUE) was calculated to be significantly increased in the HvEPF1OE-2 line under well-watered conditions. There was no increase in iWUE observed in either HvEPF1OE line under water-restricted conditions (FIG. 6c). After 11 weeks of drought, WUE across the lifetime of the barley plants was then assessed by delta-carbon isotope analysis. This revealed that, under water-restriction, both HvEPF1OE lines displayed lower levels of $^{13}C$ discrimination and thus a greater level of WUE. In agreement with the gas exchange results, only HvEPF1OE-2 plants (which had more severely reduced SD) displayed increased WUE under well-watered conditions (FIG. 6d).

Figure 3:
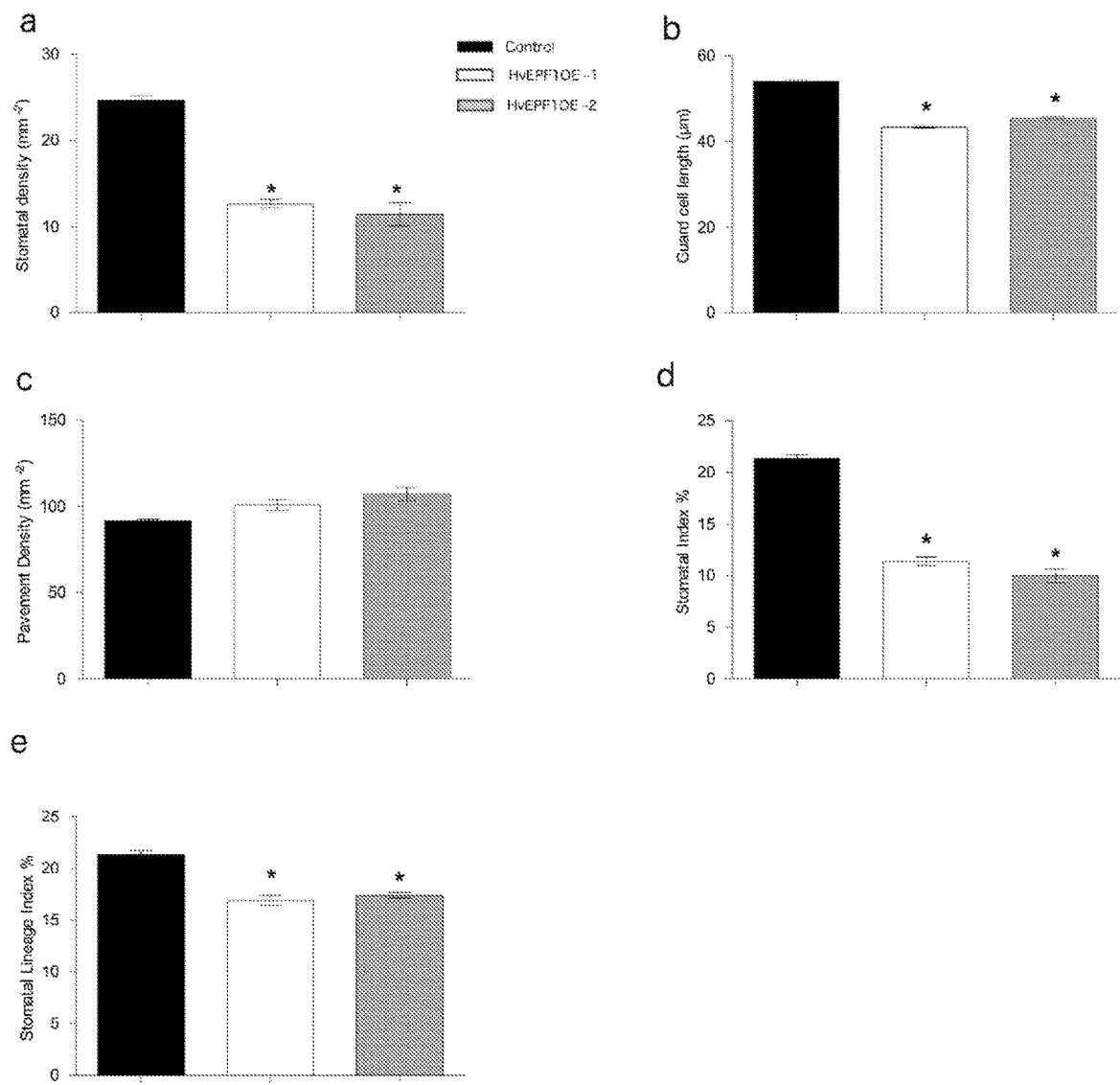
FIG. 3 shows stomatal characteristics of barley plants overexpressing HvEPF1. (a) Abaxial stomatal densities of HvEPF1 overexpressing T2 barley lines harbouring a single copy of the transgene are significantly decreased. HvEPF1OE-1 (white bars) and HvEPF1OE-2 (grey bars) compared to control lines (black bars). (b) Guard cell length is significantly decreased in both HvEPF1OE lines. (c) Pavement cell density is similar to that of the control in both HvEPF1OE lines. (d) Stomatal index is significantly decreased in both HvEPF1OE lines. (e) Stomatal lineage index (the ratio of stomata and arrested stomatal precursor cells to the total number of epidermal cells) is significantly decreased in both HvEPF1OE lines. N=5 plants, asterisks indicate $P<0.05$, (Dunnett's test after one-way ANOVA). Error bars represent SE.
Figures 7, 9:
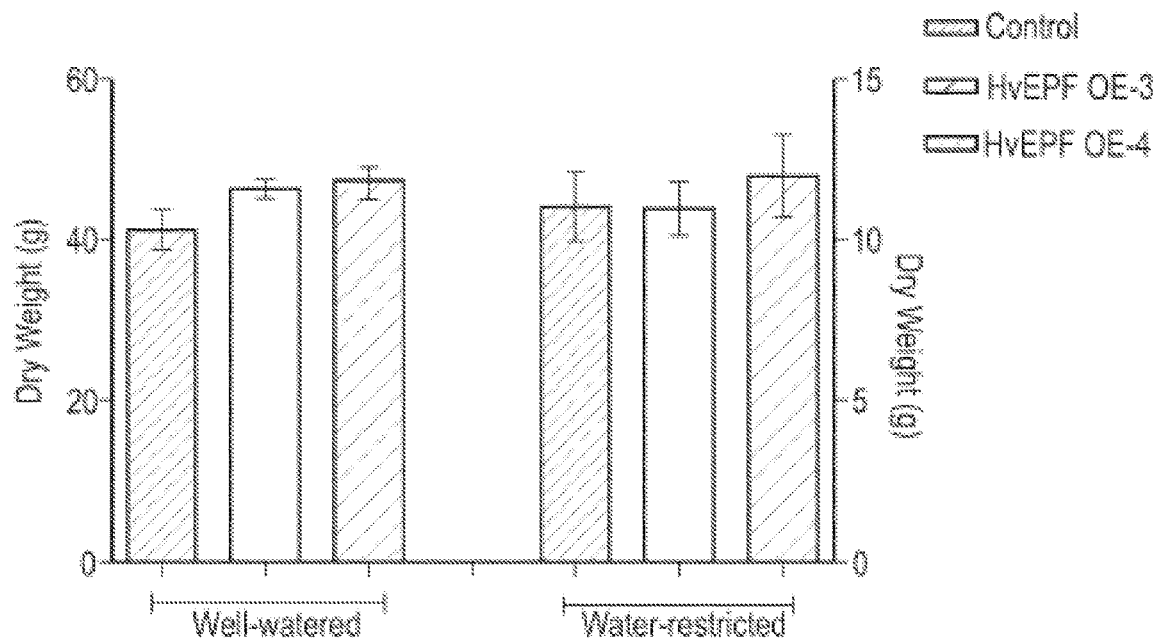

Finally, to assess the impact of reduced SD on barley yield and biomass, plants were left to grow under the well-watered and water-restricted regimes described above until plant peduncles had lost colour. At this point plants were allowed to dry and were then harvested. Analysis of the grain yield suggested that a reduction in SD did not have a deleterious effect on seed number, seed weight, the average weight of seed, nor the harvest index (the ratio of above ground biomass to seed weight) under either watering condition (FIG. 7 a-d). Interestingly, under water-restricted conditions, a trend towards increased seed number and yield was evident in both HvEPF1OE lines. In addition, no differences in plant height nor above ground biomass were found between any of the barley lines under either watering regime (FIGS. 9-3, 9-4).

Example 8: Alignments of EPF1 Orthologues

Figure 8A:
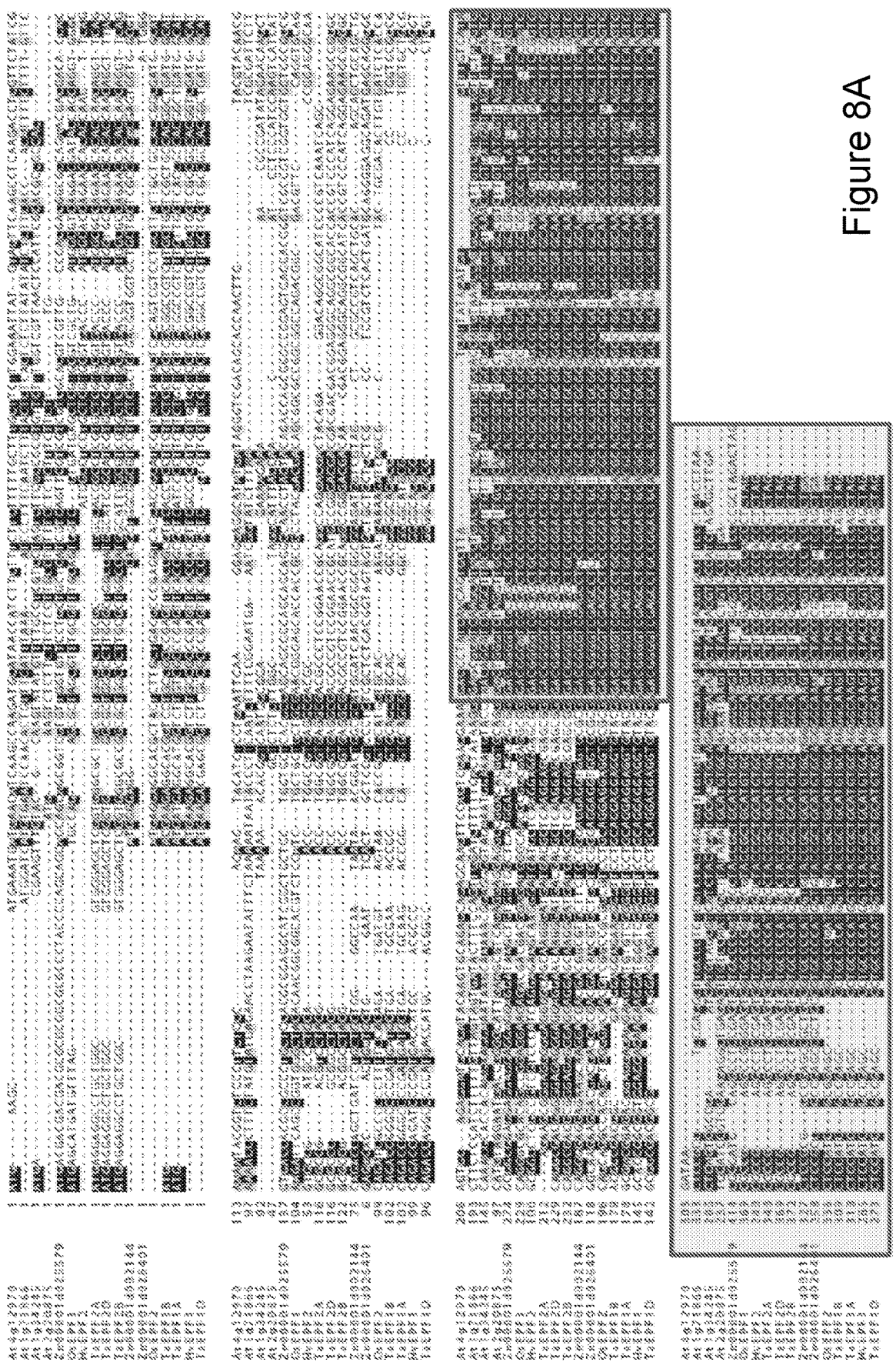
FIG. 8 shows an alignment of predicted EPF1/2 like cDNAs from *Arabidopsis thaliana* (At), *Triticum aestivum* (Ta), *Oryza sativa* (Os), *Hordeum* vulgarum (Hv) and *Zea mays* (Zm) (Panel A). Active peptide sequence is indicated (shaded box).

Predicted EPF1/2 like cDNAs from *Arabidopsis thaliana* (At), *Triticum aestivum* (Ta), *Oryza sativa* (Os), *Hordeum vulgarum* (Hv) and *Zea mays* (Zm) were aligned in silico and are shown in FIG. 8A. Conserved active peptide sequence is highlighted (shaded box).

Figure 8B:
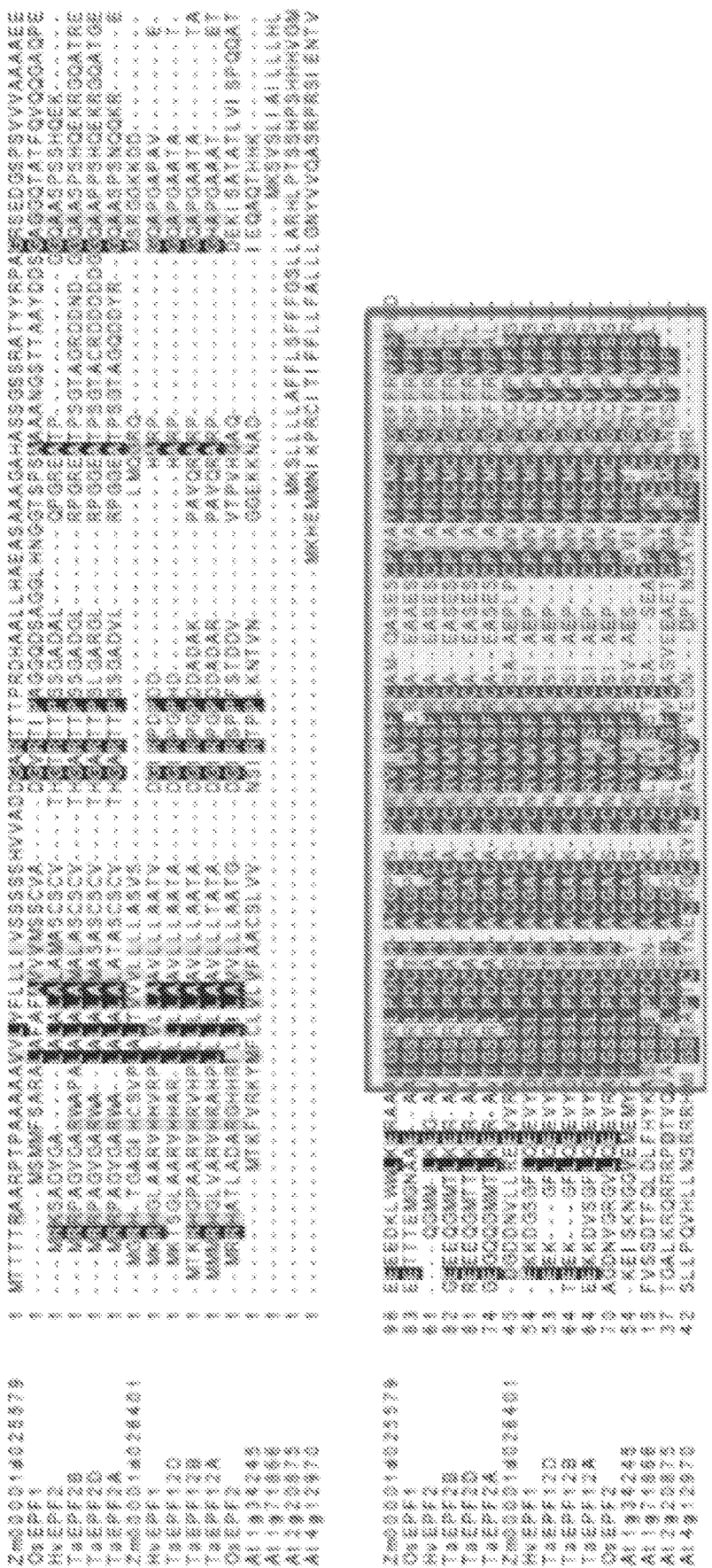

Deduced EPF1/2 like proteins from *Arabidopsis thaliana* (At), *Triticum aestivum* (Ta), *Oryza sativa* (Os), *Hordeum vulgarum* (Hv) and *Zea mays* (Zm) were aligned and are shown in FIG. 8B. Conserved active region of the peptide is highlighted (shaded box). Cysteine residues unique to stomatal density altering EPFs are indicated with an asterisk.

Percentage sequence identity of EPF2 proteins relative to HvEPF1 (SEQ ID NO: 8) were calculated and are shown in Table 3.

TABLE 3

Percentage identity of EPF proteins

| | Zm00001d 025579 | OsEPF1 | HvEPF2 | TaEPF2B | TaEPF2D | TaEPF2A | At2g20875 | At1g71866 | At1g34245 |
|---|---|---|---|---|---|---|---|---|---|
| Zm00001d 025579 | 100 | 86.27 | 84.31 | 84.31 | 84.31 | 82.35 | 61.54 | 47.06 | 60.78 |
| OsEPF1 | 86.27 | 100 | 86.27 | 86.27 | 86.27 | 82.35 | 64.71 | 48.98 | 61.22 |
| HvEPF2 | 84.31 | 86.27 | 100 | 100 | 100 | 96.08 | 60.78 | 48.98 | 63.27 |
| TaEPF2B | 84.31 | 86.27 | 100 | 100 | 100 | 96.08 | 60.78 | 48.98 | 63.27 |
| TaEPF2D | 84.31 | 86.27 | 100 | 100 | 100 | 96.08 | 60.78 | 48.98 | 63.27 |
| TaEPF2A | 82.35 | 82.35 | 96.08 | 96.08 | 96.08 | 100 | 60.78 | 48.98 | 61.22 |
| At2g20875 | 61.54 | 64.71 | 60.78 | 60.78 | 60.78 | 60.78 | 100 | 54 | 56 |
| At1g71866 | 47.06 | 48.98 | 48.98 | 48.98 | 48.98 | 48.98 | 54 | 100 | 60.78 |
| At1g34245 | 60.78 | 61.22 | 63.27 | 63.27 | 63.27 | 61.22 | 56 | 60.78 | 100 |
| Zm00001d 002144 | 61.54 | 60.78 | 62.75 | 62.75 | 62.75 | 60.78 | 65.38 | 62 | 72 |
| Zm00001d 026401 | 61.54 | 60.78 | 62.75 | 62.75 | 62.75 | 60.78 | 65.38 | 62 | 72 |
| OsEPF2 | 62 | 61.22 | 63.27 | 63.27 | 63.27 | 63.27 | 68 | 62 | 70 |
| HvEPF1 | 60 | 61.22 | 63.27 | 63.27 | 63.27 | 63.27 | 64 | 62 | 66 |
| TaEPF12D | 60 | 61.22 | 63.27 | 63.27 | 63.27 | 63.27 | 64 | 62 | 66 |
| TaEPF12B | 60 | 61.22 | 63.27 | 63.27 | 63.27 | 63.27 | 64 | 62 | 66 |
| TaEPF12A | 58 | 59.18 | 61.22 | 61.22 | 61.22 | 61.22 | 62 | 64 | 68 |

| | Zm00001d 002144 | Zm00001d 026401 | OsEPF2 | HvEPF1 | TaEPF12D | TaEPF12B | TaEPF12A |
|---|---|---|---|---|---|---|---|
| Zm00001d 025579 | 61.54 | 61.54 | 62 | 60 | 60 | 60 | 58 |
| OsEPF1 | 60.78 | 60.78 | 61.22 | 61.22 | 61.22 | 61.22 | 59.18 |
| HvEPF2 | 62.75 | 62.75 | 63.27 | 63.27 | 63.27 | 63.27 | 61.22 |
| TaEPF2B | 62.75 | 62.75 | 63.27 | 63.27 | 63.27 | 63.27 | 61.22 |
| TaEPF2D | 62.75 | 62.75 | 63.27 | 63.27 | 63.27 | 63.27 | 61.22 |
| TaEPF2A | 60.78 | 60.78 | 63.27 | 63.27 | 63.27 | 63.27 | 61.22 |
| At2g20875 | 65.38 | 65.38 | 68 | 64 | 64 | 64 | 62 |
| At1g71866 | 62 | 62 | 62 | 62 | 62 | 62 | 64 |
| At1g34245 | 72 | 72 | 70 | 66 | 66 | 66 | 68 |
| Zm00001d 002144 | 100 | 100 | 94 | 90 | 90 | 90 | 88 |
| Zm00001d 026401 | 100 | 100 | 94 | 90 | 90 | 90 | 88 |
| OsEPF2 | 94 | 94 | 100 | 96 | 96 | 96 | 94 |
| HvEPF1 | 90 | 90 | 96 | 100 | 100 | 100 | 98 |
| TaEPF12D | 90 | 90 | 96 | 100 | 100 | 100 | 98 |
| TaEPF12B | 90 | 90 | 96 | 100 | 100 | 100 | 98 |
| TaEPF12A | 88 | 88 | 94 | 98 | 98 | 98 | 100 |

Example 9: Improved Drought Tolerance and WUE without Reductions in Grain Yield Here the identification and characterization of a functional barley EPF orthologue, named HvEPF1 is reported. HvEPF1, acts in a similar way to the *Arabidopsis* EPF1 and EPF2 signaling peptides to limit entry to and progression through the stomatal cell lineage. Overexpression of the barley HvEPF1 transcript in *Arabidopsis* led to a significant reduction in SD indicating a level of conservation in peptide function between monocots and dicots. The overexpression of HvEPF1 in barley led to severe reductions in both stomatal formation, and in the entry of epidermal cells into the stomatal lineage.

Without wishing to be bound by any particular theory the frequent presence of arrested stomatal precursor cells on the epidermis of both *Arabidopsis* and barley HvEPF1OE plants (FIGS. 1c and 2b) suggests that the mode of action of HvEPF1 is most similar to that of *Arabidopsis* EPF1, which generates a similar epidermal phenotype when overexpressed (Nara et al., 2007; Hara et al., 2009). That is, stomatal precursors enter the developmental lineage but become arrested before the final symmetric cell division and maturation of the stomatal complex. These HvEPF1OE oval-shaped arrested cells appear to halt their development at a meristemoid-like or early guard mother cell stage, prior to transition into mature guard mother cells. Thus, in addition to entry to the stomatal lineage, the transition to a mature guard mother cell that is competent to divide and form a pair of guard cells appears to be regulated by HvEPF1. In *Arabidopsis* this cellular transition step is under the control of the transcription factor MUTE (FIG. 12) whose activity promotes EPF1-mediated activation of MAP kinases and subsequent downregulation of the activity of transcription factor SPCH via phosphorylation. However, barley MUTE may be more directly regulated by HvEPF1 as grass MUTE genes (unlike *Arabidopsis* MUTE) encode potential MAP kinase phosphorylation sites themselves (Liu et al., 2009).

Despite their importance, we know remarkably little about the sequence of events leading to the production of the air-filled spaces that underlie stomata. In conjunction with the stomatal pores, these substomatal cavities facilitate high levels of gas exchange into plant photosynthetic mesophyll cells, and mediate leaf water loss via transpiration. Using confocal microscopy, we could see no evidence for the separation of mesophyll cells below arrested stomatal precursor cells in HvEPF1OE leaves. Our observations begin to throw light on the developmental sequence leading to cavity formation. The arrested stomatal precursor cells in HvEPF1OE do not form substomatal cavities, suggesting that these cavities form following either GMC maturation, like the subsidiary cells of the stomatal complex, or after guard cell pair formation.

There is much evidence to support a negative correlation between stomatal density and stomatal size across a range of species and *Arabidopsis* stomatal mutants i.e. those plants with relatively low SD tend to produce larger stomates (Miskin & Rasmusson, 1970; Franks & Beerling, 2009; Doheny-Adams et al., 2012). Interestingly, the overexpression of HvEPF1 did not conform to this trend, and led to barley plants with smaller, shorter guard cells. Thus if the EPF signaling pathway directly regulates stomatal size in dicot species (and this remains to be demonstrated), it appears to act in the opposite manner in grass stomatal size determination.

Through the ectopic over-expression of HvEPF1 we have created barley transformants with a range of reductions in SD. Although barley plants with substantially reduced numbers of stomata showed some attenuation of photosynthetic rates when well-watered, they exhibited strong drought avoidance and drought tolerance traits when water was withheld. They had lower levels of water loss via transpiration, and they were able to maintain higher levels of soil water content, and delayed the onset of photosynthetic stress responses for several days longer than controls. Remarkably when grown under water-limiting conditions (25% soil pot water content) two barley lines with reductions in SD demonstrated significant improvements in WUE without any deleterious effects on either plant growth or seed yield (biomass, seed weight or seed number). Under water-limiting conditions HvEPF1OE plants generated, on average, over 50% higher seed yield which, although not significantly increased in our experiments, warrants further investigation. Indeed, it would be interesting to determine whether both WUE and yield may be further optimized in reduced stomatal density lines under less severe watering regimes or through less drastic reductions in SD.

HvEPF1OE-2 plants (which had the lowest SD in this experiment) also displayed significantly enhanced levels of drought tolerance and WUE under well-watered conditions, without accompanying decreases in either grain yield or plant biomass. The increased iWUE observed in these experiments was a result of a relatively moderate drop in A compared to a larger decrease in gs, suggesting that A reached saturation under the growth conditions of our experiment (Yoo et al., 2009). Without wishing to be bound by any particular theory, saturating A under growth conditions may also be a factor in explaining why reductions in SD did not impact on the yield of HvEPF1OE plants. Further explanations include significantly reduced rates of gs and thus water loss in HvEPF1OE plants allowing for more resources to be allocated to the generation of seed and above ground biomass, at the potential cost to root development, or increased soil water content leading to improved nutrient uptake and gs under water limitation. Thus, although not tested in this study, reducing SD may also enhance resource allocation or nutrient uptake capacity under water-restriction.

To conclude, this study describes the function and physiological effect of overexpressing a native epidermal patterning factor in a grass species. The manipulation of HvEPF1 expression levels has improved our understanding of stomatal developmental mechanisms in grasses, and has generated a range of barley plants displaying significantly reduced SD. These barley plants exhibit substantially improved drought tolerance and WUE without reductions in grain yield. This novel discovery adds strength to the proposition that stomatal development represents an attractive target for breeders when attempting to future-proof crops.

Example 10: Improved Resistance to Microbial Pathogen Infection in *Arabidopsis*

Figure 10:
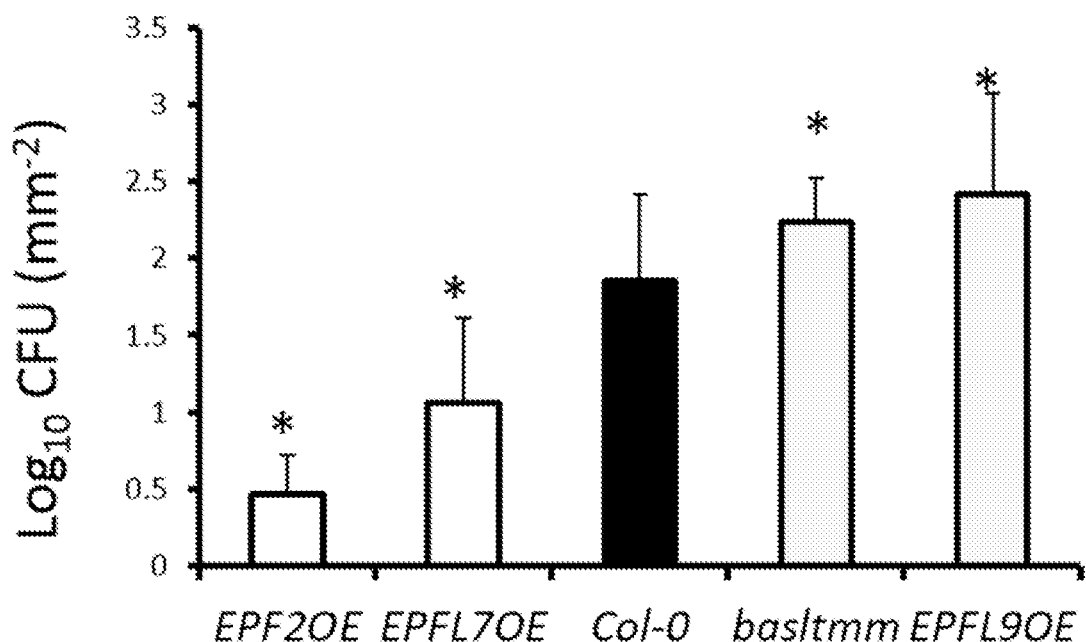
FIG. 10 shows *Arabidopsis* manipulated to have reduced stomatal density have enhanced pathogen resistance. Panel A: Infection levels of reduced, or increased, stomatal density *Arabidopsis* plants following spray inoculation with *Pseudomonas syringae* (PstDC3000); growth measured 24 hr post-inoculation; * $p<0.05$. Panel B.
Figure 10:
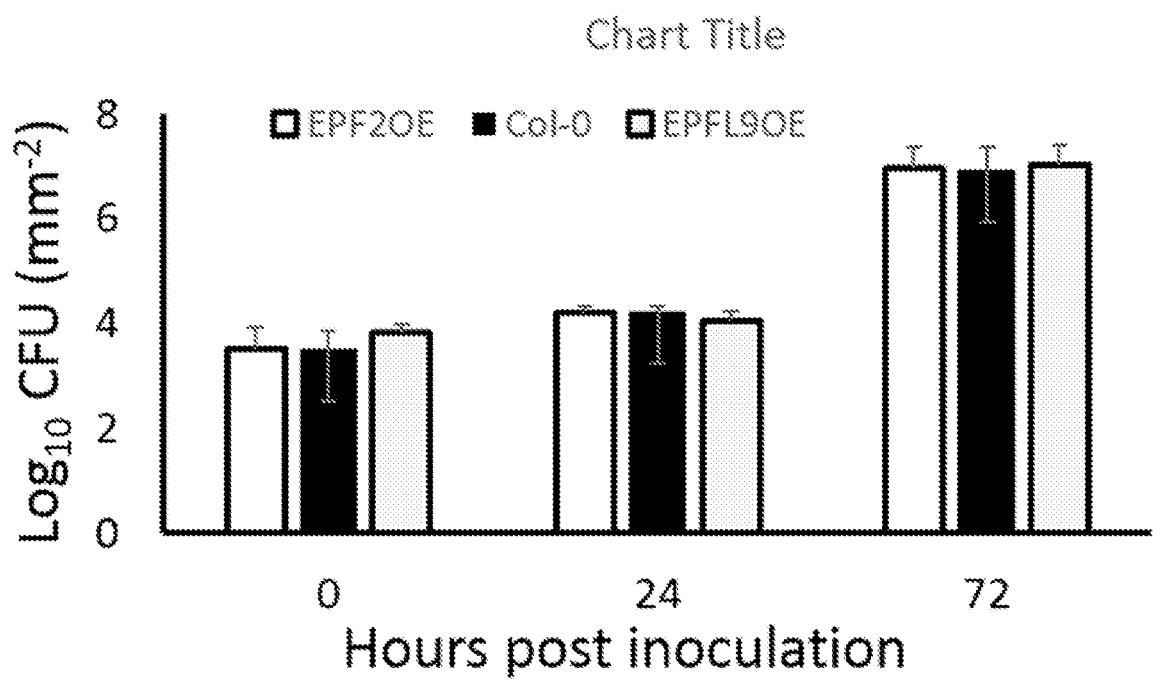

Plants were generated and cultivated as previously (see Examples 2 and 3). *Arabidopsis* plants over-expressing EPF, manipulated to have reduced stomatal density have enhanced pathogen resistance (FIG. 10). Infection levels of reduced, or increased, stomatal density *Arabidopsis* plants following spray inoculation with *Pseudomonas syringae* pv tomato DC3000 (PstDC3000) obtained from Prof Jurriaan Ton, Animal & Plant Sciences Department, University of Sheffield, Sheffield S10 2TN); growth measured 24 hr post-inoculation; *p<0.05 are shown in FIG. 10 (Left Panel). *Arabidopsis* plants with altered stomatal density do not have altered resistance to infection when syringe infiltrated to overcome any stomatal limitation (Right Panel).

Example 11: Over-Expression of a an EPF2 Homologue Reduces Stomatal Density in Rice Plants IR64 rice variety (*Oryza sativa* subsp. indica cv.) was obtained from the International Rice Research Institute, Los Banos, Philippines, in 2015. An over-expression gene construct was made by cloning the rice EPF2 homologue referred to here as OsEPF2 (LOC_Os04g54490.1) cDNA generated by PCR using F—CACCATGAGGAGGCACGCTACTC (SEQ ID NO. 27)
R—CTAGCTGGAGGGCACAGGGTA (SEQ ID NO. 28)

oligonucleotide primers into the pENTR/D-TOPO vector (Thermo Fisher, Waltham, Mass., USA), and an LR clonase reaction (Thermo Fisher, Waltham, Mass., USA) performed to transfer OsEPF2 into the pSC310 vector used for rice transformations using a protocol described by Yin et al. *Plant Cell Reports* 36(5):745-757, 2017. Rice plants were transformed and grown as described in Yin et al. *Plant Cell Reports* 36(5):745-757, 2017. Two transgenic OsEPF2 over-expression rice lines were created, and stomatal density, and transcript levels analysed.

Stomatal density of first leaf abaxial surfaces was measured and is significantly reduced in rice transformed with the OsEPF2 overexpression construct (FIG. 11A). Letters indicate OsEPF2 over-expression lines are statistically significant from control IR64 in first leaf. Stomatal density is significantly reduced in the overexpression lines.

Over-expression of the OsEPF2 gene was further observed at 8 days old in two transgenic lines as measured by qPCR (FIG. 11B).

Example 12: Improved Resistance to Microbial Pathogen Infection in Barley

Barley HvEPF1 plants were generated and cultivated as previously (see examples 2 and 3). The modified plants were screened for resistance to the fungal pathogen brown rust (*Puccinia hordei* strain BBR 06/32, seedling virulence: BBV 1,2,3,4,5,6,8,9,10 obtained from Amelia Hubbard, Huntingdon Road, Cambridge, CB3 0LE, 2017). 3 week old seedlings were painted with spores mixed with talc on the underside of leaves 2 and 3, placed at 100% humidity for 12 hrs at 15° C. then returned to growth chamber and number of pustules counted 7 days later. Numbers shown are the total of pustules summed from both leaves (FIG. 12) showing that modified barley plants with reduced stomatal density have an advantageous increase in resistance to fungal rust infection.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise. Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The reader's attention is directed to all papers and documents which are filed concurrently with or previous to this specification in connection with this application and which are open to public inspection with this specification, and the contents of all such papers and documents are incorporated herein by reference.

NUCLEOTIDE SEQUENCES

[SEQ ID NO: 1]
GSX$^1$X$^2$PDC

[SEQ ID NO: 2]
YRCMC

[SEQ ID NO: 3]
HACGAC

[SEQ ID NO: 4]
CPMVYRCMCKGKCYPVPS

[SEQ ID NO: 5]
PCNRVMVSFKC

[SEQ ID NO: 6]
TGSSLPDCTHACGACKPCNRVMVSFKCSIAEPCPMVYRCMCKGKCYPVPSS

[SEQ ID NO: 7]
EKKDGSGFLQEEVYGTGSSLPDCTHACGACKPCNRVMVSFKCSIAEPCPMVYRCMCKGKCYPVPSS

-continued

HvEPf1 Full-length amino acid
[SEQ ID NO: 8]
MKRHGLAARVHHVRPLLVLLAAVLLLAATVDGIRPDPDDHARPGQAPGAPAVEEKK

DGSG

FLQEEVYGTGSSLPDCTHACGACKPCNRVMVSFKCSIAEPCPMVYRCMCKGKCY

PVPSS

HvEPF1 mRNA sequence
[SEQ ID NO: 9]
CCCUCCAAAGCAGGCUGCUCUUGAGUGAGUGUCACCGUGCACUGUCUGUGC

ACCAGGUCA

AGCUCUUGGAACGCACGCACGCGGGGAUUCUUGGGAUGAUGAUGAAGAGGC

ACGGUCUUGCCGCCCGAGUUCACCACGUUCGCCCCCUUCUUGUCCUCCUCG

CGGCCGUCUUGCUGCUCGCCGCCACGGUCGAUGGCAUCAGACCAGAUCCCG

GUAAGUUCAGCCACAUGAAUGAUCUCUAUGUGCAAUGCCAUCUCCUUCGCAC

GAGAAUCUGACGCUAACUUCCAUCUCCUCCUGGCAGAUGACCAUGCACGCCC

GGGGCAGGCGCCAGGUGCACCGGCGGUGGAGGAGAAGAAGGAUGGGUCGG

GGUUCCUGCAGGAGGAGGUGUACGGGACGGGGUCGAGCCUGCCGGACUGC

ACGCACGCGUGCGGCGCCUGCAAGCCGUGCAACCGCGUGAUGGUCAGCUUC

AAGUGCUCCAUCGCCGAGCCCUGCCCCAUGGUCUACCGCUGCAUGUGCAAG

GGCAAGUGCUACCCCGUCCCCUCCAGCUAG

CUCAGCUCAGACGAUCUCCCCCGCGCACGUACGCACACGGCGGAUGCAAAU

CGAUGCAGAGGGAGCAGACAGCAGAGUAAUAUAUGUGCCGAUCUAGUUGUAU

GUGAUUUU UUAUGCUGGU

HvEPF1 cDNA active region
[SEQ ID NO: 10]
GGGTCGAGCCTGCCGGACTGCACGCACGCGTGC

GGCGCCTGCAAGCCGTGCAACCGCGTGATGGTCAGCTTCAAGTGCTCCATCGC

CGAGCCC

TGCCCCATGGTCTACCGCTGCATGTGCAAGGGCAAGTGCTACCCCGTCCCCTC

CAGCTAG

HvEPF1 cDNA Full-length
[SEQ ID NO: 11]
ATGAAGAGGCACGGTCTTGCCGCCCGAGTTCACCACGTTCGCCCCCTTCTTGT

CCTCCTC

GCGGCCGTCTTGCTGCTCGCCGCCACGGTCGATGGCATCAGACCAGATCCCG

ATGACCAT

GCACGCCCGGGGCAGGCGCCAGGTGCACCGGCGGTGGAGGAGAAGAAGGAT

GGGTCGGGG

TTCCTGCAGGAGGAGGTGTACGGGACG

GGGTCGAGCCTGCCGGACTGCACGCACGCGTGC

GGCGCCTGCAAGCCGTGCAACCGCGTGATGGTCAGCTTCAAGTGCTCCATCGC

CGAGCCC

TGCCCCATGGTCTACCGCTGCATGTGCAAGGGCAAGTGCTACCCCGTCCCCTC

CAGCTAG

HvEPF1 cDNA Full-length with 5'UTR and 3'UTR
[SEQ ID NO: 12]
CCCTCCAAAGCAGGCTGCTCTTGAGTGAGTGTCACCGTGCACTGTCTGTGCAC

CAGGTCA

AGCTCTTGGAACGCACGCACGCGGGGATTCTTGGGATGATGAAGAGGCACGG

TCTTGCCGCCCGAGTTCACCACGTTCGCCCCCTTCTTGTCCTCCTC

GCGGCCGTCTTGCTGCTCGCCGCCACGGTCGATGGCATCAGACCAGATCCCG

ATGACCAT

GCACGCCCGGGGCAGGCGCCAGGTGCACCGGCGGTGGAGGAGAAGAAGGAT

GGGTCGGGG

TTCCTGCAGGAGGAGGTGTACGGGACG

GGGTCGAGCCTGCCGGACTGCACGCACGCGTGC

GGCGCCTGCAAGCCGTGCAACCGCGTGATGGTCAGCTTCAAGTGCTCCATCGC

CGAGCCC

TGCCCCATGGTCTACCGCTGCATGTGCAAGGGCAAGTGCTACCCCGTCCCCTC

CAGCTAG

HvEPF1 gDNA active region (no introns)
[SEQ ID NO: 13]
GGGTCGAGCCTGCCGGACTGCACGCACGCGTGC

GGCGCCTGCAAGCCGTGCAACCGCGTGATGGTCAGCTTCAAGTGCTCCATCGC

CGAGCCC

TGCCCCATGGTCTACCGCTGCATGTGCAAGGGCAAGTGCTACCCCGTCCCCTC

CAGCTAG

HvEPF1 gDNA Full-length
[SEQ ID NO: 14]
ATGATGAAGAGGCACGGTCTTGCCGCCCGAGTTCACCACGTTCGCCCCCTTCT

TGTCCTCCTCGCGGCCGTCTTGCTGCTCGCCGCCACGGTCGATGGCATCAGAC

CAGATCCCGGTAAGTTCAGCCACATGAATGATCTCTATGTGCAATGCCATCTCC

TTCGCACGAGAATCTGACGCTAACTTCCATCTCCTCCTGGCAGATGACCATGCA

CGCCCGGGGCAGGCGCCAGGTGCACCGGCGGTGGAGGAGAAGAAGGATGGG

TCGGGGTTCCTGCAGGAGGAGGTGTACGGGACGGGGTCGAGCCTGCCGGACT

GCACGCACGCGTGCGGCGCCTGCAAGCCGTGCAACCGCGTGATGGTCAGCTT

CAAGTGCTCCATCGCCGAGCCCTGCCCCATGGTCTACCGCTGCATGTGCAAGG

GCAAGTGCTACCCCGTCCCCTCCAGCTAG

HvEPF1 gDNA Full-length with 5'UTR and 3'UTR
[SEQ ID NO: 15]
CCCTCCAAAGCAGGCTGCTCTTGAGTGAGTGTCACCGTGCACTGTCTGTGCAC

CAGGTCA

AGCTCTTGGAACGCACGCACGCGGGGATTCTTGGGATGATGATGAAGAGGCAC

GGTCTTGCCGCCCGAGTTCACCACGTTCGCCCCCTTCTTGTCCTCCTCGCGGC

CGTCTTGCTGCTCGCCGCCACGGTCGATGGCATCAGACCAGATCCCGGTAAGT

TCAGCCACATGAATGATCTCTATGTGCAATGCCATCTCCTTCGCACGAGAATCT

GACGCTAACTTCCATCTCCTCCTGGCAGATGACCATGCACGCCCGGGGCAGGC

GCCAGGTGCACCGGCGGTGGAGGAGAAGAAGGATGGGTCGGGGTTCCTGCA

GGAGGAGGTGTACGGGACGGGGTCGAGCCTGCCGGACTGCACGCACGCGTG

-continued

CGGCGCCTGCAAGCCGTGCAACCGCGTGATGGTCAGCTTCAAGTGCTCCATCG

CCGAGCCCTGCCCCATGGTCTACCGCTGCATGTGCAAGGGCAAGTGCTACCCC

GTCCCCTCCAGCTAG

CTCAGCTCAGACGATCTCCCCCGCGCACGTACGCACACGGCGGATGCAAAT

CGATGCAGAGGGAGCAGACAGCAGAGTAATATATGTGCCGATCTAGTTGTATG

TGATTTT TTATGCTGGT

HvEPF1 gDNA Full-length in vector

[SEQ ID NO: 16]
TTTTTATCCCCGGAAGCCTGTGGATAGAGGGTAGTTATCCACGTGAAACCGCTAATGCCC

CGCAAAGCCTTGATTCACGGGGCTTTCCGGCCCGCTCCAAAAACTATCCACGTGAAATCG

CTAATCAGGGTACGTGAAATCGCTAATCGGAGTACGTGAAATCGCTAATAAGGTCACGTG

AAATCGCTAATCAAAAAGGCACGTGAGAACGCTAATAGCCCTTTCAGATCAACAGCTTGC

AAACACCCCTCGCTCCGGCAAGTAGTTACAGCAAGTAGTATGTTCAATTAGCTTTTCAAT

TATGAATATATATATCAATTATTGGTCGCCCTTGGCTTGTGGACAATGCGCTACGCGCAC

CGGCTCCGCCCGTGGACAACCGCAAGCGGTTGCCCACCGTCGAGCGCCAGCGCCTTTGCC

CACAACCCGGCGGCCGGCCGCAACAGATCGTTTTATAAATTTTTTTTTTGAAAAAGAAA
    LB
    ~

AAGCCCGAAAGGCGGCAACCTCTCGGGCTTCTGGATTTCCGATCCCCGGAATTAGATCTT
    LB
    ~~~~~~~~~~~~~~~~~~~~~~~~

GGCAGGATATATTGTGGTGTAACGTATCACAAGTTTGTACAAAAAAGCAGGCTCCGCGGC

CGCCCCCTTCACCTAGACTCGACGCGTCCTAGAGATCCGTCAACATGGTGGAGCACGACA

CTCTCGTCTACTCCAAGAATATCAAAGATACAGTCTCAGAAGACCAAAGGGCTATTGAGA

CTTTTCAACAAAGGGTAATATCGGGAAACCTCCTCGGATTCCATTGCCCAGCTATCTGTC

ACTTCATCAAAAGGACAGTAGAAAAGGAAGGTGGCACCTACAAATGCCATCATTGCGATA

AAGGAAAGGCTATCGTTCAAGATGCCTCTGCCGACAGTGGTCCCAAAGATGGACCCCCAC

CCACGAGGAGCATCGTGGAAAAAGAAGACGTTCCAACCACGTCTTCAAAGCAAGTGGATT

GATGTGATATCTCCACTGACGTAAGGGATGACGCACAATCCCACTATCCTTCGCAAGACC

CTTCCTCTATATAAGGAAGTTCATTTCATTTGGAGAGGACGACCCCGATATGAAAAAGCC

TGAACTCACCGCGACGTCTGTCGAGAAGTTTCTGATCGAAAAGTTCGACAGCGTCTCCGA

CCTGATGCAGCTCTCGGAGGGCGAAGAATCTCGTGCTTTCAGCTTCGATGTAGGAGGGCG

TGGATATGTCCTGCGGGTAAATAGCTGCGCCGATGGTTTCTACAAAGATCGTTATGTTTA

TCGGCACTTTGCATCGGCCGCGCTCCCGATTCCGGAAGTGCTTGACATTGGGGAATTCAG

CGAGAGCCTGACCTATTGCATCTCCCGCCGTGCACAGGGTGTCACGTTGCAAGACCTGCC

TGAAACCGAACTGCCCGCTGTTCTGCAGGTAAATTTCTAGTTTTTCTCCTTCATTTTCTT

GGTTAGGACCCTTTTCTCTTTTTATTTTTTGAGCTTTGATCTTTCTTTAAACTGATCTA

TTTTTTAATTGATTGGTTATGGTGTAAATATTACATAGCTTTAACTGATAATCTGATTAC

TTTATTTCGTGTGTCTATGATGATGATGATAACTGCAGCCGGTCGCGGAGGCCATGGATG

CGATCGCTGCGGCCGATCTTAGCCAGACGAGCGGGTTCGGCCCATTCGGACCGCAAGGAA

TCGGTCAATACACTACATGGCGTGATTTCATATGCGCGATTGCTGATCCCCATGTGTATC

ACTGGCAAACTGTGATGGACGACACCGTCAGTGCGTCCGTCGCGCAGGCTCTCGATGAGC

TGATGCTTTGGGCCGAGGACTGCCCCGAAGTCCGGCACCTCGTGCACGCGGATTTCGGCT

-continued

```
CCAACAATGTCCTGACGGACAATGGCCGCATAACAGCGGTCATTGACTGGAGCGAGGCGA

TGTTCGGGGATTCCCAATACGAGGTCGCCAACATCTTCTTCTGGAGGCCGTGGTTGGCTT

GTATGGAGCAGCAGACGCGCTACTTCGAGCGGAGGCATCCGGAGCTTGCAGGATCGCCGC

GGCTCCGGGCGTATATGCTCCGCATTGGTCTTGACCAACTCTATCAGAGCTTGGTTGACG

GCAATTTCGATGATGCAGCTTGGGCGCAGGGTCGATGCGACGCAATCGTCCGATCCGGAG

CCGGGACTGTCGGGCGTACACAAATCGCCCGCAGAAGCGCGGCCGTCTGGACCGATGGCT

GTGTAGAAGTACTCGCCGATAGTGGAAACCGACGCCCCAGCACTCGTCCGAGGGCAAAGG
        SacI
        ~~~~~~~

AATAGAGTAGATGCCGACCGGGATCCGGAGAGCTCGAATTTCCCCGATCGTTCAAACATT

TGGCAATAAAGTTTCTTAAGATTGAATCCTGTTGCCGGTCTTGCGATGATTATCATATAA

TTTCTGTTGAATTACGTTAAGCATGTAATAATTAACATGTAATGCATGACGTTATTTATG

AGATGGGTTTTTATGATTAGAGTCCCGCAATTATACATTTAATACGCGATAGAAAACAAA

ATATAGCGCGCAAACTAGGATAAATTATCGCGCGGTGTCATCTATGTTACTAGATCGG

GAATTCATCGATGATATCAGATCAAGGGTGGGCGCGCCGAACCAGCTTTCTTGTACAAAG
        XhoIHindIII
        ~~~~~~~~~~~~

TGGTGATCCCCCTCGAGGTCGACGGTATCGATAAGCTTGATATCGAATTCCGTGCAGCGT

GACCCGGTCGTGCCCCTCTCTAGAGATAATGAGCATTGCATGTCTAAGTTATAAAAAATT

ACCACATATTTTTTTTGTCACACTTGTTTGAAGTGCAGTTTATCTATCTTTATACATATA

TTTAAACTTTACTCTACGAATAATATAATCTATAGTACTACAATAATATCAGTGTTTTAG

AGAATCATATAAATGAACAGTTAGACATGGTCTAAAGGACAATTGAGTATTTTGACAACA

GGACTCTACAGTTTTATCTTTTTAGTGTGCATGTGTTCTCCTTTTTTTTGCAAATAGCT

TCACCTATATAATACTTCATCCATTTTATTAGTACATCCATTTAGGGTTTAGGGTTAATG

GTTTTTATAGACTAATTTTTTTAGTACATCTATTTTATTCTATTTTAGCCTCTAAATTAA

GAAAACTAAAACTCTATTTTAGTTTTTTTATTTAATAATTTAGATATAAAATAGAATAAA

ATAAAGTGACTAAAAATTAAACAAATACCCTTTAAGAAATTAAAAAAACTAAGGAAACAT

TTTTCTTGTTTCGAGTAGATAATGCCAGCCTGTTAAACGCCGTCGACGAGTCTAACGGAC

ACCAACCAGCGAACCAGCAGCGTCGCGTCGGGCCAAGCGAAGCAGACGGCACGGCATCTC
        XhoI
        ~~~~~~

TGTCGCTGCCTCTGGACCCCTCTCGAGAGTTCCGCTCCACCGTTGGACTTGCTCCGCTGT

CGGCATCCAGAAATTGCGTGTCGGACGGCAGACGTGAGCCGGCACGGCAGGCGGCCTCCT

CCTCCTCTCACGGCACCGGCAGCTACGGGGGATTCCTTTCCCACCGCTCCTTCGCTTTCC

CTTCCTCGCCCGCCGTAATAAATAGACACCCCCTCCACACCCTCTTTCCCCAACCTCGTG

TTGTTCGGAGCGCACACACACACAACCAGATCTCCCCCAAATCCACCCGTCGGCACCTCC

GCTTCAAGGTACGCCGCTCGTCCTCCCCCCCCCCCCCCTCTCTACCTTCTCTAGATCGGCG
        ApaI
        ~~~~~~~

TTCCGGTCCATGGTTAGGGCCCGGTAGTTCTACTTCTGTTCATGTTTGTGTTAGATCCGT

GTTTGTGTTAGATCCGTGCTGCTAGCGTTCGTACACGGATGCGACCTGTACGTCAGACAC

GTTCTGATTGCTAACTTGCCAGTGTTTCTCTTTGGGGAATCCTGGGATGGCTCTAGCCGT

TCCGCAGACGGGATCGATTTCATGATTTTTTTTGTTTCGTTGCATAGGGTTTGGTTTGC

CCTTTTCCTTTATTTCAATATATGCCGTGCACTTGTTTGTCGGGTCATCTTTTCATGCTT

TTTTTTGTCTTGGTTGTGATGATGTGGTCTGGTTGGGCGGTCGTTCTAGATCGGAGTAGA
```

```
ATTAATTCTGTTTCAAACTACCTGGTGGATTTATTAATTTTGGATCTGTATGTGTGTGCC

ATACATATTCATAGTTACGAATTGAAGATGATGGATGGAAATATCGATCTAGGATAGGTA

TACATGTTGATGCGGGTTTTACTGATGCATATACAGAGATGCTTTTTGTTCGCTTGGTTG

TGATGATGTGGTGTGGTTGGGCGGTCGTTCATTCGTTCTAGATCGGAGTAGAATACTGTT

TCAAACTACCTGGTGTATTTATTAATTTTGGAACTGTATGTGTGTGTCATACATCTTCAT

AGTTACGAGTTTAAGATGGATGGAAATATCGATCTAGGATAGGTATACATGTTGATGTGG

GTTTTACTGATGCATATACATGATGGCATATGCAGCATCTATTCATATGCTCTAACCTTG

AGTACCTATCTATTATAATAAACAAGTATGTTTTATAATTATTTTGATCTTGATATACTT
     pAHUbi_promDprimerforward
     ~~~~~~~~~~~~~~~~~~~~~~~
GGATGATGGCATATGCAGCAGCTATATGTGGATTTTTTTAGCCCTGCCTTCATACGCTAT

TTATTTGCTTGGTACTGTTTCTTTTGTCGATGCTCACCCTGTTGTTTGGTGTTACTTCGC

CCATCACAAGTTTGTACAAAAAAGCTGAACGAGAAACGTAAAATGATATAAATATCAATA

CACCATGAAGAGGCACGGTCTTGCCGCCCGAGTTCACCACGTTCGCCCCCTTCTTGTCCTCCTC

GCGGCCGTCTTGCTGCTCGCCGCCACGGTCGATGGCATCAGACCAGATCCCGATGACCAT

GCACGCCCGGGGCAGGCGCCAGGTGCACCGGCGGTGGAGGAGAAGAAGGATGGGTCGGGG

TTCCTGCAGGAGGAGGTGTACGGGACGGGGTCGAGCCTGCCGGACTGCACGCACGCGTGC

GGCGCCTGCAAGCCGTGCAACCGCGTGATGGTCAGCTTCAAGTGCTCCATCGCCGAGCCC

TGCCCCATGGTCTACCGCTGCATGTGCAAGGGCAAGTGCTACCCCGTCCCCTCCAGCTAG

GCGCGCCGACCCAGCTTTCTTGTACAAAGTGGTGATGGGGGATCCACTAGTTCTAGAATTCGA

TTGAGTCAAGCAGGATCGTTCAAACATTTGGCAATAAAGTTTCTTAAGATTGAATCCTGT

TGCCGGTCTTGCGATGATTATCATATAATTTCTGTTGAATTACGTTAAGCATGTAATAAT

TAACATGTAATGCATGACGTTATTTATGAGATGGGTTTTTATGATTAGAGTCCCGCAATT

ATACATTTAATACGCGATAGAAAACAAAATATAGCGCGCAAACTAGGATAAATTATCGCG
        nosterm_3'Reverseprimer
        ~~~~~~~~~~~~~~~~~~~~~~~
CGCGGTGTCATCTATGTTACTAGATCGACCGGCATGCAAGCTGATATCAATCACTAGTGA
        SacI
        ~~~~~~~
ATTCTAGAGCGGCCGCCACCGCGGTGGAGCTCCAGCTTTTGTTCCCTTTAGTGAGGGTTA

ATTGCGCGCTTGGCGTAATCATGGTCATAGCTGTTTCCTGTGTGAAATTGTTATCCGCTC

ACAATTCCACACAACATACGAGCCGGAAGCATAAAGTGTAAAGCCTGGGGTGCCTAATGA

GTGAGCTAACTCACATTAATTGCGTTGCGCTCACTGCCCGCTTTCCAGTCGGGAAACCTG

TCGTGCCAGCTGCATTAATGAATCGGCCAACGCGCGGGGAGAGGCGGTTTGCGTATTGGG

CGCTCTTCCGCTTCCTCGCTCACTGACTCGCTGCGCTCGGTCGTTCGGCTGCGGCGAGCG

GTATCAGCTCACTCAAAGGCGGTAATACGGTTATCCACAGAATCAGGGGATAACGCAGGA
        RB
        ~~~~~~~~~~~~~~~~~~~~~~~~~~~
        StuI
        ~~~~~~
AAGAACATGAAGGCCTTGACAGGATATATTGGCGGGTAAACTAAGTCGCTGTATGTGTTT

GTTTGAGATCTCATGTGAGCAAAAGGCCAGCAAAAGGCCAGGAACCGTAAAAAGGCCGCG

TTGCTGGCGTTTTTCCATAGGCTCCGCCCCCCTGACGAGCATCACAAAAATCGACGCTCA

AGTCAGAGGTGGCGAAACCCGACAGGACTATAAAGATACCAGGCGTTTCCCCCTGGAAGC

TCCCTCGTGCGCTCTCCTGTTCCGACCCTGCCGCTTACCGGATACCTGTCCGCCTTTCTC
```

-continued

```
CCTTCGGGAAGCGTGGCGCTTTCTCATAGCTCACGCTGTAGGTATCTCAGTTCGGTGTAG

GTCGTTCGCTCCAAGCTGGGCTGTGTGCACGAACCCCCCGTTCAGCCCGACCGCTGCGCC

TTATCCGGTAACTATCGTCTTGAGTCCAACCCGGTAAGACACGACTTATCGCCACTGGCA

GCAGCCACTGGTAACAGGATTAGCAGAGCGAGGTATGTAGGCGGTGCTACAGAGTTCTTG

AAGTGGTGGCCTAACTACGGCTACACTAGAAGAACAGTATTTGGTATCTGCGCTCTGCTG

AAGCCAGTTACCTTCGGAAGAAGAGTTGGTAGCTCTTGATCCGGCAAACAAACCACCGCT

GGTAGCGGTGGTTTTTTGTTTGCAAGCAGCAGATTACGCGCAGAAAAAAGGATCTCAA

GAAGATCCTTTGATCTTTTCTACGGGGTCTGACGCTCAGTGGAACGAAAACTCACGTTAA

GGGATTTTGGTCATGAGATTATCAAAAGGATCTTCACCTAGATCCTTTTAAATTAAAAA

TGAAGTTTTAAATCAATCTAAAGTATATATGTGTAACATTGGTCTAGTGATTAGAAAAAC

TCATCGAGCATCAAATGAAACTGCAATTTATTCATATCAGGATTATCAATACCATATTTT

TGAAAAAGCCGTTTCTGTAATGAAGGAGAAAACTCACCGAGGCAGTTCCATAGGATGGCA

AGATCCTGGTATCGGTCTGCGATTCCGACTCGTCCAACATCAATACAACCTATTAATTTC

CCCTCGTCAAAAATAAGGTTATCAAGTGAGAAATCACCATGAGTGACGACTGAATCCGGT

GAGAATGGCAAAAGTTTATGCATTTCTTTCCAGACTTGTTCAACAGGCCAGCCATTACGC

TCGTCATCAAAATCACTCGCATCAACCAAACCGTTATTCATTCGTGATTGCGCCTGAGCG

AGACGAAATACGCGATCGCTGTTAAAAGGACAATTACAAACAGGAATCGAATGCAACCGG

CGCAGGAACACTGCCAGCGCATCAACAATATTTTCACCTGAATCAGGATATTCTTCTAAT

ACCTGGAATGCTGTTTTCCCTGGGATCGCAGTGGTGAGTAACCATGCATCATCAGGAGTA

CGGATAAAATGCTTGATGGTCGGAAGAGGCATAAATTCCGTCAGCCAGTTTAGTCTGACC

ATCTCATCTGTAACAACATTGGCAACGCTACCTTTGCCATGTTTCAGAAACAACTCTGGC

GCATCGGGCTTCCCATACAATCGGTAGATTGTCGCACCTGATTGCCCGACATTATCGCGA

GCCCATTTATACCCATATAAATCAGCATCCATGTTGGAATTTAATCGCGGCCTTGAGCAA

GACGTTTCCCGTTGAATATGGCTCATAACACCCCTTGTATTACTGTTTATGTAAGCAGAC

AGTTTTATTGTTCATGATGATATATTTTTATCTTGTGCAATGTAACATCAGAGATTTTGA

GACACAACGTGGCTTTGTTGAATAAATCGAACTTTTGCTGAGTTGAAGGATCAGATCACG

CATCTTCCCGACAACGCAGACCGTTCCGTGGCAAAGCAAAAGTTCAAAATCACCAACTGG

TCCACCTACAACAAAGCTCTCATCAACCGTGGCTCCCTCACTTTCTGGCTGGATGATGGG

GCGATTCAGGCGATCCCCATCCAACAGCCCGCCGTCGAGCGGGCT
```

Hygromycin Forward Primer
[SEQ ID NO: 17]
ACTCACCGCGACGTCTG

Hygromycin Reverse Primer
[SEQ ID NO: 18]
GCGCGTCTGCTGCTCCATA

HvGAPDH Forward Primer
[SEQ ID NO: 19]
GTGAGGCTGGTGCTGATT

HvGAPDH Reverse Primer
[SEQ ID NO: 20]
CGTGGTGCAGCTAGCATTTGAGAC

HvTubulin Forward Primer
[SEQ ID NO: 21]
AGTGTCCTGTCCACCCACTC

HvTubulin Reverse Primer
[SEQ ID NO: 22]
AGCATGAAGTGGATCCTTGG

```
HvEPF1 Forward Primer (qPCR)
                                                         [SEQ ID NO: 23]
GTGGAGGAGAAGAAGGATGG HvEPF1 Reverse Primer (qPCR)
                                                         [SEQ ID NO: 24]
ATGGAGCACTTGAAGCTGAC HvEPF1 Forward Primer (vector construction)
                                                         [SEQ ID NO: 25]
CACCATGAAGAGGCACGGTCTT HvEPF1 Reverse Primer (vector construction)
                                                         [SEQ ID NO: 26]
CTAGCTGGAGGGGACGGGGT OsEPF2 Forward Primer
                                                         [SEQ ID NO: 27]
CACCATGAGGAGGCACGCTACTC OsEPF2 Reverse Primer
                                                         [SEQ ID NO: 28]
CTAGCTGGAGGGCACAGGGTA
```

---

The invention claimed is:

1. A method of modifying stomatal density in a monocot plant, comprising contacting the monocot plant with a genome editing system specific to a genome sequence encoding a polypeptide comprising the amino acid motif GSX$^1$X$^2$PDC [SEQ ID NO: 1], wherein X$^1$ is one of S or R and X$^2$ is one of L or I, thereby genetically modifying the monocot plant to reduce the presence, expression or activity in cells of the monocot plant of the polypeptide comprising the amino acid motif GSX$^1$X$^2$PDC [SEQ ID NO: 1], wherein X$^1$ is one of S or R and X$^2$ is one of L or I compared to the presence, expression or activity of the polypeptide in cells of an equivalent control plant not contacted with the genome editing system.

2. The method as claimed in claim 1, wherein the polypeptide further comprises at least one of:
   the amino acid motif YRCMC [SEQ ID NO: 2];
   the amino acid motif HACGAC [SEQ ID NO: 3];
   the amino acid motif CPMVYRCMCKGKCYPVPS [SEQ ID NO: 4];
   the amino acid motif PCNRVMVSFKC [SEQ ID NO: 5];
   the amino acid sequence motif TGSSLPDCTHACGACKPCNRVMVSFKCSIAEPCPMVYRCMCKGKCYPVPSS [SEQ ID NO: 6]; and
   the amino acid sequence motif EKKDGSGFLQEEVYGTGSSLPDCTHACGACKPCNRVMVSFKCSIAEPCPMVYRCMCKG KCYPVPSS [SEQ ID NO: 7].

3. The method as claimed in claim 1, wherein the polypeptide comprises the sequence of SEQ ID NO: 8 or a sequence of at least 38% identity thereto.

4. The method as claimed in claim 1, wherein the polypeptide is encoded by a polynucleotide sequence comprising:
   a. SEQ ID NO: 9; or a sequence of at least 67% identity thereto; or
   b. SEQ ID NO: 10; or a sequence of at least 67%; identity thereto; or
   c. SEQ ID NO: 11; or a sequence of at least 59%; identity thereto; or
   d. SEQ ID NO: 13; or a sequence of at least 66% identity thereto; or
   e. SEQ ID NO: 14; or a sequence of at least 58% identity thereto.

5. The method as claimed in claim 1, wherein the polypeptide comprises the sequence of SEQ ID NO: 8 or a sequence of at least 60% identity thereto.

* * * * *

```
                            SEQUENCE LISTING

<160> NUMBER OF SEQ ID NOS: 61

<210> SEQ ID NO 1
<211> LENGTH: 7
<212> TYPE: PRT
<213> ORGANISM: Hordeum vulgare
<220> FEATURE:
<221> NAME/KEY: MOD_RES
<222> LOCATION: (3)..(3)
<223> OTHER INFORMATION: Ser or Arg
<220> FEATURE:
<221> NAME/KEY: MOD_RES
<222> LOCATION: (4)..(4)
<223> OTHER INFORMATION: Leu or Ile

<400> SEQUENCE: 1

Gly Ser Xaa Xaa Pro Asp Cys
1               5

<210> SEQ ID NO 2
<211> LENGTH: 5
<212> TYPE: PRT
<213> ORGANISM: Hordeum vulgare

<400> SEQUENCE: 2

Tyr Arg Cys Met Cys
1               5

<210> SEQ ID NO 3
<211> LENGTH: 6
<212> TYPE: PRT
<213> ORGANISM: Hordeum vulgare

<400> SEQUENCE: 3

His Ala Cys Gly Ala Cys
1               5

<210> SEQ ID NO 4
<211> LENGTH: 18
<212> TYPE: PRT
<213> ORGANISM: Hordeum vulgare

<400> SEQUENCE: 4
```

```
Cys Pro Met Val Tyr Arg Cys Met Cys Lys Gly Lys Cys Tyr Pro Val
1               5                   10                  15

Pro Ser

<210> SEQ ID NO 5
<211> LENGTH: 11
<212> TYPE: PRT
<213> ORGANISM: Hordeum vulgare

<400> SEQUENCE: 5

Pro Cys Asn Arg Val Met Val Ser Phe Lys Cys
1               5                   10

<210> SEQ ID NO 6
<211> LENGTH: 51
<212> TYPE: PRT
<213> ORGANISM: Hordeum vulgare

<400> SEQUENCE: 6

Thr Gly Ser Ser Leu Pro Asp Cys Thr His Ala Cys Gly Ala Cys Lys
1               5                   10                  15

Pro Cys Asn Arg Val Met Val Ser Phe Lys Cys Ser Ile Ala Glu Pro
            20                  25                  30

Cys Pro Met Val Tyr Arg Cys Met Cys Lys Gly Lys Cys Tyr Pro Val
        35                  40                  45

Pro Ser Ser
        50

<210> SEQ ID NO 7
<211> LENGTH: 66
<212> TYPE: PRT
<213> ORGANISM: Hordeum vulgare

<400> SEQUENCE: 7

Glu Lys Lys Asp Gly Ser Gly Phe Leu Gln Glu Val Tyr Gly Thr
1               5                   10                  15

Gly Ser Ser Leu Pro Asp Cys Thr His Ala Cys Gly Ala Cys Lys Pro
            20                  25                  30

Cys Asn Arg Val Met Val Ser Phe Lys Cys Ser Ile Ala Glu Pro Cys
        35                  40                  45

Pro Met Val Tyr Arg Cys Met Cys Lys Gly Lys Cys Tyr Pro Val Pro
    50                  55                  60

Ser Ser
65

<210> SEQ ID NO 8
<211> LENGTH: 119
<212> TYPE: PRT
<213> ORGANISM: Hordeum vulgare

<400> SEQUENCE: 8

Met Lys Arg His Gly Leu Ala Ala Arg Val His Val Arg Pro Leu
1               5                   10                  15

Leu Val Leu Leu Ala Ala Val Leu Leu Leu Ala Ala Thr Val Asp Gly
            20                  25                  30

Ile Arg Pro Asp Pro Asp Asp His Ala Arg Pro Gly Gln Ala Pro Gly
        35                  40                  45

Ala Pro Ala Val Glu Glu Lys Lys Asp Gly Ser Gly Phe Leu Gln Glu
    50                  55                  60
```

```
Glu Val Tyr Gly Thr Gly Ser Ser Leu Pro Asp Cys Thr His Ala Cys
 65                  70                  75                  80

Gly Ala Cys Lys Pro Cys Asn Arg Val Met Val Ser Phe Lys Cys Ser
                 85                  90                  95

Ile Ala Glu Pro Cys Pro Met Val Tyr Arg Cys Met Cys Lys Gly Lys
            100                 105                 110

Cys Tyr Pro Val Pro Ser Ser
            115
```

<210> SEQ ID NO 9
<211> LENGTH: 670
<212> TYPE: RNA
<213> ORGANISM: Hordeum vulgare

<400> SEQUENCE: 9

```
cccuccaaag caggcugcuc uugagugagu gucaccgugc acugucugug caccaggcuca    60
agcucuugga acgcacgcac gcggggauuc uugggaugau gaugaagagg cacggucuug   120
ccgcccgagu ucaccacguu cgcccccuuc uuguccuccu cgcggccguc uugcugcucg   180
ccgccacggu cgauggcauc agaccagauc ccgguaaguu cagccacaug aaugaucucu   240
augugcaaug ccaucuccuu cgcacagaaa ucugacgcua acuuccaucu ccuccuggca   300
gaugaccaug cacgcccggg gcaggcgcca ggugcaccgg cggugagga gaagaaggau    360
gggucggggu uccugcagga ggaggugauc gggacgggu cgagccugcc ggacugcacg    420
cacgcgugcg gcgccugcaa gccgugcaac cgcgugaugg ucagcuucaa gugcuccauc   480
gccgagcccu gccccauggu cuaccgcugc augugcaagg gcaagugcua ccccgucccc   540
uccagcuagc ucagcucaga cgaucucccc cgcgcacgua cgcacacggc ggaugcaaau   600
cgaugcagag ggagcagaca gcagaguaau auaugugccg aucuaguugu augugauuuu   660
uuaugcuggu                                                          670
```

<210> SEQ ID NO 10
<211> LENGTH: 153
<212> TYPE: DNA
<213> ORGANISM: Hordeum vulgare

<400> SEQUENCE: 10

```
gggtcgagcc tgccggactg cacgcacgcg tgcggcgcct gcaagccgtg caaccgcgtg    60
atggtcagct tcaagtgctc catcgccgag ccctgcccca tggtctaccg ctgcatgtgc   120
aagggcaagt gctaccccgt cccctccagc tag                                153
```

<210> SEQ ID NO 11
<211> LENGTH: 360
<212> TYPE: DNA
<213> ORGANISM: Hordeum vulgare

<400> SEQUENCE: 11

```
atgaagaggc acggtcttgc cgcccgagtt caccacgttc gccccttct tgtcctcctc     60
gcggccgtct tgctgctcgc cgccacggtc gatggcatca gaccagatcc gatgaccat   120
gcacgcccgg ggcaggcgcc aggtgcaccg gcggtggagg agaagaagga tgggtcgggg   180
ttcctgcagg aggaggtgta cgggacgggg tcgagcctgc cggactgcac gcacgcgtgc   240
ggcgcctgca agccgtgcaa ccgcgtgatg gtcagcttca agtgctccat cgccgagccc   300
tgccccatgg tctaccgctg catgtgcaag ggcaagtgct accccgtccc ctccagctag   360
```

```
<210> SEQ ID NO 12
<211> LENGTH: 458
<212> TYPE: DNA
<213> ORGANISM: Hordeum vulgare

<400> SEQUENCE: 12
ccctccaaag caggctgctc ttgagtgagt gtcaccgtgc actgtctgtg caccaggtca      60
agctcttgga acgcacgcac gcggggattc ttgggatgat gaagaggcac ggtcttgccg     120
cccgagttca ccacgttcgc cccttcttg tcctcctcgc ggccgtcttg ctgctcgccg      180
ccacggtcga tggcatcaga ccagatcccg atgaccatgc acgcccgggg caggcgccag     240
gtgcaccggc ggtggaggag aagaaggatg gtcggggtt cctgcaggag gaggtgtacg      300
ggacggggtc gagcctgccg gactgcacgc acgcgtgcgg cgcctgcaag ccgtgcaacc     360
gcgtgatggt cagcttcaag tgctccatcg ccgagccctg ccccatggtc taccgctgca     420
tgtgcaaggg caagtgctac cccgtcccct ccagctag                             458

<210> SEQ ID NO 13
<211> LENGTH: 153
<212> TYPE: DNA
<213> ORGANISM: Hordeum vulgare

<400> SEQUENCE: 13
gggtcgagcc tgccggactg cacgcacgcg tgcggcgcct gcaagccgtg caaccgcgtg      60
atggtcagct tcaagtgctc catcgccgag ccctgcccca tggtctaccg ctgcatgtgc     120
aagggcaagt gctaccccgt cccctccagc tag                                  153

<210> SEQ ID NO 14
<211> LENGTH: 451
<212> TYPE: DNA
<213> ORGANISM: Hordeum vulgare

<400> SEQUENCE: 14
atgatgaaga ggcacggtct tgccgcccga gttcaccacg ttcgcccccct tcttgtcctc     60 ctcgcggccg tcttgctgct cgccgccacg gtcgatggca tcagaccaga tcccggtaag    120
ttcagccaca tgaatgatct ctatgtgcaa tgccatctcc ttcgcacgag aatctgacgc    180
taacttccat ctcctcctgg cagatgacca tgcacgcccg gggcaggcgc aggtgcacc    240 ggcggtggag gagaagaagg atgggtcggg gttcctgcag gaggaggtgt acggacggg    300 gtcgagcctg ccggactgca cgcacgcgtg cggcgcctgc aagccgtgca accgcgtgat    360
ggtcagcttc aagtgctcca tcgccgagcc ctgccccatg gtctaccgct gcatgtgcaa    420
gggcaagtgc taccccgtcc cctccagcta g                                   451

<210> SEQ ID NO 15
<211> LENGTH: 670
<212> TYPE: DNA
<213> ORGANISM: Hordeum vulgare

<400> SEQUENCE: 15
ccctccaaag caggctgctc ttgagtgagt gtcaccgtgc actgtctgtg caccaggtca      60
agctcttgga acgcacgcac gcggggattc ttgggatgat gatgaagagg cacggtcttg    120
ccgcccgagt tcaccacgtt cgccccctttc ttgtcctcct cgcggccgtc ttgctgctcg    180
ccgccacggt cgatggcatc agaccagatc cggtaagtt cagccacatg aatgatctct    240
atgtgcaatg ccatctcctt cgcacgagaa tctgacgcta acttccatct cctcctggca    300
```

| | |
|---|---|
| gatgaccatg cacgcccggg gcaggcgcca ggtgcaccgg cggtggagga gaagaaggat | 360 |
| gggtcggggt tcctgcagga ggaggtgtac gggacggggt cgagcctgcc ggactgcacg | 420 |
| cacgcgtgcg gcgcctgcaa gccgtgcaac cgcgtgatgg tcagcttcaa gtgctccatc | 480 |
| gccgagccct gccccatggt ctaccgctgc atgtgcaagg gcaagtgcta ccccgtcccc | 540 |
| tccagctagc tcagctcaga cgatctcccc cgcgcacgta cgcacacggc ggatgcaaat | 600 |
| cgatgcagag ggagcagaca gcagagtaat atatgtgccg atctagttgt atgtgatttt | 660 |
| ttatgctggt | 670 |

```
<210> SEQ ID NO 16
<211> LENGTH: 7912
<212> TYPE: DNA
<213> ORGANISM: Hordeum vulgare

<400> SEQUENCE: 16
```

| | |
|---|---|
| tttttatccc cggaagcctg tggatagagg gtagttatcc acgtgaaacc gctaatgccc | 60 |
| cgcaaagcct tgattcacgg ggcttttccgg cccgctccaa aaactatcca cgtgaaatcg | 120 |
| ctaatcaggg tacgtgaaat cgctaatcgg agtacgtgaa atcgctaata aggtcacgtg | 180 |
| aaatcgctaa tcaaaaaggc acgtgagaac gctaatagcc ctttcagatc aacagcttgc | 240 |
| aaacacccct cgctccggca agtagttaca gcaagtagta tgttcaatta gcttttcaat | 300 |
| tatgaatata tatatcaatt attggtcgcc cttggcttgt ggacaatgcg ctacgcgcac | 360 |
| cggctccgcc cgtggacaac cgcaagcggt tgcccaccgt cgagcgccag cgcctttgcc | 420 |
| cacaacccgg cggccggccg caacagatcg ttttataaat ttttttttt gaaaaagaaa | 480 |
| aagcccgaaa ggcggcaacc tctcgggctt ctggatttcc gatccccgga attagatctt | 540 |
| ggcaggatat attgtggtgt aacgtatcac aagtttgtac aaaaaagcag gctccgcggc | 600 |
| cgcccccttc acctagactc gacgcgtcct agagatccgt caacatggtg gagcacgaca | 660 |
| ctctcgtcta ctccaagaat atcaaagata cagtctcaga agaccaaagg gctattgaga | 720 |
| cttttcaaca agggtaata tcgggaaacc tcctcggatt ccattgccca gctatctgtc | 780 |
| acttcatcaa aaggacagta gaaaggaag gtggcaccta caaatgccat cattgcgata | 840 |
| aaggaaaggc tatcgttcaa gatgcctctg ccgacagtgg tcccaaagat ggacccccac | 900 |
| ccacgaggag catcgtggaa aaagaagacg ttccaaccac gtcttcaaag caagtggatt | 960 |
| gatgtgatat ctccactgac gtaagggatg acgcacaatc ccactatcct tcgcaagacc | 1020 |
| cttcctctat ataaggaagt tcatttcatt tggagaggac gacccgata tgaaaaagcc | 1080 |
| tgaactcacc gcgacgtctg tcgagaagtt tctgatcgaa aagttcgaca cgtctccga | 1140 |
| cctgatgcag ctctcggagg gcgaagaatc tcgtgctttc agcttcgatg taggagggcg | 1200 |
| tggatatgtc ctgcgggtaa atagctgcgc cgatggtttc tacaaagatc gttatgttta | 1260 |
| tcggcacttt gcatcggccg cgctcccgat tccggaagtg cttgacattg ggaattcag | 1320 |
| cgagagcctg acctattgca tctcccgccg tgcacagggt gtcacgttgc aagacctgcc | 1380 |
| tgaaaccgaa ctgcccgctg ttctgcaggt aaatttctag ttttttctcct tcatttttctt | 1440 |
| ggttaggacc cttttctctt tttattttt tgagctttga tctttcttta aactgatcta | 1500 |
| tttttttaatt gattggttat ggtgtaaata ttacatagct ttaactgata atctgattac | 1560 |
| tttatttcgt gtgtctatga tgatgatgat aactgcagcc ggtcgcggag gccatggatg | 1620 |
| cgatcgctgc ggccgatctt agccagacga gcggggtcgg cccattcgga ccgcaaggaa | 1680 |
| tcggtcaata cactacatgg cgtgatttca tatgcgcgat tgctgatccc catgtgtatc | 1740 |

```
actggcaaac tgtgatggac gacaccgtca gtgcgtccgt cgcgcaggct ctcgatgagc    1800
tgatgctttg ggccgaggac tgccccgaag tccggcacct cgtgcacgcg gatttcggct    1860
ccaacaatgt cctgacggac aatggccgca taacagcggt cattgactgg agcgaggcga    1920
tgttcgggga ttcccaatac gaggtcgcca acatcttctt ctggaggccg tggttggctt    1980
gtatggagca gcagacgcgc tacttcgagc ggaggcatcc ggagcttgca ggatcgccgc    2040
ggctccgggc gtatatgctc cgcattggtc ttgaccaact ctatcagagc ttggttgacg    2100
gcaatttcga tgatgcagct tgggcgcagg tcgatgcga cgcaatcgtc cgatccggag    2160
ccgggactgt cgggcgtaca caaatcgccc gcagaagcgc ggccgtctgg accgatggct    2220
gtgtagaagt actcgccgat agtggaaacc gacgcccag cactcgtccg agggcaaagg    2280
aatagagtag atgccgaccg ggatccggag agctcgaatt ccccgatcg ttcaaacatt    2340 tggcaataaa gtttcttaag attgaatcct gttgccggtc ttgcgatgat tatcatataa    2400
tttctgttga attacgttaa gcatgtaata attaacatgt aatgcatgac gttatttatg    2460
agatgggttt ttatgattag agtcccgcaa ttatacattt aatacgcgat agaaaacaaa    2520
atatagcgcg caaactagga taaattatcg cgcgcggtgt catctatgtt actagatcgg    2580
gaattcatcg atgatatcag atcaagggtg ggcgcgccga accagctttc ttgtacaaag    2640
tggtgatccc cctcgaggtc gacggtatcg ataagcttga tatcgaattc cgtgcagcgt    2700
gacccggtcg tgcccctctc tagagataat gagcattgca tgtctaagtt ataaaaaatt    2760
accacatatt tttttgtca cacttgtttg aagtgcagtt tatctatctt tatacatata    2820 tttaacttt actctacgaa taatataatc tatagtacta caataatatc agtgttttag    2880
agaatcatat aaatgaacag ttagacatgg tctaaaggac aattgagtat tttgacaaca    2940
ggactctaca gttttatctt tttagtgtgc atgtgttctc ctttttttt gcaaatagct    3000 tcacctatat aatacttcat ccattttatt agtacatcca tttagggttt agggttaatg    3060
gtttttatag actaattttt ttagtacatc tattttattc tattttagcc tctaaattaa    3120
gaaaactaaa actctatttt agttttttta tttaataatt tagatataaa atagaataaa    3180
ataaagtgac taaaaattaa acaaataccc tttaagaaat taaaaaaact aaggaaacat    3240
ttttcttgtt tcgagtagat aatgccagcc tgttaaacgc cgtcgacgag tctaacggac    3300
accaaccagc gaaccagcag cgtcgcgtcg ggccaagcga agcagacggc acggcatctc    3360
tgtcgctgcc tctggaccc tctcgagagt tccgctccac cgttggactt gctccgctgt    3420
cggcatccag aaattgcgtg tcggacggca gacgtgagcc ggcacggcag gcggcctcct    3480
cctcctctca cggcaccggc agctacgggg gattcctttc ccaccgctcc ttcgctttcc    3540
cttcctcgcc cgccgtaata aatagacacc ccctccacac cctctttccc caacctcgtg    3600
ttgttcggag cgcacacaca cacaaccaga tctcccccaa atccacccgt cggcacctcc    3660
gcttcaaggt acgccgctcg tcctcccccc cccccctct ctaccttctc tagatcggcg    3720
ttccggtcca tggttagggc ccggtagttc tacttctgtt catgtttgtg ttagatccgt    3780
gtttgtgtta gatccgtgct gctagcgttc gtacacggat gcgacctgta cgtcagacac    3840
gttctgattg ctaacttgcc agtgtttctc tttggggaat cctgggatgg ctctagccgt    3900
tccgcagacg ggatcgattt catgattttt ttttgtttcg ttgcataggg tttggttgc    3960 ccttttcctt tatttcaata tatgccgtgc acttgtttgt cgggtcatct tttcatgctt    4020 tttttttgtct tggttgtgat gatgtggtct ggttgggcgg tcgttctaga tcggagtaga    4080
```

```
attaattctg tttcaaacta cctggtggat ttattaattt tggatctgta tgtgtgtgcc    4140
atacatattc atagttacga attgaagatg atggatggaa atatcgatct aggataggta    4200
tacatgttga tgcgggtttt actgatgcat atacagagat gcttttttgtt cgcttggttg    4260 tgatgatgtg gtgtggttgg gcggtcgttc attcgttcta gatcggagta gaatactgtt    4320
tcaaactacc tggtgtattt attaattttg gaactgtatg tgtgtgtcat acatcttcat    4380
agttacgagt ttaagatgga tggaaatatc gatctaggat aggtatacat gttgatgtgg    4440
gttttactga tgcatataca tgatggcata tgcagcatct attcatatgc tctaaccttg    4500
agtacctatc tattataata aacaagtatg ttttataatt attttgatct tgatatactt    4560
ggatgatggc atatgcagca gctatatgtg gattttttta gccctgcctt catacgctat    4620
ttatttgctt ggtactgttt cttttgtcga tgctcaccct gttgtttggt gttacttcgc    4680
ccatcacaag tttgtacaaa aaagctgaac gagaaacgta aaatgatata aatatcaata    4740
caccatgaag aggcacggtc ttgccgcccg agttcaccac gttcgccccc ttcttgtcct    4800
cctcgcggcc gtcttgctgc tcgccgccac ggtcgatggc atcagaccag atcccgatga    4860
ccatgcacgc ccggggcagg cgccaggtgc accggcggtg gaggagaaga aggatgggtc    4920
ggggttcctg caggaggagg tgtacgggac ggggtcgagc ctgccggact gcacgcacgc    4980
gtgcggcgcc tgcaagccgt gcaaccgcgt gatggtcagc ttcaagtgct ccatcgccga    5040
gccctgcccc atggtctacc gctgcatgtg caagggcaag tgctacccg tcccctccag     5100 ctaggcgcgc cgacccagct ttcttgtaca aagtggtgat gggggatcca ctagttctag    5160
aattcgattg agtcaagcag gatcgttcaa acatttggca ataaagtttc ttaagattga    5220
atcctgttgc cggtcttgcg atgattatca tataatttct gttgaattac gttaagcatg    5280
taataattaa catgtaatgc atgacgttat ttatgagatg ggttttttatg attagagtcc    5340 cgcaattata catttaatac gcgatagaaa acaaaatata gcgcgcaaac taggataaat    5400
tatcgcgcgc ggtgtcatct atgttactag atcgaccggc atgcaagctg atatcaatca    5460
ctagtgaatt ctagagcggc cgccaccgcg gtggagctcc agcttttgtt ccctttagtg    5520
agggttaatt gcgcgcttgg cgtaatcatg gtcatagctg tttcctgtgt gaaattgtta    5580
tccgctcaca attccacaca acatacgagc cggaagcata agtgtaaaag cctggggtgc    5640
ctaatgagtg agctaactca cattaattgc gttgcgctca ctgcccgctt tccagtcggg    5700
aaacctgtcg tgccagctgc attaatgaat cggccaacgc gcggggagag gcggtttgcg    5760
tattgggcgc tcttccgctt cctcgctcac tgactcgctg cgctcggtcg ttcggctgcg    5820
gcgagcggta tcagctcact caaaggcggt aatacggtta ccacagaat caggggataa     5880 cgcaggaaag aacatgaagg ccttgacagg atatattggc gggtaaacta agtcgctgta    5940
tgtgtttgtt tgagatctca tgtgagcaaa aggccagcaa aaggccagga accgtaaaaa    6000
ggccgcgttg ctggcgtttt tccataggct ccgcccccct gacgagcatc acaaaaatcg    6060
acgctcaagt cagaggtggc gaaacccgac aggactataa agataccagg cgtttccccc    6120
tggaagctcc ctcgtgcgct ctcctgttcc gaccctgccg cttaccggat acctgtccgc    6180
ctttctccct tcgggaagcg tggcgctttc tcatagctca cgctgtaggt atctcagttc    6240
ggtgtaggtc gttcgctcca agctgggctg tgtgcacgaa ccccccgttc agcccgaccg    6300
ctgcgcctta tccggtaact atcgtcttga gtccaacccg gtaagacacg acttatcgcc    6360
actggcagca gccactggta acaggattag cagagcgagg tatgtaggcg gtgctacaga    6420
gttcttgaag tggtggccta actacggcta cactagaaga acagtatttg gtatctgcgc    6480
```

```
tctgctgaag ccagttacct tcggaagaag agttggtagc tcttgatccg gcaaacaaac    6540
caccgctggt agcggtggtt ttttttgtttg caagcagcag attacgcgca gaaaaaaagg    6600
atctcaagaa gatcctttga tcttttctac ggggtctgac gctcagtgga acgaaaactc    6660
acgttaaggg attttggtca tgagattatc aaaaaggatc ttcacctaga tccttttaaa    6720
ttaaaaatga gttttaaat caatctaaag tatatatgtg taacattggt ctagtgatta    6780
gaaaaactca tcgagcatca aatgaaactg caatttattc atatcaggat tatcaatacc    6840
atatttttga aaaagccgtt tctgtaatga aggagaaaac tcaccgaggc agttccatag    6900
gatggcaaga tcctggtatc ggtctgcgat tccgactcgt ccaacatcaa tacaacctat    6960
taatttcccc tcgtcaaaaa taaggttatc aagtgagaaa tcaccatgag tgacgactga    7020
atccggtgag aatggcaaaa gtttatgcat ttctttccag acttgttcaa caggccagcc    7080
attacgctcg tcatcaaaat cactcgcatc aaccaaaccg ttattcattc gtgattgcgc    7140
ctgagcgaga cgaaatacgc gatcgctgtt aaaaggacaa ttacaaacag gaatcgaatg    7200
caaccggcgc aggaacactg ccagcgcatc aacaatattt tcacctgaat caggatattc    7260
ttctaatacc tggaatgctg ttttccctgg gatcgcagtg gtgagtaacc atgcatcatc    7320
aggagtacgg ataaaatgct tgatggtcgg aagaggcata aattccgtca gccagtttag    7380
tctgaccatc tcatctgtaa caacattggc aacgctacct ttgccatgtt tcagaaacaa    7440
ctctggcgca tcgggcttcc catacaatcg gtagattgtc gcacctgatt gcccgacatt    7500
atcgcgagcc catttatacc catataaatc agcatccatg ttggaattta atcgcggcct    7560
tgagcaagac gtttcccgtt gaatatggct cataacaccc cttgtattac tgtttatgta    7620
agcagacagt tttattgttc atgatgatat atttttatct tgtgcaatgt aacatcagag    7680
attttgagac acaacgtggc tttgttgaat aaatcgaact tttgctgagt tgaaggatca    7740
gatcacgcat cttcccgaca acgcagaccg ttccgtggca agcaaaagt tcaaaatcac    7800 caactggtcc acctacaaca aagctctcat caaccgtggc tccctcactt tctggctgga    7860
tgatggggcg attcaggcga tccccatcca acagcccgcc gtcgagcggg ct            7912
```

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Hygromycin Forward Primer

<400> SEQUENCE: 17
actcaccgcg acgtctg                                                    17

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Hygromycin Reverse Primer

<400> SEQUENCE: 18
gcgcgtctgc tgctccata                                                  19

```
<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: HvGAPDH Forward Primer

<400> SEQUENCE: 19
gtgaggctgg tgctgatt                                                 18

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: HvGAPDH Reverse Primer

<400> SEQUENCE: 20
cgtggtgcag ctagcatttg agac                                          24

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: HvTubulin Forward Primer

<400> SEQUENCE: 21
agtgtcctgt ccacccactc                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: HvTubulin Reverse Primer

<400> SEQUENCE: 22
agcatgaagt ggatccttgg                                               20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: HvEPF1 Forward Primer (qPCR)

<400> SEQUENCE: 23
gtggaggaga agaaggatgg                                               20

<210> SEQ ID NO 24
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: HvEPF1 Reverse Primer (qPCR)

<400> SEQUENCE: 24
atggagcact tgaagctgac                                                  20

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: HvEPF1 Forward Primer (vector construction)

<400> SEQUENCE: 25
caccatgaag aggcacggtc tt                                               22

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: HvEPF1 Reverse Primer (vector construction)

<400> SEQUENCE: 26
ctagctggag gggacggggt                                                  20

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: OsEPF2 Forward Primer

<400> SEQUENCE: 27
caccatgagg aggcacgcta ctc                                              23

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: OsEPF2 Reverse Primer

<400> SEQUENCE: 28
ctagctggag ggcacagggt a                                                21

<210> SEQ ID NO 29
<211> LENGTH: 120
<212> TYPE: PRT
<213> ORGANISM: Arabidopsis thaliana

<400> SEQUENCE: 29
```

Met Thr Lys Phe Val Arg Lys Tyr Met Phe Cys Leu Val Leu Val Phe
1               5                   10                  15

Ala Ala Cys Ser Leu Val Val Asn Ser Ile Arg Thr Pro Pro Leu Lys
            20                  25                  30

Asn Thr Val Asn Gly Gly Glu Lys Lys Asn Ala Asp Ile Glu Gln Ala
        35                  40                  45

Gln Thr His His Lys Lys Glu Ile Ser Lys Asn Gly Gly Val Glu Met
    50                  55                  60

Glu Met Tyr Pro Thr Gly Ser Ser Leu Pro Asp Cys Ser Tyr Ala Cys
65                  70                  75                  80

Gly Ala Cys Ser Pro Cys Lys Arg Val Met Ile Ser Phe Glu Cys Ser
                85                  90                  95

Val Ala Glu Ser Cys Ser Val Ile Tyr Arg Cys Thr Cys Arg Gly Arg
            100                 105                 110

Tyr Tyr His Val Pro Ser Arg Ala
        115                 120

<210> SEQ ID NO 30
<211> LENGTH: 104
<212> TYPE: PRT
<213> ORGANISM: Arabidopsis thaliana

<400> SEQUENCE: 30

Met Lys Ser Leu Leu Leu Ala Phe Phe Leu Ser Phe Phe Gly
1               5                   10                  15

Ser Leu Leu Ala Arg His Leu Pro Thr Ser Ser His Pro Ser His His
            20                  25                  30

His Val Gly Met Thr Gly Ala Leu Lys Arg Gln Arg Arg Arg Pro Asp
        35                  40                  45

Thr Val Gln Val Ala Gly Ser Arg Leu Pro Asp Cys Ser His Ala Cys
    50                  55                  60

Gly Ser Cys Ser Pro Cys Arg Leu Val Met Val Ser Phe Val Cys Ala
65                  70                  75                  80

Ser Val Glu Glu Ala Glu Thr Cys Pro Met Ala Tyr Lys Cys Met Cys
                85                  90                  95

Asn Asn Lys Ser Tyr Pro Val Pro
            100

<210> SEQ ID NO 31
<211> LENGTH: 309
<212> TYPE: DNA
<213> ORGANISM: Arabidopsis thaliana

<400> SEQUENCE: 31
atgaagcatg aaatgatgaa catcaagcca agatgcataa ccatcttctt tcttctttt      60 gctttgcttc ttggaaatta tgtagttcaa gcctcaagac ctcgttctat cgaaaatacg    120
gtctcccttc tcccacaagt acatctcctg aattcaagga ggaggcatat gatagggtcg    180
acagcaccaa cttgtacgta caacgagtgc agaggatgca gatacaagtg cagagcagag    240
caagttccag tcgaaggaaa tgaccctatc aacagtgctt atcattatag atgtgtttgt    300
catagataa                                                             309

<210> SEQ ID NO 32
<211> LENGTH: 411
<212> TYPE: DNA
<213> ORGANISM: Arabidopsis thaliana

<400> SEQUENCE: 32

```
atggatcatg tgaatccaac actgtttcat ttaaaatccc tttcaatctt tactctcact      60
ctcttatata tctcttcacc acatttctt ttgttcaaaa ccctttctat gtatgagaac     120
ctaagaatat ttctaaaaat aatacccttc aatcttttcg gaatgaaatc ggtatcttta     180
atcgcgattc ttcttctcca tcttttgtt agtagtgata ctttccagtt ggatcttttt      240
cactataagg cgagcggatc aagcatacct gactgttcga atgcgtgtgg accatgtaaa     300
ccatgcaagc ttgtcgtgat cagttctacg tgctccgcct ccgaggcttg ccctctcgtc     360
tacaagtgct gtgtaaagg caaatactat cacgtgcctt ccctcaccta a               411
```

<210> SEQ ID NO 33
<211> LENGTH: 363
<212> TYPE: DNA
<213> ORGANISM: Arabidopsis thaliana

<400> SEQUENCE: 33

```
atgacgaagt ttgtacgcaa gtatatgttt tgcctcgtcc tagtcttcgc cgcgtgttct      60
ttggtcgtta actccattcg cacgccgcca ctaaaaaaca cggtcaatgg cggagaaaag     120
aaaaacgccg atatagaaca agctcaaacg caccacaaga aggaaataag caaaaacgga     180
ggggtagaaa tggaaatgta cccaacagga tcaagcttac cggattgttc atacgcgtgt     240
ggcgcatgtt cgccgtgtaa acgtgtgatg attagtttcg aatgctcagt cgccgaatca     300
tgtagcgtca tctacagatg cacgtgcaga gggagatact atcacgtgcc atctagagct     360
tga                                                                   363
```

<210> SEQ ID NO 34
<211> LENGTH: 315
<212> TYPE: DNA
<213> ORGANISM: Arabidopsis thaliana

<400> SEQUENCE: 34

```
atgaagtctc ttcttctcct tgcctttttc ctctctttct tctttggctc tctcttggct      60
aggcatttac caacatcctc ccatccaagt catcatcatg taggaatgac cggggcattg     120
aagcgtcaga ggaggaggcc ggacacggtg caggtggctg ggtctaggtt gccagattgc     180
tcacacgcgt gtggctcgtg ttctccatgc cgtcttgtga tggttagctt tgtgtgtgca     240
tccgtcgaag aggctgagac ttgtccaatg gcttataaat gcatgtgcaa caataagtcc     300
taccctgtcc cttga                                                      315
```

<210> SEQ ID NO 35
<211> LENGTH: 501
<212> TYPE: DNA
<213> ORGANISM: Zea mays

<400> SEQUENCE: 35

```
atgacgacga cgacgcgcgc ggcgcgccct accccagcag cagcagcagc ggtcgtgttg      60
gtgttcctgc tgctcatcgt cagttcgtcg tcgtcgcacg tcgttgccga cgacggcgcc     120
agaacgacga caccacgtga ccacgccgcc ctgctccacg cggaggcatc ggctgctgct     180
ggtgctcacg cgagcagcgg cagcagcagg gcaacctact acagaccagc gggccggagt     240
gaggacgggt cgccgtcggt ggtggtggcg gcggcggcgg aggaggagga ggaggaggat     300
aagctgtggt ggctcaagga gcgcgcggcg gcgacggggt cgcggctgcc ggactgcgcg     360
cacgcgtgcg ggccgtgctc cccgtgccgg cgcgtcatcg tgagcttcag gtgcgcgatg     420
```

```
caggcctccg agtcctgccc cgtcgcctac cgctgcatgt gccgcggcag gttctttcgg    480
gtgccttccc cgctagacta g                                              501

<210> SEQ ID NO 36
<211> LENGTH: 447
<212> TYPE: DNA
<213> ORGANISM: Oryza sativa

<400> SEQUENCE: 36
atgagcatga tgtttagtgc cagagcgcta gcgtttgcgt ttgcagtggt cgtgatgagc     60
tcgtgcgtcg ctgatggcgt caggacgata ccagcaggtg ggcaagattc agccggtggg    120
ctacacaacg gcggcacgtc tccatctgct gctgctgcga acgggagcac caccgccgcc    180
tacgacgaca gcggcgccgg cggccagacg gcgacgttcc aggtgcagca gggcgcacag    240
ccggaggaag agacgacgac ggagatgggc aacgcggcgg aggcggcgac gggatcgcgg    300
ctgccggact gcacgcacgc gtgcgggccg tgctccccgt gccggcgcgt gatggtgagc    360
ctccgatgcg ccgaggccgc ggagtcgtgc cccgtcgcgt accgctgcat gtgccgcggc    420
aggttcttcc gcgtgcccac cctctag                                       447

<210> SEQ ID NO 37
<211> LENGTH: 318
<212> TYPE: DNA
<213> ORGANISM: Hordeum vulgare

<400> SEQUENCE: 37
atggcctcct gctcgtgcgt gacccatggc accagaacca caccaagttc aggtgccgat     60
gccctgcaac ctggccgtga ggcgacgccc ggagggcaag cggcctcgcc gtcgtcccat    120
caggagaagc aagggatgat gctcaaggag ggagcggtga cggggtcgcg gctgccggac    180
tgcgcgcacg cgtgcgggGc gtgcgccccg tgcaagcggg tcatggtgag cttccggtgc    240
gccgaggcct ccgagtcgtg ccccatcgcc taccgctgca tgtgccgcgg caggttcttc    300 cgcgtccccca ccctctag                                                318

<210> SEQ ID NO 38
<211> LENGTH: 426
<212> TYPE: DNA
<213> ORGANISM: Triticum aestivum

<400> SEQUENCE: 38
atgaggaggc ctgctggcgt gggagctcgg tgggcgctgg cgctggccct tgcgctggcc     60
acggcctcgt gctcgtgcgt gacccatggc gccagaacca caccaacagg ttcaggcgcc    120
gacgtcctac gacctggcgg tgaggcgacg ccctccggaa ccgcaggcca ggacgactac    180
agaggacagg cggcatcccc gtcaaatcag cagaagcggg aggggagggg gcagcaaggg    240
atgatgacgc tcaaggagcg agcggtgacg gggtcgcggc tgccggactg cgcgcacgcg    300
tgcggggcgt gcgcgccgtg caagcgggtc atggtcagct tccggtgcgc cgaggcctcc    360
gagtcgtgcc ccatcgccta ccgctgcatg tgccacggca ggttcttccg cgtccccgcc    420
ctctag                                                              426

<210> SEQ ID NO 39
<211> LENGTH: 447
<212> TYPE: DNA
<213> ORGANISM: Triticum aestivum
```

```
<400> SEQUENCE: 39
atgaggaggc ctgctggcgt gggagctcgg tgggcgctgg cccttgcgct ggccatggca    60
tcggcatcgt gctcgtgcgt gacccatggt gccagaacca caccaacagg tttaggcgcc   120
cgcggcctac gacctggcgg tgaggcgacg ccgtccggaa ccgcatgccg ggacgacgac   180
gacgacggag ggcaggcggc accaccgtcc catcaggaga agcggggcca ggcgacgggg   240
gagagggagg aggaacaagg gatgacgacg ctcaaggagc gagcggtgac ggggtcgcgg   300
ctgccggact gcgcgcacgc gtgcggggcg tgcgccccgt gcaagcgggt catggtcagc   360
ttccggtgcg ccgaggcctc cgagtcgtgc ccatcgcct accgctgcat gtgccgcggc   420
aggttcttcc gcgtccccac cctctag                                      447

<210> SEQ ID NO 40
<211> LENGTH: 450
<212> TYPE: DNA
<213> ORGANISM: Triticum aestivum

<400> SEQUENCE: 40
atgaggaggc ctgctggcgt gggagctcgg tgggcgccgg cgctggccct tgcgctggcc    60
atggcattgg cgtcgtgctc gtgcgtgacc catggcgcca gaaccacacc aacaggttca   120
ggcgccgacg gcctacgacc tggccgtgag gcgacgccgt ccggaaccgc aggccgggac   180
gacaacgacg gagggcaggc ggcatcaccg tcccatcagg aagcggggcc aggcgacg     240 cgggaggggg aggaggagca agggatgatg acgctcaagg agcgagcggt gacggggtcg   300
cggctgccgg actgcgcgca cgcgtgcggg gcgtgcgccc cgtgcaagcg ggtcatggtc   360
agcttccggt gcgccgaggc ctccgagtcg tgccccatcg cctaccgctg catgtgccgc   420
ggcaggttct tccgcgtccc caccctctag                                   450

<210> SEQ ID NO 41
<211> LENGTH: 408
<212> TYPE: DNA
<213> ORGANISM: Zea mays

<400> SEQUENCE: 41
atggggaggc acgctggcgg cgtccttctc gctctgacgg tggtgctgct gctcgccgcc    60
gcgagtggtg gcgtcagacc agctgatcct gctgctgggg ccaataataa cggactggcg   120
catggatcaa cggcggcggc ggagatggtc gtagctgcgc cgtcagctgc acagcagctg   180
cagctgcagg ggaggagaag caaggacgac gacggcgtgc ttctgcggga ggaggtggtg   240
cgcgcgacgg ggtcgagcct cccggactgc tcgcacgcgt gcggggcgtg ctcgccgtgc   300
agccgcgtca tggtcagctt caagtgctcc gcggccgagc cgctgccgtg ccccatggtg   360
taccgctgca tgtgcagggg caagtgctac ccggtgccct ccagctga              408

<210> SEQ ID NO 42
<211> LENGTH: 339
<212> TYPE: DNA
<213> ORGANISM: Zea mays

<400> SEQUENCE: 42
atggggaggc acactggtgc tggaattcac tgctccgtcc ctctcgctct gacggtagta    60
gtgctgctgc tgctcgcctc cgtctcactg atgcagggga ggcagatgag caggggcggc   120
aagaaggacg acgacggcga cgacaacgtg ctgctgcggg aggaggtggt gcgcgcgacg   180
gggtcgagcc tcccggactg ctcgcacgcg tgcggggcgt gctcgccgtg cagccgcgtc   240
```

```
atggtcagct tcaagtgctc cgccgccgag ccgctgccgt gccccatggt gtaccgctgc    300
atgtgcaggg gcaaatgcta cccggtgccg tccagctga                          339

<210> SEQ ID NO 43
<211> LENGTH: 411
<212> TYPE: DNA
<213> ORGANISM: Oryza sativa

<400> SEQUENCE: 43
atgaggaggc acgctactct tgctgacgcc cgaggtcacc accgcatcct tctcatactc    60
gcagtcgtcc tgcttcttgc tgccaccggc gatggcatca gatcgccccc cttttccaca   120
gatgatgtag taacaccggt gcatggtgca caagacgaaa agatcagcgc tactgcgaca   180
cttgtgatct caccacagca ggccacagct ggggacaacg tcggccgcgg cgtcctgcag   240
gaggaggtgc gcgcgacggg gtcgagcctg ccggactgct cgcacgcgtg cggcgcctgc   300
tcgccgtgca accgcgtcat ggtgagcttc aagtgctcca tcgcggagcc gtgcccgatg   360
gtgtaccgct gcatgtgcaa gggcaagtgc taccctgtgc cctccagcta g            411

<210> SEQ ID NO 44
<211> LENGTH: 384
<212> TYPE: DNA
<213> ORGANISM: Triticum aestivum

<400> SEQUENCE: 44
atgacgaaga ggcacggtcc tgccgcccga gttcaccgcg ttcaccccct tcttctcctc    60
ctcgcggccg tcttgctgct cgctgccacg gctgatggca tcagaccggg ccccgatgat   120
gctgatgcga aaccggcagt gcagcgtgca cggccggggc aggcgcctgg tgcggcgacg   180
gcgacggcga cggaggagaa ggggttcctg caggaggagg tgtacgggac ggggtcgagc   240
ctgccggact gcacgcacgc gtgcggcgcc tgcaagccgt gcaaccgcgt catggtcagc   300
ttcaagtgct ccatcgccga gcctgcccca atggtctacc gctgcatgtg caagggcaag   360
tgctaccctg tcccctcaag ctag                                          384

<210> SEQ ID NO 45
<211> LENGTH: 393
<212> TYPE: DNA
<213> ORGANISM: Triticum aestivum

<400> SEQUENCE: 45
atgatgatga ggcatggtct tgtcgcccga gttcaccgcg ctcatcccct tcttctgctc    60
ctcgcggccg tcttgttgct caccgccacg gctgatggca tcagaccggg ccccgatgat   120
gctgatgcaa gaccggcagt gcagcgtgca cggccggggc atgcgcctgg tgctgcggcg   180
acggagacgg aggagaagaa ggatgtgtcg gggttcctgc aggaggaggt gtacgggacg   240
gggtcgagcc tgccggactg cacgcacgcg tgcggcgcct gcaagccgtg caaccgcgtg   300
atgatcagct tcaagtgctc catcgccgag ccctgcccca tggtctaccg ctgcatgtgc   360
aagggcaagt gctaccccgt tccctccagc tag                                393

<210> SEQ ID NO 46
<211> LENGTH: 348
<212> TYPE: DNA
<213> ORGANISM: Triticum aestivum

<400> SEQUENCE: 46
```

```
atgaagacga gcggtctcgc cgcccgagtt caccacgctc gtcttcttct cctcctcgcg    60
gccgtcttgc tgctcgccgc cacggctgat ggcatcagac caggccccca tgaccatgca   120
cggccggggc aggcgcctgg tgcggcgacg gcgacggagg agaagggtt cctgcaggag    180 gaggtgtacg ggacggggtc gagcctgccg gactgcacgc acgcgtgcgg cgcctgcaag   240
ccgtgcaacc gcgtgatggt cagcttcaag tgctccatcg ccgagccctg ccccatggtc   300
taccgctgca tgtgcaaggg caagtgctac cccgtcccct ccagctag                348
```

<210> SEQ ID NO 47
<211> LENGTH: 166
<212> TYPE: PRT
<213> ORGANISM: Zea mays

<400> SEQUENCE: 47

```
Met Thr Thr Thr Thr Arg Ala Ala Arg Pro Thr Pro Ala Ala Ala
1               5                   10                  15

Ala Val Val Leu Val Phe Leu Leu Leu Ile Val Ser Ser Ser Ser
                20                  25                  30

His Val Val Ala Asp Asp Gly Ala Arg Thr Thr Thr Pro Arg Asp His
            35                  40                  45

Ala Ala Leu Leu His Ala Glu Ala Ser Ala Ala Ala Gly Ala His Ala
        50                  55                  60

Ser Ser Gly Ser Ser Arg Ala Thr Tyr Tyr Arg Pro Ala Gly Arg Ser
65                  70                  75                  80

Glu Asp Gly Ser Pro Ser Val Val Ala Ala Ala Glu Glu Glu
                85                  90                  95

Glu Glu Glu Asp Lys Leu Trp Trp Leu Lys Glu Arg Ala Ala Thr
            100                 105                 110

Gly Ser Arg Leu Pro Asp Cys Ala His Ala Cys Gly Pro Cys Ser Pro
        115                 120                 125

Cys Arg Arg Val Ile Val Ser Phe Arg Cys Ala Met Gln Ala Ser Glu
130                 135                 140

Ser Cys Pro Val Ala Tyr Arg Cys Met Cys Arg Gly Arg Phe Phe Arg
145                 150                 155                 160

Val Pro Ser Pro Leu Asp
                165
```

<210> SEQ ID NO 48
<211> LENGTH: 148
<212> TYPE: PRT
<213> ORGANISM: Oryza sativa

<400> SEQUENCE: 48

```
Met Ser Met Met Phe Ser Ala Arg Ala Leu Ala Phe Ala Phe Ala Val
1               5                   10                  15

Val Val Met Ser Ser Cys Val Ala Asp Gly Val Arg Thr Ile Pro Ala
                20                  25                  30

Gly Gly Gln Asp Ser Ala Gly Gly Leu His Asn Gly Thr Ser Pro
            35                  40                  45

Ser Ala Ala Ala Ala Asn Gly Ser Thr Thr Ala Ala Tyr Asp Asp Ser
        50                  55                  60

Gly Ala Gly Gly Gln Thr Ala Thr Phe Gln Val Gln Gly Ala Gln
65                  70                  75                  80

Pro Glu Glu Glu Thr Thr Thr Glu Met Gly Asn Ala Ala Glu Ala Ala
                85                  90                  95
```

-continued

```
Thr Gly Ser Arg Leu Pro Asp Cys Thr His Ala Cys Gly Pro Cys Ser
            100                 105                 110

Pro Cys Arg Arg Val Met Val Ser Leu Arg Cys Ala Glu Ala Ala Glu
        115                 120                 125

Ser Cys Pro Val Ala Tyr Arg Cys Met Cys Arg Gly Arg Phe Phe Arg
130                 135                 140

Val Pro Thr Leu
145

<210> SEQ ID NO 49
<211> LENGTH: 122
<212> TYPE: PRT
<213> ORGANISM: Hordeum vulgare

<400> SEQUENCE: 49

Met Arg Lys Ser Ala Gly Val Gly Ala Leu Ala Leu Ala Leu Ala Leu
1               5                   10                  15

Ala Met Ala Ser Cys Ser Cys Val Thr His Gly Thr Arg Thr Thr Pro
            20                  25                  30

Ser Ser Gly Ala Asp Ala Leu Gln Pro Gly Arg Glu Ala Thr Pro Gly
        35                  40                  45

Gly Gln Ala Ala Ser Pro Ser Ser His Gln Glu Lys Gln Gly Met Met
    50                  55                  60

Leu Lys Glu Gly Ala Val Thr Gly Ser Arg Leu Pro Asp Cys Ala His
65                  70                  75                  80

Ala Cys Gly Ala Cys Ala Pro Cys Lys Arg Val Met Val Ser Phe Arg
                85                  90                  95

Cys Ala Glu Ala Ser Glu Ser Cys Pro Ile Ala Tyr Arg Cys Met Cys
            100                 105                 110

Arg Gly Arg Phe Phe Arg Val Pro Thr Leu
        115                 120

<210> SEQ ID NO 50
<211> LENGTH: 148
<212> TYPE: PRT
<213> ORGANISM: Triticum aestivum

<400> SEQUENCE: 50

Met Arg Arg Pro Ala Gly Val Gly Ala Arg Trp Ala Pro Ala Leu Ala
1               5                   10                  15

Leu Ala Leu Ala Met Ala Leu Ala Ser Cys Ser Cys Val Thr His Gly
            20                  25                  30

Ala Arg Thr Thr Pro Ser Ser Gly Ala Asp Gly Leu Arg Pro Gly Arg
        35                  40                  45

Glu Ala Thr Pro Ser Gly Thr Ala Gly Arg Asp Asp Asn Asp Gly Gly
    50                  55                  60

Gln Ala Ala Ser Pro Ser His Gln Glu Lys Arg Gly Gln Ala Thr Arg
65                  70                  75                  80

Glu Gly Glu Glu Glu Gln Gly Met Met Thr Leu Lys Glu Arg Ala Val
                85                  90                  95

Thr Gly Ser Arg Leu Pro Asp Cys Ala His Ala Cys Gly Ala Cys Ala
            100                 105                 110

Pro Cys Lys Arg Val Met Val Ser Phe Arg Cys Ala Glu Ala Ser Glu
        115                 120                 125

Ser Cys Pro Ile Ala Tyr Arg Cys Met Cys Arg Gly Arg Phe Phe Arg
130                 135                 140
```

```
Val Pro Thr Leu
145

<210> SEQ ID NO 51
<211> LENGTH: 147
<212> TYPE: PRT
<213> ORGANISM: Triticum aestivum

<400> SEQUENCE: 51

Met Arg Arg Pro Ala Gly Val Gly Ala Arg Trp Ala Leu Ala Leu Ala
1               5                   10                  15

Leu Ala Met Ala Ser Ala Ser Cys Ser Cys Val Thr His Gly Ala Arg
            20                  25                  30

Thr Thr Pro Ser Leu Gly Ala Arg Gly Leu Arg Pro Gly Gly Glu Ala
        35                  40                  45

Thr Pro Ser Gly Thr Ala Cys Arg Asp Asp Asp Asp Gly Gly Gln
    50                  55                  60

Ala Ala Pro Pro Ser His Gln Glu Lys Arg Gly Gln Ala Thr Gly Glu
65                  70                  75                  80

Arg Glu Glu Glu Gln Gly Met Thr Thr Leu Lys Glu Arg Ala Val Thr
                85                  90                  95

Gly Ser Arg Leu Pro Asp Cys Ala His Ala Cys Gly Ala Cys Ala Pro
            100                 105                 110

Cys Lys Arg Val Met Val Ser Phe Arg Cys Ala Glu Ala Ser Glu Ser
        115                 120                 125

Cys Pro Ile Ala Tyr Arg Cys Met Cys Arg Gly Arg Phe Phe Arg Val
    130                 135                 140

Pro Thr Leu
145

<210> SEQ ID NO 52
<211> LENGTH: 140
<212> TYPE: PRT
<213> ORGANISM: Triticum aestivum

<400> SEQUENCE: 52

Met Arg Arg Pro Ala Gly Val Gly Ala Arg Trp Ala Leu Ala Leu Ala
1               5                   10                  15

Leu Ala Leu Ala Thr Ala Ser Cys Ser Cys Val Thr His Gly Ala Arg
            20                  25                  30

Thr Thr Pro Ser Ser Gly Ala Asp Val Leu Arg Pro Gly Gly Glu Ala
        35                  40                  45

Thr Pro Ser Gly Thr Ala Gly Gln Asp Asp Tyr Arg Gly Gln Ala Ala
    50                  55                  60

Ser Pro Ser Asn Gln Gln Lys Arg Glu Gly Glu Gly Gln Gln Gly Met
65                  70                  75                  80

Met Thr Leu Lys Glu Arg Ala Val Thr Gly Ser Arg Leu Pro Asp Cys
                85                  90                  95

Ala His Ala Cys Gly Ala Cys Ala Pro Cys Lys Arg Val Met Val Ser
            100                 105                 110

Phe Arg Cys Ala Glu Ala Ser Glu Ser Cys Pro Ile Ala Tyr Arg Cys
        115                 120                 125

Met Cys His Gly Arg Phe Phe Arg Val Pro Ala Leu
    130                 135                 140

<210> SEQ ID NO 53
<211> LENGTH: 112
```

-continued

```
<212> TYPE: PRT
<213> ORGANISM: Zea mays

<400> SEQUENCE: 53

Met Gly Arg His Thr Gly Ala Gly Ile His Cys Ser Val Pro Leu Ala
1               5                   10                  15

Leu Thr Val Val Val Leu Leu Leu Ala Ser Val Ser Leu Met Gln
            20                  25                  30

Gly Arg Gln Met Ser Arg Gly Gly Lys Lys Asp Asp Asp Gly Asp Asp
            35                  40                  45

Asn Val Leu Leu Arg Glu Glu Val Val Arg Ala Thr Gly Ser Ser Leu
        50                  55                  60

Pro Asp Cys Ser His Ala Cys Gly Ala Cys Ser Pro Cys Ser Arg Val
65                  70                  75                  80

Met Val Ser Phe Lys Cys Ser Ala Ala Glu Pro Leu Pro Cys Pro Met
                85                  90                  95

Val Tyr Arg Cys Met Cys Arg Gly Lys Cys Tyr Pro Val Pro Ser Ser
            100                 105                 110

<210> SEQ ID NO 54
<211> LENGTH: 115
<212> TYPE: PRT
<213> ORGANISM: Triticum aestivum

<400> SEQUENCE: 54

Met Lys Thr Ser Gly Leu Ala Ala Arg Val His His Ala Arg Leu Leu
1               5                   10                  15

Leu Leu Leu Ala Ala Val Leu Leu Ala Ala Thr Ala Asp Gly Ile
            20                  25                  30

Arg Pro Gly Pro His Asp His Ala Arg Pro Gly Gln Ala Pro Gly Ala
            35                  40                  45

Ala Thr Ala Thr Glu Glu Lys Gly Phe Leu Gln Glu Glu Val Tyr Gly
        50                  55                  60

Thr Gly Ser Ser Leu Pro Asp Cys Thr His Ala Cys Gly Ala Cys Lys
65                  70                  75                  80

Pro Cys Asn Arg Val Met Val Ser Phe Lys Cys Ser Ile Ala Glu Pro
                85                  90                  95

Cys Pro Met Val Tyr Arg Cys Met Cys Lys Gly Lys Cys Tyr Pro Val
            100                 105                 110

Pro Ser Ser
        115

<210> SEQ ID NO 55
<211> LENGTH: 127
<212> TYPE: PRT
<213> ORGANISM: Triticum aestivum

<400> SEQUENCE: 55

Met Thr Lys Arg His Gly Pro Ala Ala Arg Val His Arg Val His Pro
1               5                   10                  15

Leu Leu Leu Leu Leu Ala Ala Val Leu Leu Ala Ala Thr Ala Asp
            20                  25                  30

Gly Ile Arg Pro Gly Pro Asp Asp Ala Asp Ala Lys Pro Ala Val Gln
            35                  40                  45

Arg Ala Arg Pro Gly Gln Ala Pro Gly Ala Ala Thr Ala Thr Ala Thr
        50                  55                  60

Glu Glu Lys Gly Phe Leu Gln Glu Glu Val Tyr Gly Thr Gly Ser Ser
```

```
                65                  70                  75                  80
Leu Pro Asp Cys Thr His Ala Cys Gly Ala Cys Lys Pro Cys Asn Arg
                    85                  90                  95

Val Met Val Ser Phe Lys Cys Ser Ile Ala Glu Pro Cys Pro Met Val
                    100                 105                 110

Tyr Arg Cys Met Cys Lys Gly Lys Cys Tyr Pro Val Pro Ser Ser
                    115                 120                 125

<210> SEQ ID NO 56
<211> LENGTH: 130
<212> TYPE: PRT
<213> ORGANISM: Triticum aestivum

<400> SEQUENCE: 56

Met Met Met Arg His Gly Leu Val Ala Arg Val His Arg Ala His Pro
1               5                   10                  15

Leu Leu Leu Leu Leu Ala Ala Val Leu Leu Thr Ala Thr Ala Asp
                20                  25                  30

Gly Ile Arg Pro Gly Pro Asp Ala Asp Ala Arg Pro Ala Val Gln
            35                  40                  45

Arg Ala Arg Pro Gly His Ala Pro Gly Ala Ala Thr Glu Thr Glu
    50                  55                  60

Glu Lys Lys Asp Val Ser Gly Phe Leu Gln Glu Val Tyr Gly Thr
65                  70                  75                  80

Gly Ser Ser Leu Pro Asp Cys Thr His Ala Cys Gly Ala Cys Lys Pro
                85                  90                  95

Cys Asn Arg Val Met Ile Ser Phe Lys Cys Ser Ile Ala Glu Pro Cys
                    100                 105                 110

Pro Met Val Tyr Arg Cys Met Cys Lys Gly Lys Cys Tyr Pro Val Pro
                    115                 120                 125

Ser Ser
    130

<210> SEQ ID NO 57
<211> LENGTH: 136
<212> TYPE: PRT
<213> ORGANISM: Oryza sativa

<400> SEQUENCE: 57

Met Arg Arg His Ala Thr Leu Ala Asp Ala Arg Gly His His Arg Ile
1               5                   10                  15

Leu Leu Ile Leu Ala Val Val Leu Leu Ala Ala Thr Gly Asp Gly
                20                  25                  30

Ile Arg Ser Pro Pro Phe Ser Thr Asp Asp Val Val Thr Pro Val His
            35                  40                  45

Gly Ala Gln Asp Glu Lys Ile Ser Ala Thr Ala Thr Leu Val Ile Ser
    50                  55                  60

Pro Gln Gln Ala Thr Ala Gly Asp Asn Val Gly Arg Gly Val Leu Gln
65                  70                  75                  80

Glu Glu Val Arg Ala Thr Gly Ser Ser Leu Pro Asp Cys Ser His Ala
                85                  90                  95

Cys Gly Ala Cys Ser Pro Cys Asn Arg Val Met Val Ser Phe Lys Cys
                    100                 105                 110

Ser Ile Ala Glu Pro Cys Pro Met Val Tyr Arg Cys Met Cys Lys Gly
                    115                 120                 125

Lys Cys Tyr Pro Val Pro Ser Ser
```

-continued

```
        130             135
```

<210> SEQ ID NO 58
<211> LENGTH: 81
<212> TYPE: PRT
<213> ORGANISM: Arabidopsis thaliana

<400> SEQUENCE: 58

Met Lys Ser Val Ser Leu Ile Ala Ile Leu Leu His Leu Phe Val
1               5                   10                  15

Ser Ser Asp Thr Phe Gln Leu Asp Leu Phe His Tyr Lys Ala Ser Gly
                20                  25                  30

Ser Ser Ile Pro Asp Cys Ser Asn Ala Cys Gly Pro Cys Lys Pro Cys
            35                  40                  45

Lys Leu Val Val Ile Ser Ser Thr Cys Ser Ala Ser Glu Ala Cys Pro
50                  55                  60

Leu Val Tyr Lys Cys Leu Cys Lys Gly Lys Tyr Tyr His Val Pro Ser
65                  70                  75                  80

Leu

<210> SEQ ID NO 59
<211> LENGTH: 102
<212> TYPE: PRT
<213> ORGANISM: Arabidopsis thaliana

<400> SEQUENCE: 59

Met Lys His Glu Met Met Asn Ile Lys Pro Arg Cys Ile Thr Ile Phe
1               5                   10                  15

Phe Leu Leu Phe Ala Leu Leu Leu Gly Asn Tyr Val Val Gln Ala Ser
                20                  25                  30

Arg Pro Arg Ser Ile Glu Asn Thr Val Ser Leu Leu Pro Gln Val His
            35                  40                  45

Leu Leu Asn Ser Arg Arg Arg His Met Ile Gly Ser Thr Ala Pro Thr
50                  55                  60

Cys Thr Tyr Asn Glu Cys Arg Gly Cys Arg Tyr Lys Cys Arg Ala Glu
65                  70                  75                  80

Gln Val Pro Val Glu Gly Asn Asp Pro Ile Asn Ser Ala Tyr His Tyr
                85                  90                  95

Arg Cys Val Cys His Arg
            100

<210> SEQ ID NO 60
<211> LENGTH: 136
<212> TYPE: PRT
<213> ORGANISM: Arabidopsis thaliana

<400> SEQUENCE: 60

Met Asp His Val Asn Pro Thr Leu Phe His Leu Lys Ser Leu Ser Ile
1               5                   10                  15

Phe Thr Leu Thr Leu Leu Tyr Ile Ser Ser Pro His Phe Leu Leu Phe
                20                  25                  30

Lys Thr Leu Ser Met Tyr Glu Asn Leu Arg Ile Phe Leu Lys Ile Ile
            35                  40                  45

Pro Phe Asn Leu Phe Gly Met Lys Ser Val Ser Leu Ile Ala Ile Leu
50                  55                  60

Leu Leu His Leu Phe Val Ser Ser Asp Thr Phe Gln Leu Asp Leu Phe
65                  70                  75                  80

```
His Tyr Lys Ala Ser Gly Ser Ser Ile Pro Asp Cys Ser Asn Ala Cys
                85              90              95

Gly Pro Cys Lys Pro Cys Lys Leu Val Val Ile Ser Ser Thr Cys Ser
            100             105             110

Ala Ser Glu Ala Cys Pro Leu Val Tyr Lys Cys Leu Cys Lys Gly Lys
        115             120             125

Tyr Tyr His Val Pro Ser Leu Thr
    130             135

<210> SEQ ID NO 61
<211> LENGTH: 105
<212> TYPE: PRT
<213> ORGANISM: Hordeum vulgare

<400> SEQUENCE: 61

Met Ala Ser Cys Ser Cys Val Thr His Gly Thr Arg Thr Thr Pro Ser
1               5               10              15

Ser Gly Ala Asp Ala Leu Gln Pro Gly Arg Glu Ala Thr Pro Gly Gly
            20              25              30

Gln Ala Ala Ser Pro Ser Ser His Gln Glu Lys Gln Gly Met Met Leu
        35              40              45

Lys Glu Gly Ala Val Thr Gly Ser Arg Leu Pro Asp Cys Ala His Ala
    50              55              60

Cys Gly Ala Cys Ala Pro Cys Lys Arg Val Met Val Ser Phe Arg Cys
65              70              75              80

Ala Glu Ala Ser Glu Ser Cys Pro Ile Ala Tyr Arg Cys Met Cys Arg
            85              90              95

Gly Arg Phe Phe Arg Val Pro Thr Leu
            100             105
```